United States Patent
Pillay et al.

(10) Patent No.: US 12,170,146 B2
(45) Date of Patent: Dec. 17, 2024

(54) OMNICHANNEL THERAPEUTIC PLATFORM

(71) Applicant: Reulay, Inc., Cambridge, MA (US)

(72) Inventors: Srinivasan S. Pillay, New York, NY (US); Patrick Candela, Greenlawn, NY (US); Abhishek Gupta, New York, NY (US)

(73) Assignee: Reulay, Inc., Cambridge, MA (US)

( * ) Notice: Subject to any disclaimer, the term of this patent is extended or adjusted under 35 U.S.C. 154(b) by 498 days.

(21) Appl. No.: 17/452,899

(22) Filed: Oct. 29, 2021

(65) Prior Publication Data

US 2022/0139554 A1 May 5, 2022

Related U.S. Application Data

(60) Provisional application No. 63/122,125, filed on Dec. 7, 2020, provisional application No. 63/108,735, filed on Nov. 2, 2020.

(51) Int. Cl.
*G16H 50/20* (2018.01)
*A61B 5/00* (2006.01)
(Continued)

(52) U.S. Cl.
CPC ........... *G16H 50/20* (2018.01); *A61B 5/4833* (2013.01); *G16H 20/10* (2018.01); *G16H 20/70* (2018.01); *G16H 40/67* (2018.01)

(58) Field of Classification Search
CPC ........ G16H 50/20; G16H 20/10; G16H 20/70; G16H 40/67; G16H 10/20; G16H 40/63;
(Continued)

(56) References Cited

U.S. PATENT DOCUMENTS 6,425,764 B1 7/2002 Lamson
8,913,911 B2 12/2014 Peters et al.
(Continued)

OTHER PUBLICATIONS

Kobayashi S, Koitabashi K. Effects of progressive muscle relaxation on cerebral activity: An fMRI investigation. Complement Ther Med. 2016;26:33-39. doi:10.1016/j.ctim.2016.02.010.
(Continued)

*Primary Examiner* — Robert W Morgan
*Assistant Examiner* — Liza Tony Kanaan
(74) *Attorney, Agent, or Firm* — Bookoff McAndrews, PLLC

(57) ABSTRACT

A computer-implemented method for treating a medical condition via a digital therapeutic platform, the method including receiving one or more user inputs, generating a script at a script generator, based on the one or more user inputs, determining therapeutic digital content by applying the script as an input to a therapeutic machine learning platform, receiving the therapeutic digital content via at least one of a therapeutic content database or a content generator, identifying a user platform to output the therapeutic digital content, modifying the therapeutic digital content for output via the user platform, providing the therapeutic digital content via the user platform, receiving feedback based on user consumption of the therapeutic digital content via the user platform and adjusting at least one of the script generator or the therapeutic machine learning platform based on the feedback.

20 Claims, 24 Drawing Sheets

(51) Int. Cl.
  *G16H 20/10* (2018.01)
  *G16H 20/70* (2018.01)
  *G16H 40/67* (2018.01)

(58) Field of Classification Search
  CPC ........ G16H 50/30; G16H 50/70; G16H 70/20;
  A61B 5/4833; Y02A 90/10
  See application file for complete search history.

(56) References Cited

U.S. PATENT DOCUMENTS

| | | | |
|---|---|---|---|
| 10,754,764 | B2 | 8/2020 | Lekivetz et al. |
| 2001/0029322 | A1* | 10/2001 | Iliff .................... G16H 15/00 600/300 |
| 2017/0039045 | A1* | 2/2017 | Abrahami .............. A61B 5/486 |
| 2020/0321124 | A1* | 10/2020 | Ford .................... A61B 5/7267 |
| 2021/0090694 | A1* | 3/2021 | Colley .................. G16H 20/10 |

OTHER PUBLICATIONS

Koren Y. The bellkor solution to the netflix grand prize. Netflix prize documentation. 2009.

Koutsikou S, Crook JJ, Earl EV, et al. Neural substrates underlying fear-evoked freezing: the periaqueductal grey-cerebellar link. J Physiol. 2014;592(Pt 10):2197-2213. doi:10.1113/jphysiol.2013. 268714.

Kraehenmann R, Pokorny D, Aicher H, et al. LSD Increases Primary Process Thinking via Serotonin 2A Receptor Activation. Front Pharmacol. 2017;8. doi:10.3389/fphar.2017.00814.

Kraehenmann R, Schmidt A, Friston K, Preller KH, Seifritz E, Vollenweider FX. The mixed serotonin receptor agonist psilocybin reduces threat-induced modulation of amygdala connectivity. NeuroImage Clin. 2015;11:53-60. doi:10.1016/i.nicl.2015.08.009.

Krebs TS, Johansen P-Ø. Psychedelics and Mental Health: A Population Study. PLoS ONE. 2013;8(8). doi:10.1371/journal.pone. 0063972.

Andauer TK. Latent Semantic Analysis. In: Encyclopedia of Cognitive Science. American Cancer Society; 2006. doi:10.1002/ 0470018860.s00561.

Lawrence M, Pringle J, Kerr S, Booth J, Govan L, Roberts NJ. Multimodal Secondary Prevention Behavioral Interventions for TIA and Stroke: A Systematic Review and Meta-Analysis. PLoS ONE. 2015;10(3). doi:10.1371/journal.pone.0120902.

Lee DD, Seung HS. Learning the parts of objects by non-negative matrix factorization. Nature. 1999;401:788-791.

Lee H, Battle A, Raina R, Ng A. Efficient sparse coding algorithms. Advances in Neural Information Processing Systems. 2007.

Lewis T. Johns Hopkins Scientists Give Psychedelics the Serious Treatment. Scientific American. Accessed Aug. 29, 2020. https:// www.scientificamerican.com/article/johns-hopkins-scientists-give-psychedelics-the-serious-treatment/.

Lähdepuro A, Savolainen K, Lahti-Pulkkinen M, et al. The Impact of Early Life Stress on Anxiety Symptoms in Late Adulthood. Sci Rep. 2019;9. doi:10.1038/s41598-019-40698-0.

Li X, Zhang M, Li K, et al. The Altered Somatic Brain Network in State Anxiety. Front Psychiatry. 2019;10. doi:10.3389/fpsyt.2019. 00465.

Liechti ME. Modern Clinical Research on LSD. Neuropsychopharmacology. 2017;42(11):2114-2127. doi:10.1038/ npp.2017.86.

Lillie EO, Patay B, Diamant J, Issell B, Topol EJ, Schork NJ. The n-of-1 clinical trial: the ultimate strategy for individualizing medicine? Pers Med. 2011;8(2):161-173. doi:10.2217/pme.11.7.

Lin C, Lee S-H, Huang C-M, et al. Increased brain entropy of resting-state fMRI mediates the relationship between depression severity and mental health-related quality of life in late-life depressed elderly. J Affect Disord. 2019;250:270-277. doi:10.1016/j.jad.2019. 03.012.

LoRaWAN Antennas, Data alliance, 2002-2021, https://www.data-alliance.net/lora-antennas-lorawan-long-range-iot/.

Loucks EB, Schuman-Olivier Z, Britton WB, et al. Mindfulness and Cardiovascular Disease Risk: State of the Evidence, Plausible Mechanisms, and Theoretical Framework. Curr Cardiol Rep. 2015;17(12):112. doi:10.1007/s11886-015-0668-7.

López-Giménez JF, González-Maeso J. Hallucinogens and Serotonin 5-HT2A Receptor-Mediated Signaling Pathways. Curr Top Behav Neurosci. 2018;36:45-73. doi:10.1007/7854_2017_478.

Ludwig AM. Altered states of consciousness. Arch Gen Psychiatry. 1966;15(3):225-234. doi:10.1001/archpsyc.1966.01730150001001.

Lux V. Epigenetic Programming Effects of Early Life Stress: A Dual-Activation Hypothesis. Curr Genomics. 2018;19 (8):638-652. doi:10.2174/1389202919666180307151358.

Ly C, Greb AC, Cameron LP, et al. Psychedelics Promote Structural and Functional Neural Plasticity. Cell Rep. 2018;23(11):3170-3182. doi:10.1016/j.celrep.2018.05.022.

Ma X, Yue Z-Q, Gong Z-Q, et al. The Effect of Diaphragmatic Breathing on Attention, Negative Affect and Stress in Healthy Adults. Front Psychol. 2017;8. doi:10.3389/fpsyg.2017.00874.

Ma Z, Wang C, Hines CS, et al. Frontoparietal network abnormalities of gray matter volume and functional connectivity in patients with generalized anxiety disorder. Psychiatry Res Neuroimaging. 2019;286:24-30. doi:10.1016/j.pscychresns.2019.03.001.

Makovac E, Smallwood J, Watson DR, Meeten F, Critchley HD, Ottaviani C. The verbal nature of worry in generalized anxiety: Insights from the brain. NeuroImage Clin. 2017;17:882-892. doi:10. 1016/j.nicl.2017.12.014.

Malhotra S, Sahoo S. Rebuilding the brain with psychotherapy. Indian J Psychiatry. 2017;59(4):411-419. doi:10.4103/0019-5545. 217299.

Mangini M. Treatment of alcoholism using psychedelic drugs: a review of the program of research. J Psychoactive Drugs. 1998;30(4):381-418. doi:10.1080/02791072.1998.10399714.

Margolin AA, Bilal E, Huang E, Norman TC, Ottestad L, Mecham BH, Sauerwine B, Kellen MR, Mangravite LM, Furia MD, Vollan HKM, Rueda OM, Guinney J, Deflaux NA, Hoff B, Schildwachter X, Russnes HG, Park D, Vang VO, Pirtle T, Youseff L, Citro C, Curtis C, Kristensen VN, Hellerstein J, Friend SH, Stolovitzky G, Aparicio S, Caldas C, Borresen-Dale AL. Systematic Analysis of Challenge-Driven Improvements in Molecular Prognostic Models for Breast Cancer. Sci Transl Med. 2013;5:181re1-181re1.

Massimo Fioranelli,, et al., Stress and Inflammation in Coronary Artery Disease: A Review Psychoneuroendocrineimmunology-Based, Front Immunol. 2018; 9: 2031.

Matthias E Liechti, Modern Clinical Research on LSD, Neuropsychopharmacology Oct. 2017;42(11):2114-2127.

McLaughlin KA, Hatzenbuehler ML. Stressful Life Events, Anxiety Sensitivity, and Internalizing Symptoms in Adolescents. J Abnorm Psychol. 2009;118(3):659-669. doi:10.1037/a0016499.

McRae K, Hughes B, Chopra S, Gabrieli JDE, Gross JJ, Ochsner KN. The Neural Bases of Distraction and Reappraisal. J Cogn Neurosci. 2010;22(2):248-262. doi:10.1162/jocn.2009.21243.

Menon B, Ramalingam K, Kumar R. Evaluating the Role of Oxidative Stress in Acute Ischemic Stroke. J Neurosci Rural Pract. 2020;11(1):156-159. doi:10.1055/s-0039-3402675.

Miller T, Nielsen L. Measure of Significance of Holotropic Breathwork in the Development of Self-Awareness. J Altern Complement Med N Y N. 2015;21(12):796-803. doi:10.1089/acm.2014.0297.

Modern Clinical Research on LSD | Neuropsychopharmacology. Accessed Sep. 6, 2020. https://www.nature.com/articles/ npp201786.

Molnar-Szakacs I, Uddin LQ. Self-Processing and the Default Mode Network: Interactions with the Mirror Neuron System. Front Hum Neurosci. 2013;7. doi:10.3389/fnhum.2013.00571.

Moncrieff J, Cohen D. How do psychiatric drugs work? The BMJ. 2009;338. doi:10.1136/bmj.b1963.

Moosavi A, Ardekani AM. Role of Epigenetics in Biology and Human Diseases. Iran Biomed J. 2016;20(5):246-258. doi:10.22045/ ibj.2016.01.

Mueller F, Lenz C, Dolder PC, et al. Acute effects of LSD on amygdala activity during processing of fearful stimuli in healthy subjects. Transl Psychiatry. 2017;7(4):e1084-e1084. doi:10.1038/ tp.2017.54.

(56) References Cited

OTHER PUBLICATIONS

Muthukumaraswamy SD, Carhart-Harris RL, Moran RJ, et al. Broadband Cortical Desynchronization Underlies the Human Psychedelic State. J Neurosci. 2013;33(38):15171-15183. doi:10.1523/JNEUROSCI.2063-13.2013.
Nichols DE, Johnson MW, Nichols CD. Psychedelics as Medicines: An Emerging New Paradigm. Clin Pharmacol Ther. 2017;101(2):209-219. doi:10.1002/cpt.557.
Niu Y, Wang B, Zhou M, et al. Dynamic Complexity of Spontaneous BOLD Activity in Alzheimer's Disease and Mild Cognitive Impairment Using Multiscale Entropy Analysis. Front Neurosci. 2018;12. doi:10.3389/fnins.2018.00677.
Nutt D. Psychedelic drugs—a new era in psychiatry? Dialogues Clin Neurosci. 2019;21(2):139-147. doi:10.31887/DCNS.2019.21.2/dnutt.
O'Brien PL, Thomas CP, Hodgkin D, Levit K, Mark TL. The diminished pipeline for medications to treat mental health and substance use disorders. Psychiatr Serv Wash DC. 2014;65(12):1433-1438. doi:10.1176/appi.ps.201400044.
Oliver R, Basit H. Embryology, Fertilization. In: StatPearls. StatPearls Publishing; 2020. Accessed Sep. 26, 2020. http://www.ncbi.nlm.nih.gov/books/NBK542186/, 4 pages.
Olshausen BA, Field DJ. Sparse coding with an overcomplete basis set: a strategy employed by V1? Vision Res. 1997;37:3311-3325.
O'Malley J, Kumar R, Inigo J, Yadava N, Chandra D. Mitochondrial Stress Response and Cancer. Trends Cancer. 2020;6(8):688-701. doi:10.1016/j.trecan.2020.04.009.
Pacholko AG, Wotton CA, Bekar LK. Poor Diet, Stress, and Inactivity Converge to Form a "Perfect Storm" That Drives Alzheimer's Disease Pathogenesis. Neurodegener Dis. 2019;19(2):60-77. doi:10.1159/000503451.
Park J, Moghaddam B. Impact of anxiety on prefrontal cortex encoding of cognitive flexibility. Neuroscience. 2017;345:193-202. doi:10.1016/j.neuroscience.2016.06.013.
Park J, Wood J, Bondi C, Del Arco A, Moghaddam B. Anxiety Evokes Hypofrontality and Disrupts Rule-Relevant Encoding by Dorsomedial Prefrontal Cortex Neurons. J Neurosci. 2016;36(11):3322-3335. doi: 10.1523/JNEUROSCI.4250-15.2016.
Ventrolateral periaqueductal gray neurons prioritize threat probability over fear output. Accessed Oct. 5, 2020. https://www.ncbi.nlm.nih.gov/pmc/articles/PMC6435320/.
Vytal KE, Overstreet C, Charney DR, Robinson OJ, Grillon C. Sustained anxiety increases amygdala-dorsomedial prefrontal coupling: a mechanism for maintaining an anxious state in healthy adults. J Psychiatry Neurosci JPN. 2014;39(5):321-329. doi:10.1503/jpn.130145.
Walters KL, Mohammed SA, Evans-Campbell T, Beltran RE, Chae DH, Duran B. Bodies Don't Just Tell Stories, They Tell Histories. Bois Rev Soc Sci Res Race. 2011;8(1):179-189. doi:10.1017/S1742058X1100018X.
Wang B, Niu Y, Miao L, et al. Decreased Complexity in Alzheimer's Disease: Resting-State fMRI Evidence of Brain Entropy Mapping. Front Aging Neurosci. 2017;9:378. doi:10.3389/fnagi.2017.00378.
Wang H-X, Wahlberg M, Karp A, Winblad B, Fratiglioni L. Psychosocial stress at work is associated with increased dementia risk in late life. Alzheimers Dement J Alzheimers Assoc. 2012;8(2):114-120. doi:10.1016/j.jalz.2011.03.001.
Wei D, Du X, Li W, et al. Regional gray matter vol. and anxiety-related traits interact to predict somatic complaints in a non-clinical sample. Soc Cogn Affect Neurosci. 2015;10(1):122-128. doi:10.1093/scan/nsu033.
Weiss AJ, Barrett ML, Heslin KC, Stocks C. Appendix A.2, List of ICD-9-CM diagnosis codes and descriptions (inclusion and exclusion criteria) for emergency department visits for depression, anxiety or stress reactions. Published Dec. 2016. Accessed Oct. 5, 2020. https://www.ncbi.nlm.nih.gov/books/NBK409512/table/sb216.t6/.
Wells RE, Kerr C, Dossett ML, et al. Can Adults with Mild Cognitive Impairment Build Cognitive Reserve and Learn Mindfulness Meditation? Qualitative Theme Analyses from a Small Pilot Study. J Alzheimers Dis JAD. 2019;70 (3):825-842. doi:10.3233/JAD-190191.
Winkelman MJ. The Mechanisms of Psychedelic Visionary Experiences: Hypotheses from Evolutionary Psychology. Front Neurosci. 2017;11. doi:10.3389/fnins.2017.00539.
Worthen M, Cash E. Stress Management. In: StatPearls. StatPearls Publishing; 2020. Accessed Aug. 30, 2020. http://www.ncbi.nlm.nih.gov/books/NBK513300/.
Wu JQ, Szpunar KK, Godovich SA, Schacter DL, Hofmann SG. Episodic Future Thinking in Generalized Anxiety Disorder. J Anxiety Disord. 2015;36:1-8. doi:10.1016/j.janxdis.2015.09.005.
Xue S-W, Guo Y, Alzheimer's Disease Neuroimaging Initiative. Increased resting-state brain entropy in Alzheimer's disease. Neuroreport. 2018;29(4):286-290. doi:10.1097/WNR.0000000000000942.
Xue S-W, Wang D, Tan Z, et al. Disrupted Brain Entropy And Functional Connectivity Patterns Of Thalamic Subregions In Major Depressive Disorder. Neuropsychiatr Dis Treat. 2019;15:2629-2638. doi:10.2147/NDT.S220743.
Yogatama D, Faruqui M, Dyer C, Smith NA. Learning Word Representations with Hierarchical Sparse Coding. CORD Conference Proceedings. 2014.
Zaccaro A, Piarulli A, Laurino M, et al. How Breath-Control Can Change Your Life: A Systematic Review on Psycho-Physiological Correlates of Slow Breathing. Front Hum Neurosci. 2018;12. doi:10.3389/fnhum.2018.00353.
Zamberlan F, Sanz C, Martínez Vivot R, et al. The Varieties of the Psychedelic Experience: A Preliminary Study of the Association Between the Reported Subjective Effects and the Binding Affinity Profiles of Substituted Phenethylamines and Tryptamines. Front Integr Neurosci. 2018;12. doi:10.3389/fnint.2018.00054.
Zatti A, Zarbo C. Embodied and exbodied mind in clinical psychology. A proposal for a psycho-social interpretation of mental disorders. Front Psychol. 2015;6. doi:10.3389/fpsyg.2015.00236.
Zeeshan Ahmed, et al., Artificial intelligence with multi-functional machine learning platform development for better healthcare and precision medicine, Database (Oxford). 2020.
Zhang L, Pan J, Chen W, Jiang J, Huang J. Chronic stress-induced immune dysregulation in cancer: implications for initiation, progression, metastasis, and treatment. Am J Cancer Res. 2020;10(5):1294-1307.
Zheng F, Duan Y, Li J, et al. Somatic symptoms and their association with anxiety and depression in Chinese patients with cardiac neurosis. J Int Med Res. 2019;47(10):4920-4928. doi:10.1177/0300060519869711.
Zhu S, Jiang Y, Xu K, et al. The progress of gut microbiome research related to brain disorders. J Neuroinflammation. 2020;17. doi:10.1186/s12974-020-1705-z.
(PDF) Sound Healing using Solfeggio Frequencies. ResearchGate. Accessed Sep. 7, 2020. https://www.researchgate.net/publication/333852911_Sound_Healing_using_Solfeggio_Frequencies.
Pena-Castillo L, et al., "A critical assessment of Mus musculus gene function prediction using integrated genomic evidence," Genome Biol. 2008;9(Suppl 1):S2.
Pitt B, Pfeffer MA, Assmann SF, Boineau R, Anand IS, Claggett B, Clausell N, Desai AS, Diaz R, Fleg JL, Gordeev I, Harty B, Heitner JF, Kenwood CT, Lewis EF, O'Meara E, Probstfield JL, Shaburishvili T, Shah SJ, Solomon SD, Sweitzer NK, Yang S, McKinlay SM TOPCAT Investigators. Spironolactone for heart failure with preserved ejection fraction. N Engl J Med. 2014;370:1383-1392.
Printz C. Psychological stress is associated with a higher risk of cervical cancer mortality. Cancer. 2020;126 (2):240-241. doi:10.1002/cncr.32686.
Rahul C. Deo., Machine Learning in Medicine, Circulation. Nov. 17, 2015; 132(20): 1920-1930.
Rahul C. Deo., Machine Learning in Medicine, Circulation. Nov. 17, 2015; 132(20): 1920-1930. Figure 1A, URL: https://www.ncbi.nlm.nih.gov/pmc/articles/PMC5831252/figure/F1/.
Rahul C. Deo., Machine Learning in Medicine, Circulation. Nov. 17, 2015; 132(20): 1920-1930. Figure 1B, URL: https://www.ncbi.nlm.nih.gov/pmc/articles/PMC5831252/figure/F1/.

(56) References Cited

OTHER PUBLICATIONS

Rahul C. Deo., Machine Learning in Medicine, Circulation. Nov. 17, 2015; 132(20): 1920-1930. Figure 1B-D, URL: https://www.ncbi.nlm.nih.gov/pmc/articles/PMC5831252/figure/F1/.
Rahul C. Deo., Machine Learning in Medicine, Circulation. Nov. 17, 2015; 132(20): 1920-1930. Figure 1C, URL: https://www.ncbi.nlm.nih.gov/pmc/articles/PMC5831252/figure/F1/.
Rahul C. Deo., Machine Learning in Medicine, Circulation. Nov. 17, 2015; 132(20): 1920-1930. Figure 1D, URL: https://www.ncbi.nlm.nih.gov/pmc/articles/PMC5831252/figure/F1/.
Rahul C. Deo., Machine Learning in Medicine, Circulation. Nov. 17, 2015; 132(20): 1920-1930. Figure 3, URL: https://www.ncbi.nlm.nih.gov/pmc/articles/PMC5831252/figure/F3/.
Rahul C. Deo., Machine Learning in Medicine, Circulation. Nov. 17, 2015; 132(20): 1920-1930. Figure 4A, URL: https://www.ncbi.nlm.nih.gov/pmc/articles/PMC5831252/figure/F4/.
Rahul C. Deo., Machine Learning in Medicine, Circulation. Nov. 17, 2015; 132(20): 1920-1930. Figure 4B, URL:https://www.ncbi.nlm.nih.gov/pmc/articles/PMC5831252/figure/F4/.
Rahul C. Deo., Machine Learning in Medicine, Circulation. Nov. 17, 2015; 132(20): 1920-1930. Figure 4C, URL: https://www.ncbi.nlm.nih.gov/pmc/articles/PMC5831252/figure/F4/.
Rakesh G, Szabo ST, Alexopoulos GS, Zannas AS. Strategies for dementia prevention: latest evidence and implications. Ther Adv Chronic Dis. 2017;8(8-9):121-136. doi:10.1177/2040622317712442.
Ratcliffe M, Ruddell M, Smith B. What is a "sense of foreshortened future?" A phenomenological study of trauma, trust, and time. Front Psychol. 2014;5. doi:10.3389/fpsyg.2014.01026.
Rebecca J. Schlegel, et al., Thine Own Self: True Self-Concept Accessibility and Meaning in Life, J Pers Soc Psychol. Feb. 2009; 96(2): 473-490.
Redpill VR—Redpill is a platform for the creation and distribution of virtual social music experiences. Accessed Nov. 9, 2020. https://www.redpillvr.com/.
Ressler KJ. Amygdala Activity, Fear, and Anxiety: Modulation by Stress. Biol Psychiatry. 2010;67(12):1117-1119. doi:10.1016/j.biopsych.2010.04.027.
Richards SH, Anderson L, Jenkinson CE, et al. Psychological interventions for coronary heart disease. Cochrane Database Syst Rev. 2017;2017(4). doi:10.1002/14651858.CD002902.pub4.
Sakurai T. Circuitry-Based Human Neuroanatomy for the Next Generation in Psychiatry and Neuroscience. Mol Neuropsychiatry. 2017;3(2):92-96. doi:10.1159/000479514.
Sara JD, Prasad M, Eleid MF, Zhang M, Widmer RJ, Lerman A. Association Between Work-Related Stress and Coronary Heart Disease: A Review of Prospective Studies Through the Job Strain, Effort-Reward Balance, and Organizational Justice Models. J Am Heart Assoc Cardiovasc Cerebrovaso Dis. 2018;7(9). doi:10.1161/JAHA.117.008073.
Saxe GN, Calderone D, Morales LJ. Brain entropy and human intelligence: A resting-state fMRI study. PloS One. 2018;13(2):e0191582. doi:10.1371/journal.pone.0191582.
Schenberg EE. Psychedelic-Assisted Psychotherapy: A Paradigm Shift in Psychiatric Research and Development. Front Pharmacol. 2018;9. doi:10.3389/fphar.2018.00733.
Schneider RH, Grim CE, Rainforth MV, et al. Stress Reduction in the Secondary Prevention of Cardiovascular Disease. Circ Cardiovasc Qual Outcomes. 2012;5(6):750-758. doi:10.1161/CIRCOUTCOMES.112.967406.
Schoen CB, Holtzer R. Differential Relationships of Somatic and Cognitive Anxiety with Measures of Processing Speed in Older Adults. Neuropsychol Dev Cogn B Aging Neuropsychol Cogn. 2017;24(5):481-495. doi:10.1080/13825585.2016.1226247.
Schwabe L, Wolf OT. Stress prompts habit behavior in humans. J Neurosci Off J Soc Neurosci. 2009;29 (22):7191-7198. doi: 10.1523/JNEUROSCI.0979-09.2009.
Scott G, Carhart-Harris RL. Psychedelics as a treatment for disorders of consciousness. Neurosci Conscious. 2019;2019(1). doi:10.1093/nc/niz003.
Senior K. Stress increases risk of ischemic stroke. Nat Rev Neurol. 2009;5(12):635-635. doi:10.1038/nrneurol.2009.181.
Seo H-J, Choi YH, Chung Y-A, Rho W, Chae J-H. Changes in cerebral blood flow after cognitive behavior therapy in patients with panic disorder: a SPECT study. Neuropsychiatr Dis Treat. 2014;10:661-669. doi:10.2147/NDT.S58660.
Shah SJ, Katz DH, Selvaraj S, Burke MA, Yancy CW, Gheorghiade M, Bonow RO, Huang C-C, Deo RC. Phenomapping for novel classification of heart failure with preserved ejection fraction. Circulation. 2015;131:269-279.
Siegrist J, Li J. Work Stress and the Development of Chronic Diseases. Int J Environ Res Public Health. 2018;15(3). doi:10.3390/ijerph15030536.
Sin NL. The Protective Role of Positive Well-Being in Cardiovascular Disease: Review of Current Evidence, Mechanisms, and Clinical Implications. Curr Cardiol Rep. 2016;18(11):106. doi:10.1007/s11886-016-0792-z.
Su Y, Yuki M, Otsuki M. Non-Pharmacological Interventions for Post-Stroke Fatigue: Systematic Review and Network Meta-Analysis. J Clin Med. 2020;9(3). doi:10.3390/jcm9030621.
Sun H, Huang H, Ji S, et al. The Efficacy of Cognitive Behavioral Therapy to Treat Depression and Anxiety and Improve Quality of Life Among Early-Stage Breast Cancer Patients. Integr Cancer Ther. 2019;18. doi:10.1177/1534735419829573.
Surman M, Janik ME. Stress and its molecular consequences in cancer progression. Postepy Hig Med Doswiadczalnej Online. 2017;71(0):485-499. doi:10.5604/01.3001.0010.3830.
Swanson LR. Unifying Theories of Psychedelic Drug Effects. Front Pharmacol. 2018;9. doi:10.3389/fphar.2018.00172.
Sylvester CM, Corbetta M, Raichle ME, et al. Functional network dysfunction in anxiety and anxiety disorders. Trends Neurosci. 2012;35(9):527-535. doi:10.1016/j.tins.2012.04.012.
Tarozzi A. Oxidative Stress in Neurodegenerative Diseases: From Preclinical Studies to Clinical Applications. J Clin Med. 2020;9(4). doi:10.3390/jcm9041223.
Taylor AG, Goehler LE, Galper DI, Innes KE, Bourguignon C. Top-Down and Bottom-Up Mechanisms in Mind-Body Medicine: Development of an Integrative Framework for Psychophysiological Research. Explore N Y N. 2010;6(1):29. doi:10.1016/j.explore.2009.10.004.
Thau L, Reddy V, Singh P. Anatomy, Central Nervous System. In: StatPearls. StatPearls Publishing; 2020. Accessed Sep. 26, 2020. http://www.ncbi.nlm.nih.gov/books/NBK542179/.
The brain on art: intense aesthetic experience activates the default mode network. Accessed Oct. 5, 2020. https://www.ncbi.nlm.nih.gov/pmc/articles/PMC3330757/.
The Effects of 528 Hz Sound Wave to Reduce Cell Death in Human Astrocyte Primary Cell Culture Treated with Ethanol | OMICS International. Accessed Sep. 7, 2020. https://www.omicsonline.org/open-access/the-effects-of-528-hz-sound-wave-to-reduce-cell-death-in-human-astrocyteprimary-cell-culture-treated-with-ethanol-2155-6105-1000335.php?aid=91771.
The Neural Correlate Difference Between Positive and Negative Awe. Accessed Oct. 5, 2020. https://www.ncbi.nlm.nih.gov/pmc/articles/PMC6597956/.
The top 10 causes of death. Accessed Sep. 26, 2020. https://www.who.int/news-room/fact-sheets/detail/the-top-10-causes-of-death, 9 pages.
Thomas R. Insel, MD., Psychiatry as a Clinical Neuroscience Discipline, JAMA. Nov. 2, 2005; 294(17): 2221-2224.
Toivanen S. Social Determinants of Stroke as Related to Stress at Work among Working Women: A Literature Review. Stroke Res Treat. 2012;2012. doi:10.1155/2012/873678.
Toscher A, Jahrer M, Bell RM. The bigchaos solution to the netflix grand prize. Netflix prize documentation. 2009.
Udelson JE. Heart Failure With Preserved Ejection Fraction. Circulation. 2011;124:e540-e543.
Vapnik VN. An overview of statistical learning theory. IEEE Trans Neural Netw. 1999;10:988-999.
2.4GHz WiFi, Bluetooth, ISM, ISM Band of Frequencies and Allocation, Data alliance, 2002-2021, https://www.data-alliance.net/antennas-2-4ghz/.

(56) References Cited

OTHER PUBLICATIONS 412-440MHz Antennas, Data alliance, 2002-2021, https://www.data-alliance.net/433mhz-antennas/.
5GHz: 4.9~6.0GHz Antennas, 5.1 to 5.8 GHz Frequency Band, Data alliance, 2002-2021, https://www.data-alliance.net/antennas-5ghz/.
According to the DSM-5, which diagnoses are classified as anxiety disorders? Accessed Oct. 5, 2020. https://www.medscape.com/answers/286227-14511/according-to-the-dsm-5-which-diagnoses-are-classified-as-anxiety-disorders.
Aideyan B, Martin GC, Beeson ET. A Practitioner's Guide to Breathwork in Clinical Mental Health Counseling. J Ment Health Couns. 2020;42(1):78-94. doi:10.17744/mehc.42.1.06.
Akimoto K, Kobayashi H, Yamaguchi T, Hu A. Effect of 528 Hz Music on the Endocrine System and Autonomic Nervous System. Health (N Y). 2018;10(9):720-726. doi:10.4236/health.2018.109088.
Almeida AP, Silva MJP da. Canto Gregoriano: redutor de ansiedade de mães com filhos hospitalizados. Acta Paul Enferm. 2012;25(1):36-42. doi:10.1590/S0103-21002012000100007.
Andreescu C, Mennin D, Tudorascu D, et al. The many faces of anxiety—neurobiological correlates of anxiety phenotypes. Psychiatry Res. 2015;234(1):96-105. doi:10.1016/j.pscychresns.2015.08.013.
Antoni MH, Dhabhar FS. The impact of psychosocial stress and stress management on immune responses in patients with cancer. Cancer. 2019;125(9):1417-1431. doi:10.1002/cncr.31943.
Anxiety Disorders are Associated with Reduced Heart Rate Variability: A Meta-Analysis. Accessed Oct. 5, 2020. https://www.ncbi.nlm.nih.gov/pmc/articles/PMC4092363/.
Aravena PC, Almonacid C, Mancilla MI. Effect of music at 432 Hz and 440 Hz on dental anxiety and salivary cortisol levels in patients undergoing tooth extraction: a randomized clinical trial. J Appl Oral Sci. 28. doi:10.1590/1678-7757-2019-0601.
Arcangeli M, Sperduti M, Jacquot A, Piolino P, Dokic J. Awe and the Experience of the Sublime: A Complex Relationship. Front Psychol. 2020;11. doi:10.3389/fpsyg.2020.01340.
Babayi Daylari T, Riazi GH, Pooyan S, Fathi E, Hedayati Katouli F. Influence of various intensities of 528 Hz sound-wave in production of testosterone in rat's brain and analysis of behavioral changes. Genes Genomics. 2019;41(2):201-211. doi:10.1007/s13258-018-0753-6.
Bakalar JB, Grinspoon L. Psychedelic Drugs Reconsidered. 3rd Edition. The Lindesmith Center; 1997.
Barre PV, Padmaja G, Rana S, Tiamongla. Stress and Quality of Life in Cancer Patients: Medical and Psychological Intervention. Indian J Psychol Med. 2018;40(3):232-238. doi:10.4103/IJPSYM.IJPSYM_512_17.
Barrett LF, Bliss-Moreau E, Duncan SL, Rauch SL, Wright CI. The amygdala and the experience of affect. Soc Cogn Affect Neurosci. 2007;2(2):73-83. doi:10.1093/scan/nsl042.
Beesdo K, Lau JYF, Guyer AE, et al. Common and Distinct Amygdala-Function Perturbations in Depressed vs Anxious Adolescents. Arch Gen Psychiatry. 2009;66(3):275-285. doi:10.1001/archgenpsychiatry.2008.545.
Bennis W. On Becoming a Leader. 4 edition. Basic Books; 2009.
Benoit RG, Davies DJ, Anderson MC. Reducing future fears by suppressing the brain mechanisms underlying episodic simulation. Proc Natl Acad Sci U S A. 2016;113(52):E8492-E8501. doi:10.1073/pnas.1606604114.
Berretta S, Heckers S, Benes FM. Searching Human Brain for Mechanisms of Psychiatric Disorders. Schizophr Res. 2015;167(0):91-97. doi:10.1016/j.schres.2014.10.019.
Bird S. NLTK: the natural language toolkit. In: Proceedings of the COLING/ACL on Interactive Presentation Sessions. COLING-ACL '06. Association for Computational Linguistics; 2006:69-72. doi:10.3115/1225403.1225421.
Blanc-Lapierre A, Rousseau M-C, Parent M-E. Perceived Workplace Stress Is Associated with an Increased Risk of Prostate Cancer before Age 65. Front Oncol. 2017;7. doi:10.3389/fonc.2017.00269.

Blons E, Arsac LM, Gilfriche P, et al. Alterations in heart-brain interactions under mild stress during a cognitive task are reflected in entropy of heart rate dynamics. Sci Rep. 2019;9. doi:10.1038/s41598-019-54547-7.
Blumenthal JA, Sherwood A, Smith PJ, et al. Enhancing Cardiac Rehabilitation With Stress Management Training: A Randomized Clinical Efficacy Trial. Circulation. 2016;133(14):1341-1350. doi:10.1161/CIRCULATIONAHA.115.018926.
Bond S, Lopez-Lloreda C, Gannon PJ, Akay-Espinoza C, Jordan-Sciutto KL. The Integrated Stress Response and Phosphorylated Eukaryotic Initiation Factor 2α in Neurodegeneration. J Neuropathol Exp Neurol. 2020;79(2):123-143. doi:10.1093/jnen/nlz129.
Booth J, Connelly L, Lawrence M, et al. Evidence of perceived psychosocial stress as a risk factor for stroke in adults: a meta-analysis. BMC Neurol. 2015;15. doi:10.1186/s12883-015-0456-4.
Brain Electrical Activity Mapping for Diagnosing Psychiatric Disorders: A Review of the Clinical Evidence [Internet]. Nov. 2014, Retrieved from the internet: https://www.ncbi.nlm.nih.gov/books/NBK263331/.
Breathlessness: From Bodily Symptom to Existential Experience—Existential Medicine—NCBI Bookshelf. Accessed Oct. 5, 2020. https://www.ncbi.nlm.nih.gov/books/NBK535717/.
Breiman L. Random forests. Mach Learn. 2001;45:5-32.
Brooks SJ, Stein DJ. A systematic review of the neural bases of psychotherapy for anxiety and related disorders. Dialogues Clin Neurosci. 2015;17(3):261-279.
Brown JC, Gerhardt TE, Kwon E. Risk Factors For Coronary Artery Disease. In: StatPearls. StatPearls Publishing; 2020. Accessed Aug. 30, 2020. http://www.ncbi.nlm.nih.gov/books/NBK554410/.
Burges CJ. A tutorial on support vector machines for pattern recognition. Data Min Knowl Discov. 1998;2:121-167.
Butler G. Definitions of stress. Occas Pap R Coll Gen Pract. 1993;(61):1-5.
Cahn BR, Polich J. Meditation (Vipassana) and the P3a Event-Related Brain Potential. Int J Psychophysiol Off J Int Organ Psychophysiol. 2009;72(1):51-60. doi:10.1016/j.ijpsycho.2008.03.013.
Calamassi D, Pomponi GP. Music Tuned to 440 Hz Versus 432 Hz and the Health Effects: A Double-blind Cross-over Pilot Study. Explore N Y N. 2019;15(4):283-290. doi:10.1016/j.explore.2019.04.001.
Camplesi M, de Bortoli VC, de Paula Soares V, Nogueira RL, Zangrossi H. Dorsal periaqueductal gray stimulation facilitates anxiety-, but not panic-related, defensive responses in rats tested in the elevated T-maze. Braz J Med Biol Res. 2012;45(11):1025-1030. doi:10.1590/S0100-879X2012007500124.
Carhart-Harris RL, Erritzoe D, Williams T, et al. Neural correlates of the psychedelic state as determined by fMRI studies with psilocybin. Proc Natl Acad Sci U S A. 2012;109(6):2138-2143. doi:10.1073/pnas.1119598109.
Carhart-Harris RL, Friston KJ. Rebus and the Anarchic Brain: Toward a Unified Model of the Brain Action of Psychedelics. Pharmacol Rev. 2019;71(3):316-344. doi:10.1124/pr.118.017160.
Carhart-Harris RL, Goodwin GM. The Therapeutic Potential of Psychedelic Drugs: Past, Present, and Future. Neuropsychopharmacology. 2017;42(11):2105-2113. doi:10.1038/npp.2017.84.
Carhart-Harris RL, Leech R, Hellyer PJ, et al. The entropic brain: a theory of conscious states informed by neuroimaging research with psychedelic drugs. Front Hum Neurosci. 2014;8. doi:10.3389/fnhum.2014.00020.
Carhart-Harris RL, Muthukumaraswamy S, Roseman L, et al. Neural correlates of the LSD experience revealed by multimodal neuroimaging. Proc Natl Acad Sci. 2016;113(17):4853-4858. doi:10.1073/pnas.1518377113.
Carlisi CO, Robinson OJ. The role of prefrontal-subcortical circuitry in negative bias in anxiety: Translational, developmental and treatment perspectives. Brain Neurosci Adv. 2018;2. doi:10.1177/2398212818774223.
Chail A, Saini RK, Bhat PS, Srivastava K, Chauhan V. Transcranial magnetic stimulation: A review of its evolution and current applications. Ind Psychiatry J. 2018;27(2):172-180. doi:10.4103/ipj.ipj_88_18.

(56) References Cited

OTHER PUBLICATIONS

Chaudhry R, Miao JH, Rehman A. Physiology, Cardiovascular. In: StatPearls. StatPearls Publishing; 2020. Accessed Sep. 26, 2020. http://www.ncbi.nlm.nih.gov/books/NBK493197/.
Chen R., "Design Patents for Animated Images: Development Trends," Journal of Intellectual Property Rights, Jan. 2014, vol. 19, pp. 43-48.
Cheng W-Y, Ou Yang T-H, Anastassiou D. Biomolecular events in cancer revealed by attractor metagenes. PLoS Comput Biol. 2013;9:e1002920.
Cheng WY, Yang THO, Anastassiou D. Development of a Prognostic Model for Breast Cancer Survival in an Open Challenge Environment. Sci Transl Med. 2013;5:181ra50.
Clauss JA, Benningfield MM, Rao U, Blackford JU. Altered Prefrontal Cortex Function Marks Heightened Anxiety Risk in Children. J Am Acad Child Adolesc Psychiatry. 2016;55(9):809-816. doi:10.1016/j.jaac.2016.05.024.
Cohen S. Lysergic acid diethylamide: side effects and complications. J Nerv Ment Dis. 1960;130:30-40. doi:10.1097/00005053-196001000-00005.
Coker-Appiah DS, White SF, Clanton R, Yang J, Martin A, Blair RJR. Looming animate and inanimate threats: The response of the amygdala and periaqueductal gray. Soc Neurosci. 2013;8(6):621-630. doi:10.1080/17470919.2013.839480.
Cole MW, Repovs G, Anticevic A. The frontoparietal control system: A central role in mental health. Neurosci Rev J Bringing Neurobiol Neurol Psychiatry. 2014;20(6):652-664. doi:10.1177/1073858414525995.
Commissioner O of the. FDA Permits Marketing of First Game-Based Digital Therapeutic to Improve Attention Function in Children with ADHD. FDA. Published Jun. 17, 2020. Accessed Sep. 6, 2020. https://www.fda.gov/news-events/press-announcements/fda-permits-marketing-first-game-based-digital-therapeutic-improve-attention-function-children-adhd.
Complete Substance and Category List : Erowid Experience Vaults. Accessed Sep. 7, 2020. https://www.erowid.org/experiences/exp_list.shtml.
Cover T, Hart P. Nearest neighbor pattern classification. IEEE Trans Inf Theory. 1967;13:21-27.
Crocq M-A. A history of anxiety: from Hippocrates to DSM. Dialogues Clin Neurosci. 2015;17(3):319-325.
Davey CG, Harrison BJ. The brain's center of gravity: how the default mode network helps us to understand the self. World Psychiatry. 2018;17(3):278-279. doi:10.1002/wps.20553.
Deo RC, Musso G, Taan M, Tang P, Poon A, Yuan C, Felix JF, Vasan RS, Beroukhim R, De Marco T, Kwok P-Y, Macrae CA, Roth FP. Prioritizing causal disease genes using unbiased genomic features. Genome Biol. 2014;15:534.
Desbordes G, Negi LT, Pace TWW, Wallace BA, Raison CL, Schwartz EL. Effects of mindful-attention and compassion meditation training on amygdala response to emotional stimuli in an ordinary, non-meditative state. Front Hum Neurosci. 2012;6. doi:10.3389/fnhum.2012.00292.
Di Nasso L, Nizzardo A, Pace R, Pierleoni F, Pagavino G, Giuliani V. Influences of 432 Hz Music on the Perception of Anxiety during Endodontic Treatment: A Randomized Controlled Clinical Trial. J Endod. 2016;42(9):1338-1343. doi:10.1016/j.joen.2016.05.015.
Dimitriev DA, Saperova EV, Dimitriev AD. State Anxiety and Nonlinear Dynamics of Heart Rate Variability in Students. PLoS ONE. 2016;11(1). doi:10.1371/journal.pone.0146131.
Dimsdale JE. Psychological Stress and Cardiovascular Disease. J Am Coll Cardiol. 2008;51(13):1237-1246. doi:10.1016/j.jacc.2007.12.024.
Dorthe Djernis, et al., A Systematic Review and Meta-Analysis of Nature-Based Mindfulness: Effects of Moving Mindfulness Training into an Outdoor Natural Setting, Int J Environ Res Public Health. Sep. 2019; 16(17): 3202.
Douglas Heaven, Video stored in live bacterial genome using CRISPR gene editing, Jul. 12, 2017, Retrieved from the Internet: https://www.newscientist.com/article/2140576-video-stored-in-live-bacterial-genome-using-crispr-gene-editing/.
Dubey P, Kumar Y, Singh R, Jha K, Kumar R. Effect of music of specific frequency upon the sleep architecture and electroencephalographic pattern of individuals with delayed sleep latency: A daytime nap study. J Fam Med Prim Care. 2019;8(12):3915-3919. doi:10.4103/jfmpc.jfmpc_575_19.
Economides M, Martman J, Bell MJ, Sanderson B. Improvements in Stress, Affect, and Irritability Following Brief Use of a Mindfulness-based Smartphone App: A Randomized Controlled Trial. Mindfulness. 2018;9(5): 1584-1593. doi:10.1007/s12671-018-0905-4.
Eugene Lin, et al., Precision Psychiatry Applications with Pharmacogenomics: Artificial Intelligence and Machine Learning Approaches, Int J Mol Sci. Feb. 2020; 21(3): 969.
Fox AS, Shackman AJ. The central extended amygdala in fear and anxiety: Closing the gap between mechanistic and neuroimaging research. Neurosci Lett. 2019;693:58-67. doi:10.1016/j.neulet.2017.11.056.
Francis AL, Beemer RC. How does yoga reduce stress? Embodied cognition and emotion highlight the influence of the musculoskeletal system. Complement Ther Med. 2019;43:170-175. doi:10.1016/j.ctim.2019.01.024.
Friedman JH. Greedy function approximation: A gradient boosting machine. Ann Statist. 2001;29:1189-1232.
Frommeyer G, Eckardt L, Breithardt G. Panic attacks and supraventricular tachycardias: the chicken or the egg? Neth Heart J. 2013;21(2):74-77. doi:10.1007/s12471-012-0350-2.
Fuentes JJ, Fonseca F, Elices M, Farré M, Torrens M. Therapeutic Use of LSD in Psychiatry: A Systematic Review of Randomized-Controlled Clinical Trials. Front Psychiatry. 2020;10. doi:10.3389/fpsyt.2019.00943.
Full article: Meditation-induced neuroplastic changes in amygdala activity during negative affective processing. Accessed Oct. 5, 2020. https://www.tandfonline.com/doi/full/10.1080/17470919.2017.1311939, 12 pages.
Genomeweb, US Supreme Court Strikes Down Gene Patents but Allows Patenting of Synthetic DNA, Jun. 13, 2013, https://www.genomeweb.com/diagnostics/us-supreme-court-strikes-down-gene-patents-allows-patenting-synthetic-dna#.X1ib-C3Mzzl.
Gold AL, Shechner T, Farber MJ, et al. Amygdala-cortical connectivity: Associations with anxiety, development, and threat. Depress Anxiety. 2016;33(10):917-926. doi:10.1002/da.22470.
Gottschalk MG, Domschke K, Schiele MA. Epigenetics Underlying Susceptibility and Resilience Relating to Daily Life Stress, Work Stress, and Socioeconomic Status. Front Psychiatry. 2020;11. doi:10.3389/fpsyt.2020.00163.
Graeff FG. Serotonin, the periaqueductal gray and panic. Neurosci Biobehav Rev. 2004;28(3):239-259. doi:10.1016/j.neubiorev.2003.12.004.
Griffiths RR, Johnson MW, Carducci MA, et al. Psilocybin produces substantial and sustained decreases in depression and anxiety in patients with life-threatening cancer: A randomized double-blind trial. J Psychopharmacol Oxf Engl. 2016;30(12):1181-1197. doi:10.1177/0269881116675513.
Grinspoon L, Bakalar JB. The psychedelic drug therapies. Curr Psychiatr Ther. 1981;20:275-283.
Guarino A, Polini C, Forte G, Favieri F, Boncompagni I, Casagrande M. The Effectiveness of Psychological Treatments in Women with Breast Cancer: A Systematic Review and Meta-Analysis. J Clin Med. 2020;9(1). doi:10.3390/jcm9010209.
Haluk Öğmen, et al., The Geometry of Visual Perception: Retinotopic and Non-retinotopic Representations in the Human Visual System, Proc IEEE Inst Electr Electron Eng. 2010; 98(3): 479-492.
Harsanyiova J, Buday T, Kralova Trancikova A. Parkinson's Disease and the Gut: Future Perspectives for Early Diagnosis. Front Neurosci. 2020;14. doi:10.3389/fnins.2020.00626.
Hofmann SG, Gómez AF. Mindfulness-Based Interventions for Anxiety and Depression. Psychiatr Clin North Am. 2017;40(4):739-749. doi:10.1016/j.psc.2017.08.008.
Hoge EA, Bui E, Goetter E, et al. Change in Decentering Mediates Improvement in Anxiety in Mindfulness-Based Stress Reduction for Generalized Anxiety Disorder. Cogn Ther Res. 2015;39(2):228-235. doi:10.1007/s10608-014-9646-4.

(56) References Cited

OTHER PUBLICATIONS

Hotamisligil GS. Foundations of Immunometabolism and Implications for Metabolic Health and Disease. Immunity. 2017;47(3):406-420. doi:10.1016/j.immuni.2017.08.009.

How chronic stress boosts cancer cell growth. Published Feb. 25, 2019. Accessed Aug. 30, 2020. https://www.medicalnewstoday.com/articles/324540.

Hur J, Stockbridge MD, Fox AS, Shackman AJ. Dispositional negativity, cognition, and anxiety disorders: An integrative translational neuroscience framework. Prog Brain Res. 2019;247:375-436. doi:10.1016/bs.pbr.2019.03.012.

Hur Y-J, McManus IC. Representing the sublime in the VIMAP and empirical aesthetics: Reviving Edmund Burke's A Philosophical Enquiry into the Origins of Our Ideas of the Sublime and Beautiful: Comment on "Move me, astonish me . . . delight my eyes and brain: The Vienna Integrated Model of top-down and bottom-up processes in Art Perception (VIMAP) and corresponding affective, evaluative, and neurophysiological correlates" by Matthew Pelowski et al. Phys Life Rev. 2017;21:135-137. doi:10.1016/j.plrev.2017.05.004.

Information NC for B, Pike USNL of M 8600 R, MD B, Usa 20894. Summary of Evidence. Canadian Agency for Drugs and Technologies in Health; 2014. Accessed Sep. 6, 2020. https://www.ncbi.nlm.nih.gov/books/NBK263332/.

Innes KE, Selfe TK. Meditation as a Therapeutic Intervention for Adults at Risk for Alzheimer's Disease—Potential Benefits and Underlying Mechanisms. Front Psychiatry. 2014;5. doi:10.3389/fpsyt.2014.00040.

IoT (Internet of Things) Wireless Protocols and Their Frequency Bands. Data-alliance.net. Accessed Sep. 7, 2020. https://www.data-alliance.net/blog/iot-internet-of-things-wireless-protocols-and-their-frequency-bands/.

Ishizu T, Zeki S. A neurobiological enquiry into the origins of our experience of the sublime and beautiful. Front Hum Neurosci. 2014;8. doi:10.3389/fnhum.2014.00891.

Jing HG, Madore KP, Schacter DL. Worrying about the Future: An Episodic Specificity Induction Impacts Problem Solving, Reappraisal, and Well-Being. J Exp Psychol Gen. 2016;145(4):402-418. doi:10.1037/xge0000142.

Joo HM, Lee SJ, Chung YG, Shin IY. Effects of Mindfulness Based Stress Reduction Program on Depression, Anxiety and Stress in Patients with Aneurysmal Subarachnoid Hemorrhage. J Korean Neurosurg Soc. 2010;47(5):345-351. doi:10.3340/jkns.2010.47.5.345.

Justice NJ. The relationship between stress and Alzheimer's disease. Neurobiol Stress. 2018;8:127-133. doi:10.1016/j.ynstr.2018.04.002.

Kalisch R, Wiech K, Herrmann K, Dolan RJ. Neural Correlates of Self-distraction from Anxiety and a Process Model of Cognitive Emotion Regulation. J Cogn Neurosci. 2006;18(8):1266-1276. doi:10.1162/jocn.2006.18.8.1266.

Kaufman L, Rousseeuw P. Reports of the Faculty of Mathematics and Informatics. 87. Delft: Faculty of Mathematics and Informatics; 1987. Clustering by Means of Medoids. Part 3.

Kellogg RT, Chirino CA, Gfeller JD. The Complex Role of Mental Time Travel in Depressive and Anxiety Disorders: An Ensemble Perspective. Front Psychol. 2020;11. doi:10.3389/fpsyg.2020.01465.

Khalsa DS. Stress, Meditation, and Alzheimer's Disease Prevention: Where The Evidence Stands. J Alzheimers Dis. 48(1):1-12. doi:10.3233/JAD-142766.

Kleim B, Graham B, Fihosy S, Stott R, Ehlers A. Reduced Specificity in Episodic Future Thinking in Posttraumatic Stress Disorder. Clin Psychol Sci. 2014;2(2):165-173. doi:10.1177/2167702613495199.

Klema V, Laub A. The singular value decomposition: Its computation and some applications. IEEE Trans Autom Control. 1980;25(2):164-176. doi:10.1109/TAC.1980.1102314.

* cited by examiner

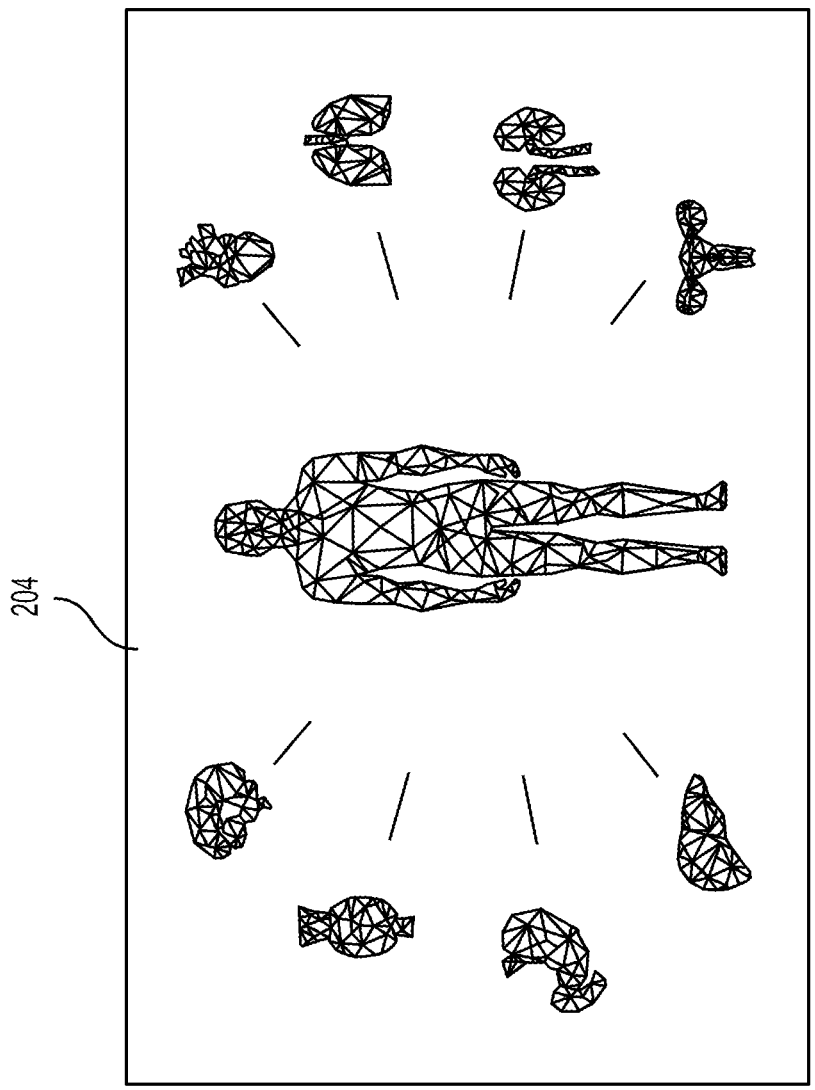
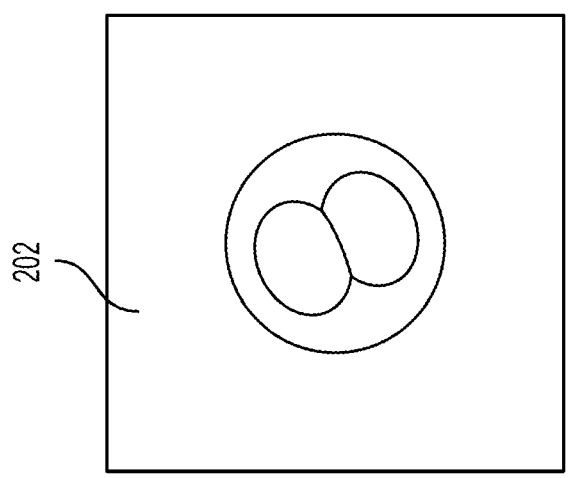
FIG. 2B
FIG. 2A

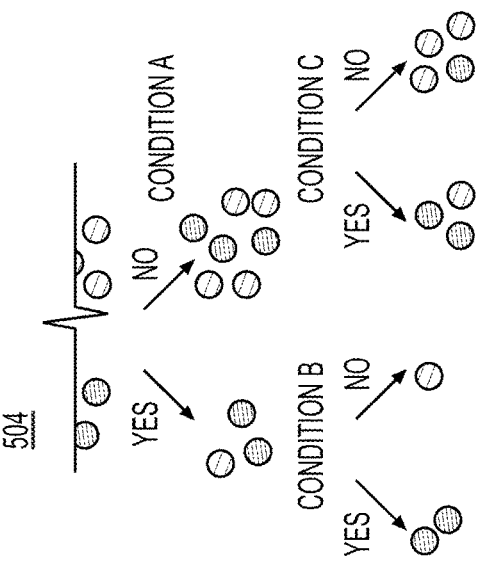
*FIG. 5B*
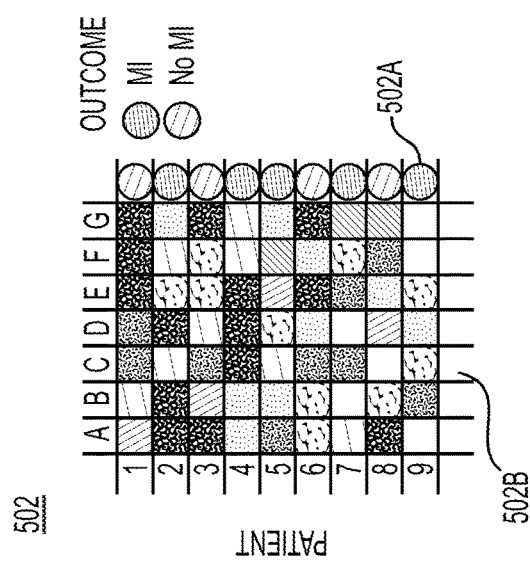
*FIG. 5A*
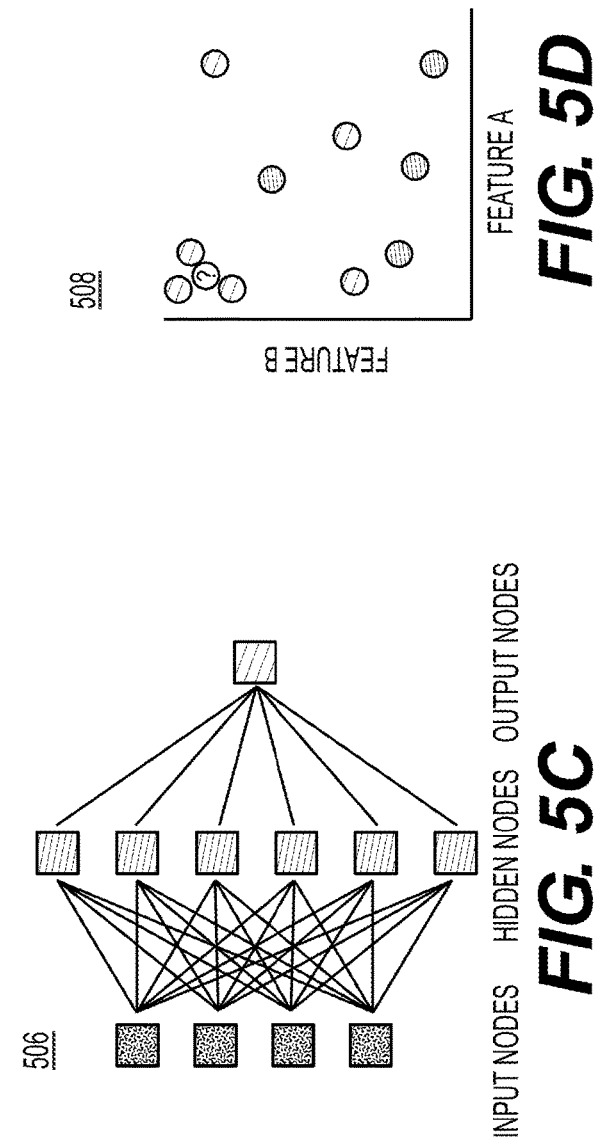
*FIG. 5D*
*FIG. 5C*

OMNICHANNEL THERAPEUTIC PLATFORM

CROSS-REFERENCE TO RELATED APPLICATION

This application claims benefit to U.S. Provisional Patent Application No. 63/108,735, filed Nov. 2, 2020, and U.S. Provisional Patent Application No. 63/122,125, filed Dec. 7, 2020, the entire contents of which are incorporated herein by reference.

TECHNICAL FIELD

Various embodiments of the present disclosure relate generally to a virtual therapy platform, and, more particularly to systems and methods for automatically generating treatments for mental, physical, and other medical conditions using virtual (e.g., digital) content determined via a machine learning platform.

BACKGROUND

Current medical treatments rely on chemically derived medication and medical procedures to treat medical conditions. Despite tremendous advances in medicine, heart disease, cancer, stroke, and Alzheimer's disease remain some of the top causes of death. Current treatments target diseases depending on the respective cells and/or the organs involved. However, there is a need for redefining the factors that limit longevity and aim to alleviate these factors before they contribute to disease states. There is also a need to treat diseases using virtual or digital technology in place of and/or in addition to chemically derived medication.

The present disclosure is directed to addressing one or more of the above-referenced challenges. The background description provided herein is for the purpose of generally presenting the context of the disclosure. Unless otherwise indicated herein, the materials described in this section are not prior art to the claims in this application and are not admitted to be prior art, or suggestions of the prior art, by inclusion in this section.

SUMMARY

In one example, a computer-implemented method for treating a medical condition via a digital therapeutic platform includes receiving one or more user inputs; generating a script at a script generator, based on the one or more user inputs; determining therapeutic digital content by applying the script as an input to a therapeutic machine learning platform; receiving the therapeutic digital content via at least one of a therapeutic content database or a content generator; identifying a user platform to output the therapeutic digital content; modifying the therapeutic digital content for output via the user platform; providing the therapeutic digital content via the user platform; receiving feedback based on user consumption of the therapeutic digital content via the user platform; and adjusting at least one of the script generator or the therapeutic machine learning platform based on the feedback.

In another example, an omnichannel digital therapeutic system includes a processor; a memory; a script generator comprising a script machine learning model, the script generator configured to: receive one or more user inputs; and generate a script based on the one or more user inputs; a therapeutic machine learning platform, the therapeutic machine learning platform configured to: receive the script as an input; determine therapeutic digital content based on the script; and receive the therapeutic digital content from at least one of a therapeutic content database or a content generator; a content rendering and distribution component configured to: identify a user platform to output the therapeutic digital content; modify the therapeutic digital content for output via the user platform; and provide the therapeutic digital content via the user platform, wherein the processor is configured to receive feedback based on user consumption of the specific content via the user platform and further configured to cause adjustment of at least one of the script generator or the therapeutic machine learning platform based on the feedback.

In another example, a method includes receiving one or more user inputs generated based on a user's actions in a metaverse; generating a script at a script generator, based on the one or more user inputs; determining therapeutic digital content by applying the script as an input to a therapeutic machine learning platform; receiving the therapeutic digital content via at least one of a therapeutic content database or a content generator; identifying a user platform to output the therapeutic digital content, the user platform being a metaverse platform; providing the therapeutic digital content via the user platform; receiving feedback based on user consumption of the therapeutic digital content via the user platform; and adjusting at least one of the script generator or the therapeutic machine learning platform based on the feedback.

BRIEF DESCRIPTION OF THE DRAWINGS

The accompanying drawings, which are incorporated in and constitute a part of this specification, illustrate various exemplary embodiments and together with the description, serve to explain the principles of the disclosed embodiments.

FIG. 2A depicts a diagram of a cell, according to techniques presented herein.

FIG. 2B depicts a diagram of organs being interconnected, according to techniques presented herein.

FIG. 5A shows a chart with patient to outcome variance, according to techniques presented herein.

FIGS. 5B-D shows example functions to be applied by a machine learning model, according to techniques presented herein.

DETAILED DESCRIPTION OF EMBODIMENTS

The terminology used below may be interpreted in its broadest reasonable manner, even though it is being used in conjunction with a detailed description of certain specific examples of the present disclosure. Indeed, certain terms may even be emphasized below; however, any terminology intended to be interpreted in any restricted manner will be overtly and specifically defined as such in this Detailed Description section. Both the foregoing general description and the following detailed description are exemplary and explanatory only and are not restrictive of the features, as claimed.

In this disclosure, the term "based on" means "based at least in part on." The singular forms "a," "an," and "the" include plural referents unless the context dictates otherwise. The term "exemplary" is used in the sense of "example" rather than "ideal." The terms "comprises," "comprising," "includes," "including," or other variations thereof, are intended to cover a non-exclusive inclusion such that a process, method, or product that comprises a list of elements does not necessarily include only those elements, but may include other elements not expressly listed or inherent to such a process, method, article, or apparatus. Relative terms, such as, "substantially" and "generally," are used to indicate a possible variation of ±10% of a stated or understood value.

Figure 1:
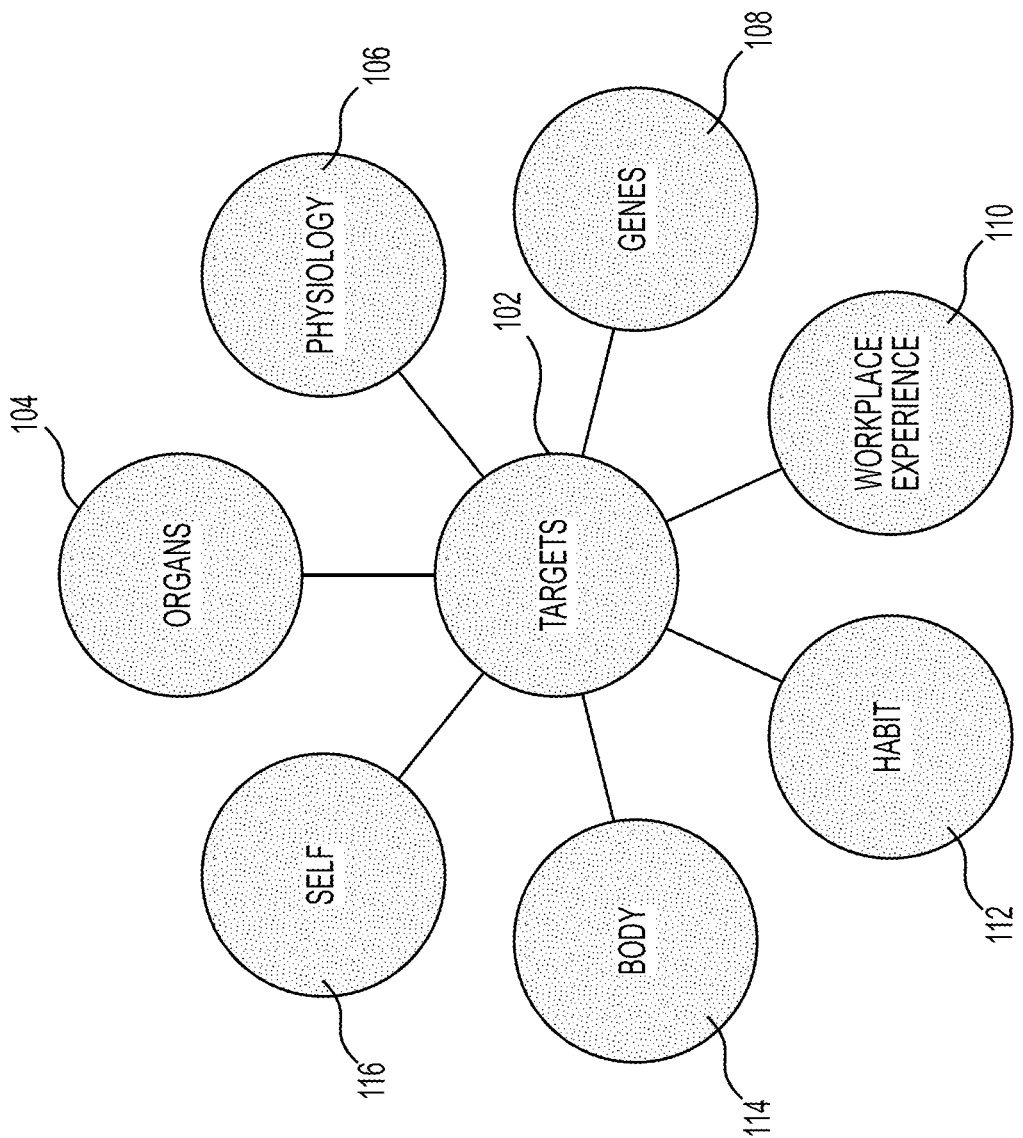
FIG. 1 depicts a diagram showing physiological codes as they relate to targets established for treatments, according to techniques presented herein.

As used herein, a "physiological code" refers to one or more underlying principles that can be used to determine inputs to a machine learning model (e.g., by generating a script that is input into a machine learning model). The underlying principles include, but are not limited to, a principle that body organs is treated as connected, a principle that physiological processes are treated as interconnected, a principle that stress is a common factor that can impact body organs and physiologic processes due to its impact on genes and, thus, is reduced or eliminated, a principle that workplaces can be social incubators of stress and, thus, changing stress at work is beneficial to genes, organs and people, a principle that individuals can be freed from stress-habits, a principle that trauma lives in the body, and that a change in the experiences of the body can result in altering negative impacts of trauma and stress on the body, and a principle that self-scrambling can change how one sees and/or experiences the world. FIG. 1 shows a summary of physiological codes as they relate to targets established for treatments, as disclosed herein. As shown, targets 102 for a machine learning based outcome may be based on one or more organs 104, physiology 106, genes 108, workplace experiences 110, habits 112, body 114, and self 116. Though the physiological codes will be referenced herein in order (e.g., first, second), it will be understood that the order does not imply a ranking or preference, and is provided simply to distinguish the physiological codes from each other.

The disclosed machine learning implementations may be used to identify relationships between user actions (e.g., alcohol use) to responses (e.g., protection from heart disease, stroke likelihood, etc.). The physiological codes discussed herein may be provided directly or indirectly to a machine learning model that increases in complexity as additional codes or information related to one or more codes is applied to the machine learning model. For example, a machine learning model may be configured to add additional layers or weights to its network, based on one or more additional physiological codes, one or more scripts, and/or one or more content options. The additional layers or weights may be added based on one or more relationships that are considered as a result of the physiological codes, scripts, or content. According to implementations, quantum mechanics and quantitative indicators may be used to process data for a given process or as part of a machine learning process.

Implementations disclosed herein may target genes, a default mode network, and/or qualia as they register in the brain. The targeting may allow for treatment or prevention of one or more conditions such as diseases, using virtual content selected for treatment (e.g., to treat genes over one or more content exposures). The targeting may be implemented using a digital therapeutic platform and/or a cyberdelic platform. One or both of these platforms may use an autonomous sensory meridian response (ASMR) or like stimuli to treat or prevent a condition.

According to implementations, one more machine learning processes (e.g., inputs, processing, outputs, etc.) may use data stored on deoxyribonucleic acid (DNA). For example, a machine learning input may be received as DNA or from data stored in DNA. Data may be encoded within DNA by applying an electrical current to open channels in cell walls that receive DNA. Hardware (e.g., storage, processor(s), etc.) that connects to DNA storage facilities may connect to a component disclosed herein (a component of omnichannel therapeutic system 400 of FIG. 4A). On an annual basis, a large portion (e.g., 98%) of an individual's cells may change. Additionally, an individual's brain and body may be in a constant state of flux with a total cellular mass turnover of approximately 80 grams per day. According to an implementation, available or applicable genetic data may be arranged in a matrix of rows and columns. Multiple layers of such matrices may be input into a machine learning model (e.g., using CNN). The output from the model may be a specially formatted that may be provided as an input to an ominchannel therapeutic platform, as disclosed herein.

Based on the first physiological code of organs 104, multiple or all organs may be treated as if they are connected. The organs 104 code considers a humans begin as one cell, as shown by cell 202 in FIG. 2A. From this one cell (e.g., cell 202), the heart, brain, lung, liver and every limb all originate. Throughout life, these organs remain connected through the nervous system and circulatory system. For example, a Gastrointestinal (GI)-brain connection has been discovered, and with it, example considerations are made such as whether Parkinson's disease, a disease historically designated as a brain disease, may actually start in the GI tract. Changes consistent with Parkinson's disease are seen first in the GI tract and then progress to the brain. However, current treatments target specific organs, and in the case of Parkinson's, current treatments primarily target the brain. In some instances, the treatment includes a surgical operation such as by severing the vagus nerve).

Implementations disclosed herein are based on these organs being interconnected, as shown by the diagram 204 in FIG. 2B. Due to these interconnections, implementations are provided such that targeting one organ connected to other organs can affect one or more organs and/or impact one or more diseases. Accordingly, implementations provided herein are directed to using virtual content to provide stimulus via one or more senses, the stimulus positively affecting one or more organs (e.g., stress relief through virtual therapy reducing disease probability).

Based on the second physiological code of physiology 106, all or a subset of all physiological processes should be treated as if they are interconnected. In medicine, disease states are conceptualized as metabolic, immunologic, neoplastic, or endocrine diseases. For instance, diabetes is a metabolic disease. Allergies are immunologic diseases. Cancer of the colon is a neoplastic disease. Thyroid disease is an endocrine disease. Virtual therapy treatments can target these specific processes by exposure to directed content.

Studying diseases reveals that all of these processes may be a factor in each respective disease. Traditional medicine incorporates concepts such as immunometabolism, connecting the immune system and metabolic processes in diabetes. Infections are common in this metabolic disease that involves dysregulation of a key endocrine organ, the pancreas, which also interacts with the brain.

Figure 3A:
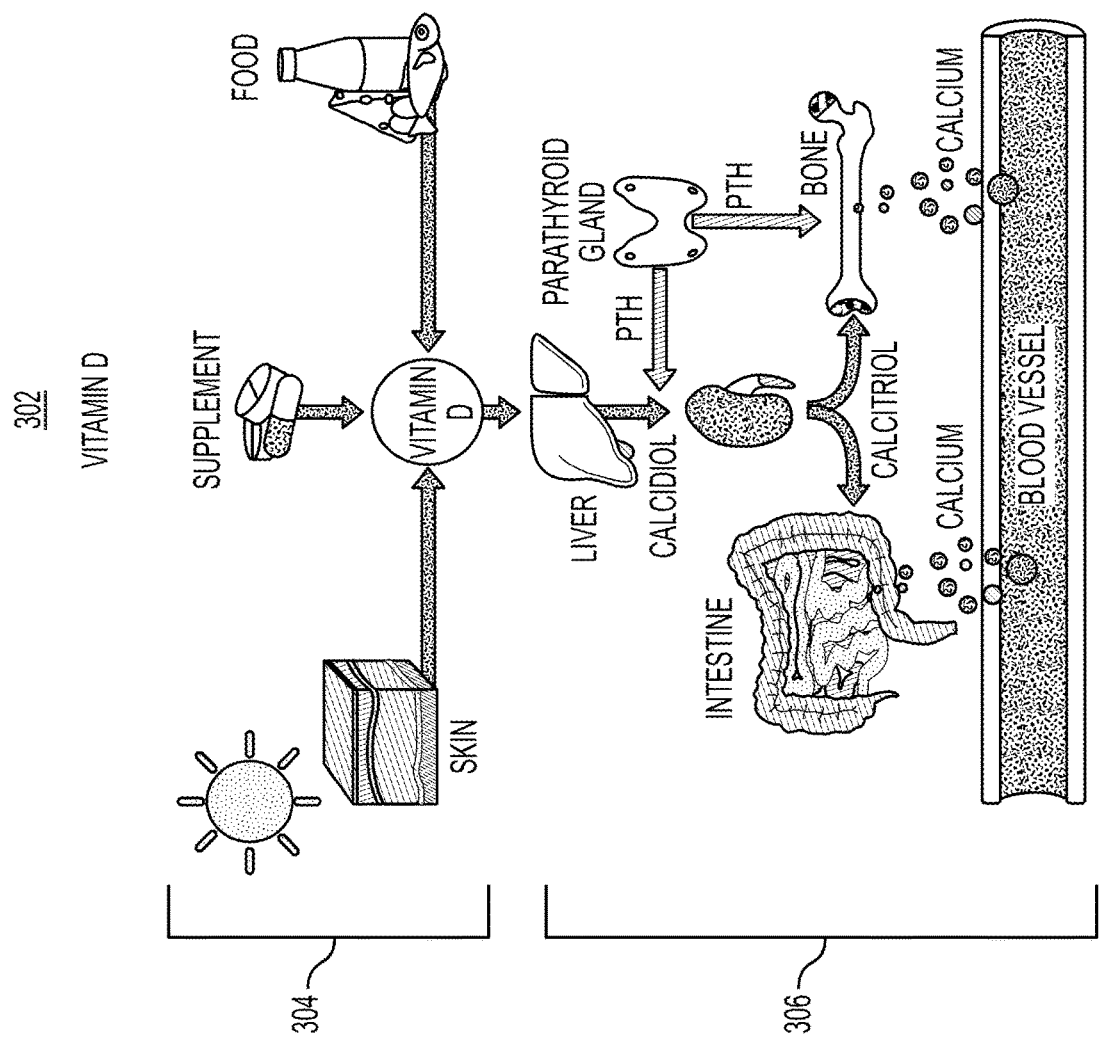
FIG. 3A depicts a diagram showing Vitamin D based inputs, according to techniques presented herein.
Figure 3B:
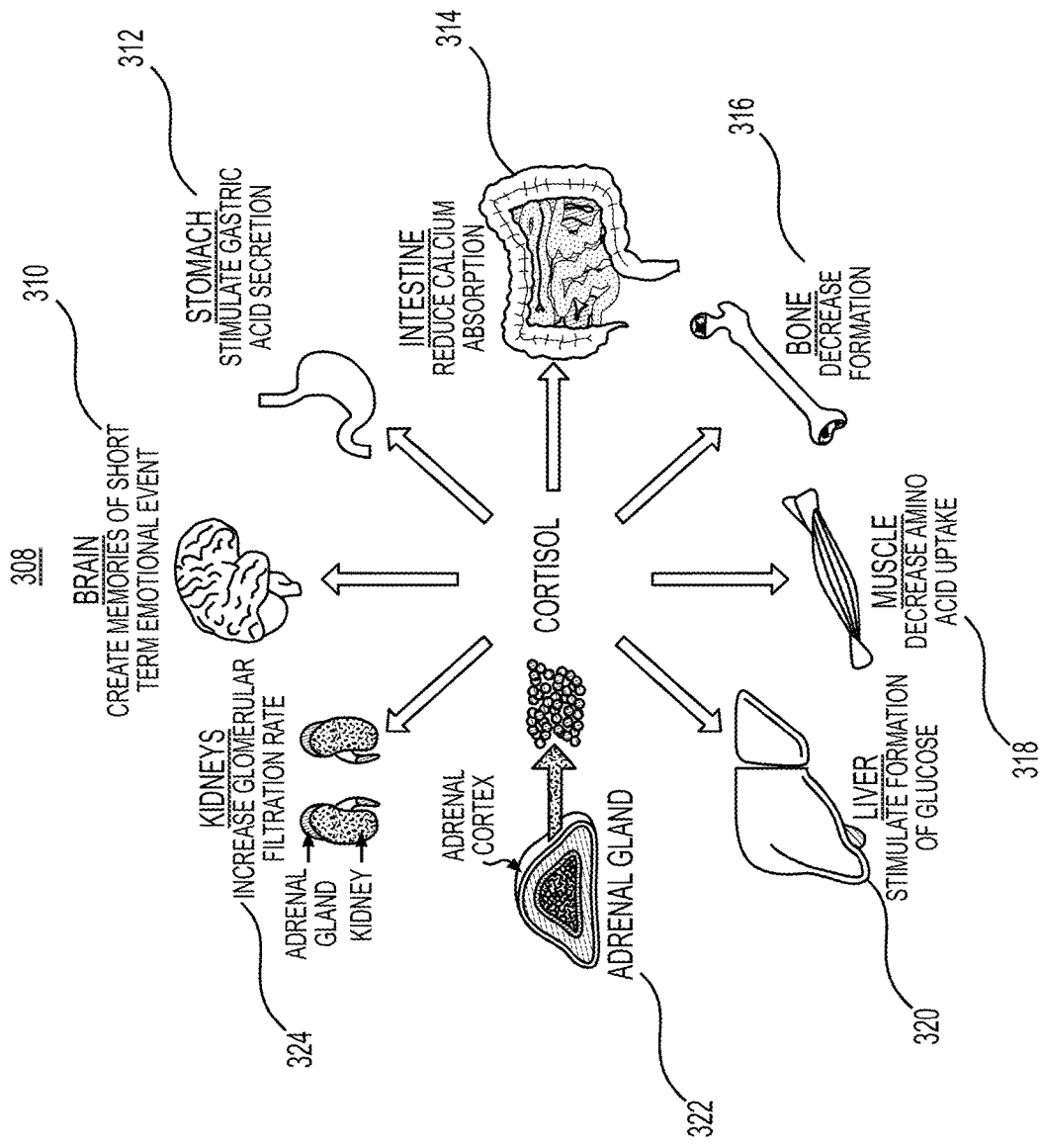
FIG. 3B depicts a diagram showing cortisol's impact on multiple organs and physiologic processes, according to techniques presented herein.

Implementations disclosed herein leverage the finding that multiple or all physiological processes are interconnected. Due to these connections, according to implementations, targeting one process via the targeted virtual therapy disclosed herein affect one or more process and impact one or more diseases. For example, FIG. 3A is a diagram 302 that shows that Vitamin D based inputs at 304 impact multiple organs and physiologic process 306, at the same time. For example, vitamin D inputs 304 including sun exposure to the skin, supplements, and/or food have an effect on multiple organs and body parts including the liver, intestines, blood vessels, bones parathyroid gland, as well as calcidiol, calcium, calcitriol, and parathyroid hormone (PTH) levels. Similarly, FIG. 3B is a diagram 308 that shows that cortisol impacts multiple organs and physiologic process at the same time. These organs and process include the brain 310 (e.g., to create memories of short term emotional events), the stomach 312 (e.g., to stimulate gastric acid secretion), the intestine 314 (e.g., to reduce calcium absorption), bones 316 (e.g., to decrease formation), muscles 318 (e.g., to decrease amino acid uptake), liver 320 (e.g., to stimulate formation of glucose), adrenal gland/adrenal cortex 322, and/or kidneys 324 (e.g., to increase glomerular filtration rates).

Based on the third physiological code of genes 108, stress is a common factor that can impact all organs and all physiologic processes due to its impact on genes and, thus, should be reduced or eliminated for positive health outcomes. Stress can turn gene pathways on or off, which may increase the risk of diseases. According to epigenetics, people develop diseases based on a combination of their genetic and environmental stressors. These environmental stressors may begin early in life and continue throughout life.

Implementations disclosed herein determine targeted digital therapeutic treatments based on epigenetic factors that contribute to disease. Stress is one such factor that can impact genes. Accordingly, targeting stress can affect processes that lead to one or more diseases. For example, FIG. 3B shows the effect of cortisol, a stress based chemical, on different body organs that can develop related diseases. Additionally, implementations of the disclosed subject matter may contribute to methylation and epigenetic changes contributing to mitigate aging and aging-related diseases (e.g., accumulation of histone variants, changes in chromatin accessibility, loss of histones and heterochromatin, aberrant histone modifications, deregulated expression/activity of miRNAs, etc.).

Daily life stress and work-related stress can impact genes such that they turn on disease pathways. In addition, certain genes can confer plasticity, allowing people to adapt more successfully to stress. Stress is also a risk factor for heart disease, cancer, stroke and neurodegenerative diseases such as Alzheimer's disease. Given stress's key role in genetic alterations and pathways for disease, implementations disclosed herein are directed to stress being identified as a key therapeutic target.

Based on the fourth physiological code of workplace experiences 110, life arrangements and/or workplaces can be social incubators of stress and such stress can lead to chronic disease. Accordingly, in order to target the core of one or more diseases, stress at work should be targeted. For example, work related stress has been connected to coronary heart disease, cancer (e.g., prostate cancer), stroke, and Alzheimer's disease. Given stress' key role at work in leading to disease, implementations disclosed herein are directed to stress being a key social context in which to address disease.

As applied herein, "work" may include, but is not limited to, job related activity, labor intensive activity, mentally intensive activity, activity related to financial means, activity related to goals, deadlines, targets, activity conducted based on direction of a superior, activity related to facilitate consumption, activity related providing a service, activity related to generating a good, or the like.

Based on the fifth physiological code of habits 112, to improve health conditions, reduction of stress habits and development habits that promote "gene care" can be implemented. As brushing teeth protects the teeth, "gene care"

habits protects genes and organs. Individuals who are more sensitive to anxiety may develop ongoing anxiety when they are stressed by life events. And early life stress (ELS) may increase the risk of anxiety throughout the life course. Techniques disclosed herein provide gene care solutions and include, for example, digital therapeutic treatment that provides targeted gene care on a case-by-case basis.

Psychiatry targets those activities or conditions that are visible, which results in the targets being symptoms of panic, worry, obsessive compulsive symptoms, depression, or some such manifest anxiety. Stress can turn on habit pathways in the brain, making individuals feel stuck in endless loops of such anxieties. Implementations disclosed herein break these habit loops by redirecting attention and reconfiguring life experience.

Based on the sixth physiological code of body 114, trauma can exist in the body such that when an individual changes the experience of the body, there is chance of altering the negative impact of trauma and stress on the body. Environment, mind, body, and emotional health are inextricably linked to human behavior, practices, wholeness, and thus, wellness. An individual's body is indicative not only of their story but also of the history of the individual and/or their genetics. Implementations disclosed herein are directed to change thinking and history by changing experience of the body and self by using a targeted digital therapeutic.

Implementations of the disclosed subject matter are directed to applying a digital therapeutic to break patterns by changing environmental context and a body's experience.

Based on the seventh physiological code of self 116, self-scrambling can change how one views and experiences the world. How an individual perceives herself may determine how she sees the world. Similarly, how an individual perceives herself and understands others is strongly represented in the activations of a default mode network or circuit in the brain. Accordingly, scrambling this circuit using the digital therapeutic disclosed herein may be beneficial. Implementations disclosed herein provide self-scrambling via a digital therapeutic such that individuals are able to, effectively, rewrite their experiences or views on their experiences. For example, the digital therapeutic may be used to scramble an individual's circuit by dosed exposure to content selected based on the user.

The physiological codes, as shown in FIG. 1, may be used to implement medical treatment interventions to arrest or delay physical disease. As further described herein, a digital therapeutic intervention is provided to arrest or delay physical disease by using, for example, a virtual reality (VR) intervention in a targeted manner.

According to implementations of the disclosed subject matter, interventions (e.g., medical inventions via a digital therapeutic platform), may be designed to address short-term, medium term, and/or long-term care. Such interventions may be transformational more than transitional or transactional. The interventions may allow the interruption of repetition compulsion and self-sabotage (e.g., conscious and unconscious). Gene-care via digital therapeutic may be implemented as a new habit for patients that may benefit from such a habit. High quality longevity may be facilitated by decreasing stress and disrupting this epigenetic determinant of illness. Transformation may be targeted using scripts that relate to, for example, social cues and social influence, both of which may make new habits last (e.g., the gene-care habits discussed herein).

Figure 3C:
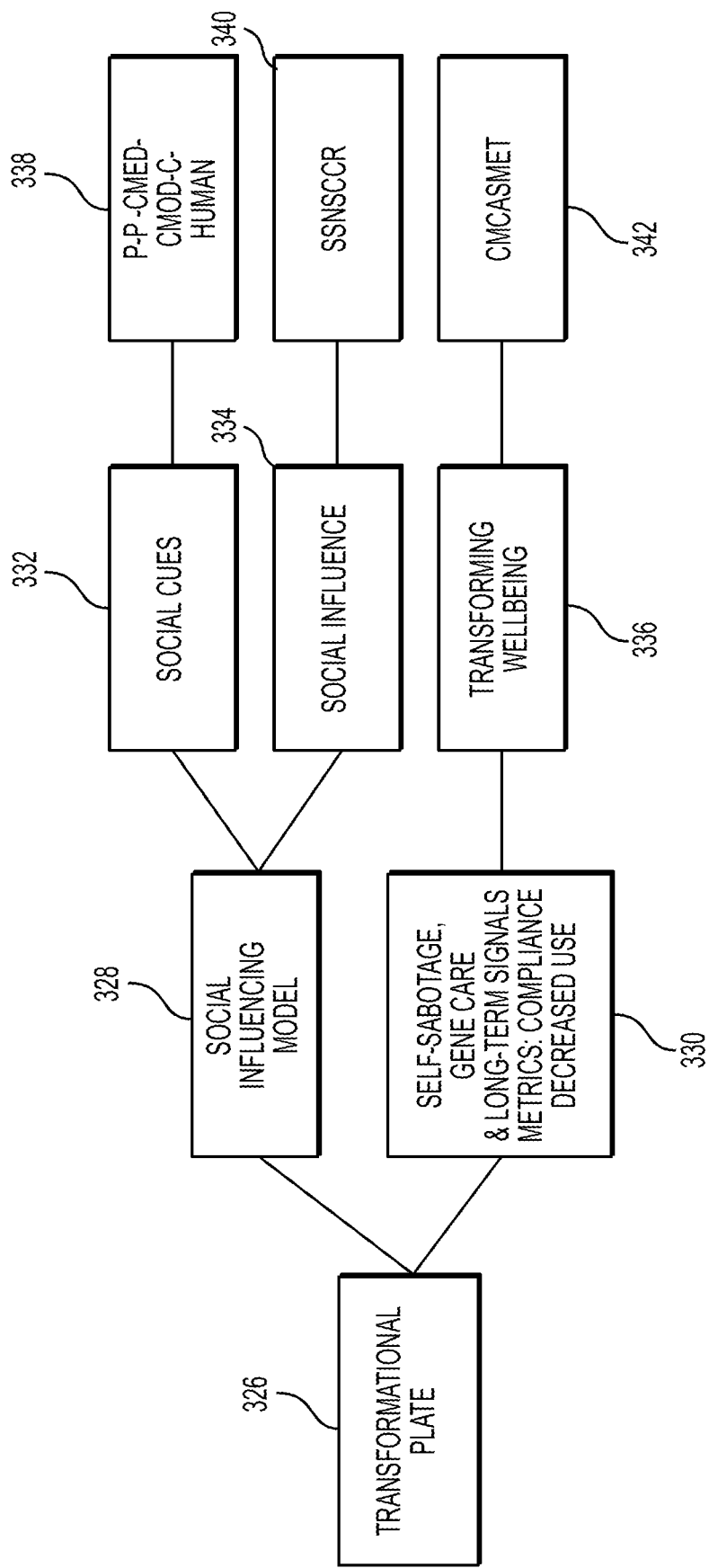
FIG. 3C depicts a diagram showing a transformational platform, according to techniques presented herein.

As shown in FIG. 3C, a transformational platform 326 with interventions may be implemented to address short-term, medium term and/or long-term care. As shown, transformational platform 326 may include a social influencing model 328 and a self-sabotage, gene care and/or long-term signals model 330 with metrics for compliance or decreased use. The social influencing model may leverage social cues 332 and social influence 334.

Social cues 332 may include physical cues such as those based on a face, eyes, body, movement, etc. Additionally, input items to direct social cues may be provided such as goggles (e.g., waterproof googles with leads). Social cues 332 may include psychological considerations (e.g., personality, similarity, feelings). A software fashion brand with attributes that change based on environmental inputs (e.g., with the seasons (flow, glow, snow, grow)) may be used as inputs. Social cues 332 may be implemented using language (e.g., spoken language, praise, language recognition). For example, a quote from a quote databank or based on one more physiological code may be provided along with virtual content. Social cues 332 may be provided via social dynamics (e.g., dialogues, reciprocity, etc.). For example, virtual hugs such as via Roblox™ and/or VR chat may be implemented. Social cues 332 may be provided via social roles (e.g., authority, doctor, teacher, etc.). A social cue model may be implemented based on individual specific interactions/questions (e.g., "Have you experienced the virtual therapeutic platform today? Why don't you experience the virtual therapeutic platform?", etc.). They may computer mediated (e.g., the virtual therapeutic platform word cloud (Team Temperament Temperature) or "Add an element" cloud (What you wish you saw) followed by "Dreams come true") by the virtual therapeutic platform, where such elements are added.

Social cues 332 may be used for computer moderation of the digital therapeutic such that, for example, a computer may automatically shut off at the maximum dose or a check-in may occur to indicate "care" such that a user belong to a caring community. The virtual therapeutic platform disclosed herein may be integrated using a smart home, smart speaker, virtual assistant, calendar, or like device, software or firmware such as, for example, Alexa® or iCal®. As shown in FIG. 3C, social cue 332 uses are abbreviated as P-P, CMED, CMOD, CHuman 338, or the like. Social cues 332 may be provided for training a machine learning model or an individual's social cues may be used as inputs to a machine learning model to determine the applicable content and/or dosage or treatment for an individual.

Referring to FIG. 3C's social influence 334 component, social learning may be used (e.g., a video of how the device and/or software is used, show others using the software in real time) for inputs or treatment. Social comparisons may be used (e.g., a number of active users, survey scores (e.g., Human scores) across a geographical landscape, etc.) for inputs or treatment. Normative influence may be used (e.g., average user number, interaction, etc.) for inputs or treatment. Social facilitation may be used (e.g., Individual compared to team use) for inputs or treatment. Cooperation may be used (e.g., individuals use the virtual therapeutic platform prior to a difficult conversation and report positive results) for inputs or treatment. Competition may be used (e.g., a race for genetic protection) for inputs or treatment. Recognition may be used (e.g., top user of the month) for inputs or treatment. As shown in FIG. 3C, these social interaction uses are abbreviated as SSNSCCR 340.

Figure 3D:
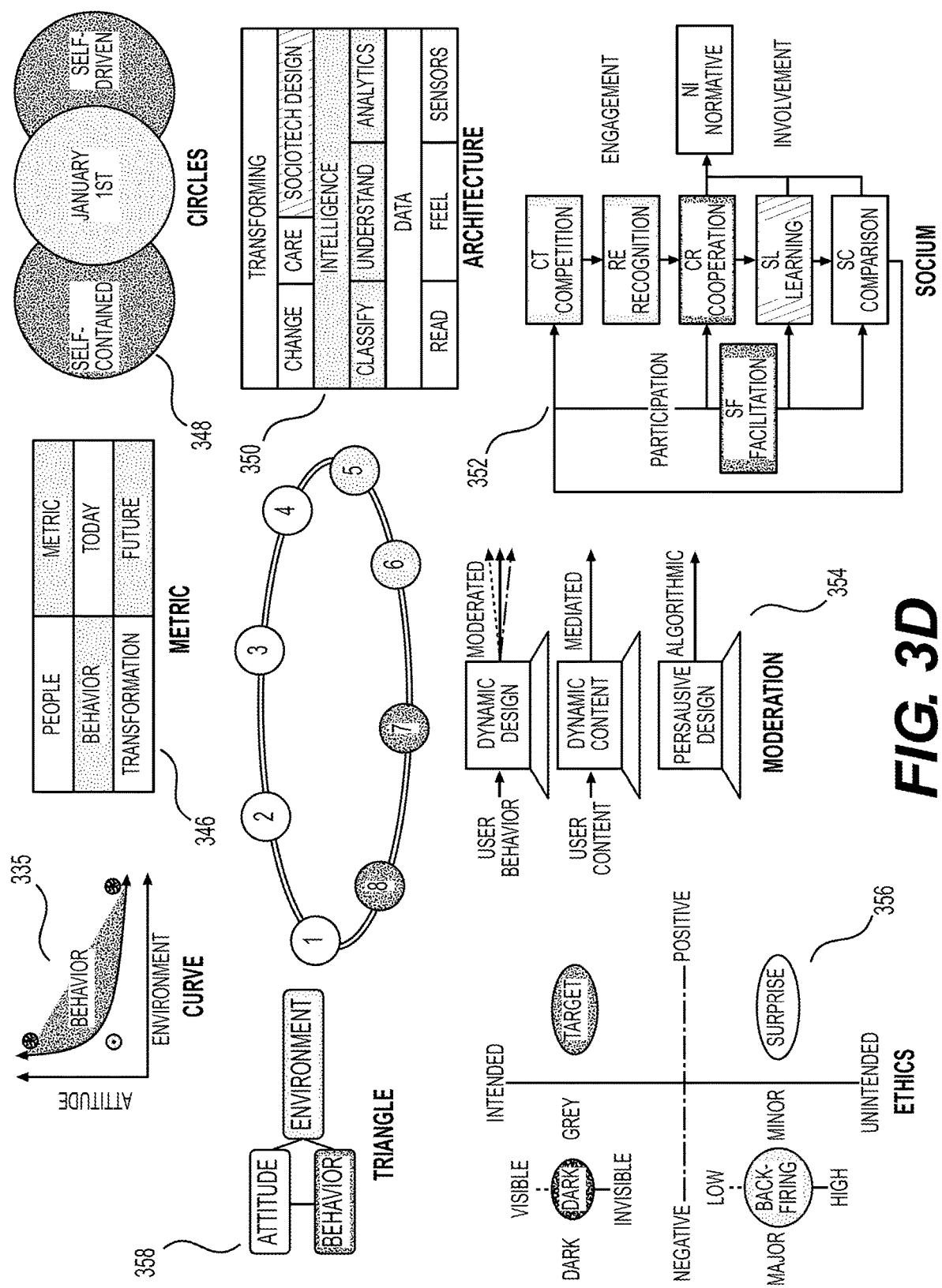
FIG. 3D depicts a diagram for transformation of wellbeing, according to techniques presented herein.

As shown in FIG. 3D, a transformation for wellbeing using a digital therapeutic may be implemented using a curve 335 (e.g., a relationship between attitude, environment and related behavior), metric 346 (e.g., factoring people, metrics, behavior, day, transformation, and/or future), circles 348 (e.g., self-contained and/or self-driven based on date), architecture 350 (e.g., for a transformation based on change, care, sociotechnological design, intelligence based on classification, understanding, and analytics, and/or data based on reading, feeling, sensors, etc.), socium 352 (e.g., based on participation, engagement, and/or involvement), moderation 354 (e.g., based on user behavior, user content, dynamic design, dynamic content, persuasive design, and corresponding moderation or algorithm), ethics 356 (e.g., based on positive/negative and intended/unintended factors), and/or triangle 358 (e.g., attitude, heavier, and/or environment) factors for improving wellbeing using a digital therapeutic. As shown in FIG. 3C, these factors are abbreviated as CMCASMET 342.

Medical disease can be arrested or delayed by active interventions, in context, to reduce stress that can turn on disease mechanisms including, for example, cardiovascular disease, cancer, stroke, and/or neurodegenerative diseases. Abnormalities in brain anatomy, physiology, chemistry, and electricity underlie many medical disorders. Novel therapeutic agents have included agents that target these brain abnormalities. Such novel therapeutic agents include drugs, electrical therapies, and brain-based psychotherapies.

Implementations of the disclosed subject matter are directed a digital therapeutic that may identify one or more paradigms to generate a script for a given user. The script may be provided to a machine learning platform and the machine learning platform may identify content to present to a user based on the script and/or one or more other inputs. The content may include passive interventions (e.g., consumable content), gaming (e.g., interactive content), social (e.g., social media) integrated content, and/or the like.

A therapeutic platform is disclosed herein to provide an adaptive and personalized digital approach to stress reduction therapy. As an example implementation, at the start of a session, a user may provide data regarding a self-assessment survey, and additional user inputs and system integrations including data such as, attributes for the platforms disclosed in FIG. 1, the social cues disclosed in FIG. 3C, the social influence factors disclosed in FIG. 3C, demographic data, time/date, biometric data, electroencephalogram (EEG), heart rate, average heart rate, heart rate viability (HRV), resting heart rate (RHR), respiratory rate, pulse, eye tracking, pupil dilation, facial recognition, pulse oxygen, air quality, user temperature, magnetic resonance imaging (MRI) data, family history of risks, and genetic history, genetic risks, digital body, digital body scans, sleep patterns (e.g., rapid eye movement (REM), non-rapid eye movement (nREM), deep sleep), taste attributes, smell attributes, hormone levels, or the like or a combination thereof.

For example, the targets provided in FIG. 1 may be used as inputs. More specifically, the inputs may be based on one or more of a patient's organs, physiology, and/or body including, but not limited to, brain based inputs (e.g., EEG, functional MRI (fMRI), positron emission tomography (PET), single-photon emission computerized tomography (SPECT), baseline MRI gray matter and white matter volumes and blood flow, brain entropy, MUSE EEG pattern, etc.), eye attributes (e.g., pupil diameter), ears (e.g., specific sound frequency), mouth attributes (e.g., taste preferences), smell attributes (e.g., preferences as operationalized by olfactory VR (OVR) technology), blood vessels (e.g., carotid doppler findings, pulse rate, HVR), heart (e.g., EKG, echocardiogram, troponin, creatinine kinase, CK-MB, myoglobin, Apple® health kit integration, HP OMNICEPT SDK), lungs, (e.g., chest X-Ray, pulmonary perfusion tests), blood findings (e.g., TSH, T3, T4, CBC, white cell count, platelets, MCV, MCHC, PTH, cholesterol, glucose), liver (e.g., LFTS (AST, ALT, Alk phos), albumin, globulin, PT/PTT, liver ultrasound), gastrointestinal tract (e.g., gastrointestinal tract bacterial composition), hypothalamic pituitary hormones (e.g., GnRH, FH, LH, ACTH), adrenal (e.g., cortisol, aldosterone), renal (e.g., BUN/Creatinine), electrolytes (e.g., Na+, K+, Cl−, HCO3−), immune markers (e.g., CD4, IGs, T-cell count and differential count, B cells), tumor markers, skin conductance, psychological diagnostic criteria met (e.g., panic disorder, GAD, PTSD, coronaphobia depression, selective mutism, agoraphobia, bipolar disorder, ADHD, OCD, social anxiety, specific phobia, trans diagnostic factors), or the like or a combination thereof.

The inputs may be based on date/day/time, family history, genetic information, HUMAN survey (e.g., a developed survey), results of a Patient-Reported Outcomes Measurement Information System (PROMIS) short-form anxiety inventory, results of a State-Trait Anxiety Inventory (STAI-Y1), results of brief resilience questionnaire, results of PROMIS-Cognitive function short form questionnaire, results of a PROMIS Self-efficacy Scale (Short-form), results of a Generalized Anxiety Disorder 2 (GAD-2) questionnaire, results of a proprietary mental reset questionnaire, natural language processing, facial analytics, heart rate variability, MUSE™ EEG pattern, skin conductance, a number of steps taken, heart rate, cholesterol, cortisol, electrocardiogram (EKG), echocardiogram, baseline MRI gray matter and white matter volumes and blood flow, brain entropy measurements, Apple® health kit integration, genetic inputs, genetic testing, PCR results, serotonin transporter genotype, workplace experience, burnout scores, engagement scores, fatigue scores, possibility index scores, habits, smoking history, alcoholism, drug use/abuse, poor dietary habits, exercise frequency, self, motivation, anxiety scores e.g. STAI-Y1, PROMIS, HAM-A, depression (e.g., HAM-D), BPRS, YMRS, existential anxiety ratings, insomnia, results of brief resilience questionnaire, results of PROMIS-Cognitive function short form questionnaire, results of the PROMIS Self-efficacy Scale (Short-form), demographics, corporate syndromes, impostor syndrome, summit syndrome, to build resilience, to increase creativity, to increase agility, heart disease, medical disorders, cancer, neurodegenerative disease, stroke, endocrine diseases, metabolic diseases, cardiovascular disease, or the like or a combination thereof.

According to an implementation, a machine learning model may receive various inputs for a given user and/or users of the therapeutic platform and may determine how the inputs relate to clinical symptoms, demographics, biometrics, genetics, brain/physiological responses with related treatment responses on a variety of indicators such as Generalized Anxiety Disorder 2-item (GAD-2), State-Trait Anxiety Inventory (STAI) forms Y1 and/or Y2, Patient-Reported Outcomes Measurement Information System (PROMIS), or the like. One or more statistically significant correlations may be determined based on one or more correlations executed through regression analyses, quantum mechanics, and symbolic indicators. The one or more statistically significant correlations may be integrated with one or more machine learning models disclosed herein. Inputs provided to the machine learning model may be used to output recommendations based at least in part on the correlations. The machine learning model may apply clinical data, biometrics, genetics, one or more relationships, brain/physiologic responses, demographics, etc. to provide the output recommendations.

According to an implementation, user inputs may include user characteristics that may be provided by the user or may be determined based on data from user accounts. User accounts may include user social media accounts, transaction accounts, travel accounts or the like. According to an example, a user may provide access to a user social media account. Based on the user provided access, an evaluation of the user's images, preferences, and/or activities may be conducted. Based on the evaluation, a user profile may be generated and applied as a user input. As a more specific example, the evaluation may determine that the user has a strong preference for mountain hikes based on images shared by the user during hikes. Another determination may be made that the user has not posted an image of a mountain hike for an extended duration of time. Accordingly, the user profile may include that the user favors mountain hikes and the user has not conducted a mountain hike for an extended duration of time. According to an implementation, user information and user content (e.g., images, vides, etc.) may be archived for use by the therapeutic platform for use during treatment. The user information and/or user content may be provided to a script generator to generate a script provided to a machine learning model, as further discussed herein.

According to an implementation, user inputs may include a digital representation of a user's body (e.g., a digital body). The digital representation of the user's body may be generated using one or more scans that capture the physical components of the user's body such that the user's body structures can be processed into computer readable formats. The digital representation of the user's body may also include organ characteristic (e.g., RHR, brain activity, etc.) as well as movement characteristics (e.g., using biological motion sensors). The digital representation of a user's body may be used as an input to the therapeutic platform disclosed herein such that a machine learning algorithm uses the digital representation when generating a script or providing content to present to a user. Additionally, the digital representation may be used when determining feedback from a user, as further disclosed herein.

Based on one or more inputs, a paradigm may be selected to target a specific brain anxiety circuit or a combination of specific circuits. The paradigm may be selected using a script machine learning model at a script generator. The script machine learning model may first apply a decision tree that is updated based on previous users' pre-and-post content inputs/feedback and/or a given individual user's historical usage. During a digital therapeutic session, a real time monitor may track user biometric data. Following the digital therapeutic session, the user may be presented with a post self-assessment and the biometrics data and feedback may be stored. In addition, the session duration may be captured and stored (e.g., at a local or remote server) and measured against the biometrics data pre-and-post the session to determine if the digital therapy dosage was accurate. Dosage of a digital therapeutic session may include session duration, light intensity, sound intensity, and other characteristics of light and sound. The dosage may also include an amount of virtual or augmented reality provided and/or interacted with as well as a percent of any holographic content provided and/or interacted with. Based on survey feedback, biometric data, therapy dosage, and the like, the algorithm may decide if the a given digital therapeutic and/or dosage was best suited for the user. Such analysis may be applied by one or users to provide a more accurate script and/or content selection for a new user, subsequent users, or a subsequent session for the same user.

Based on input signals, the system may determine one or more user devices to present additional content. The user devices may include but are not limited to a web platform (e.g., a web application, web 3.0 application, etc.), VR application (e.g., via a virtual head mount device), an augmented reality (AR) application (e.g., via a mobile device), a holographic application via any devices such as glasses, contacts, projectors, etc., or the like to provide a dosage of a digital therapeutic session to effect the brain anxiety circuit to reduce stress. One and/or more techniques disclosed herein may be implemented using Connected TV, over the top (OTT) television, internet of things (IoT) devices, web based applications, 5g, 6g, podcasts, digital radio, windows mixed reality headset (WMR), mixed reality apps, home automation/smart home devices (e.g., Google® home enabled devices, Alexa® enabled devices, etc.), or the like.

According to an implementation, the digital therapeutic platform may be used to deliver mixed reality, AR, and/or VR content to individuals to prepare for or to cope with space travel (e.g., to the moon, to one or more planets, or to any outer atmosphere body including a space station or the like). Digital therapeutics used for this implementation may be paired with and/or implemented with geodesic domes, flotation tank-like experiences, sacred geometry, bubbles (e.g., VR images inside bubbles and processes that relate to magic such as sudden appearance, disappearance, and manifestation, etc.) as well as storytelling narratives attached to multisensory experiences, memories, presence, or futuristic ideas.

Figure 4A:
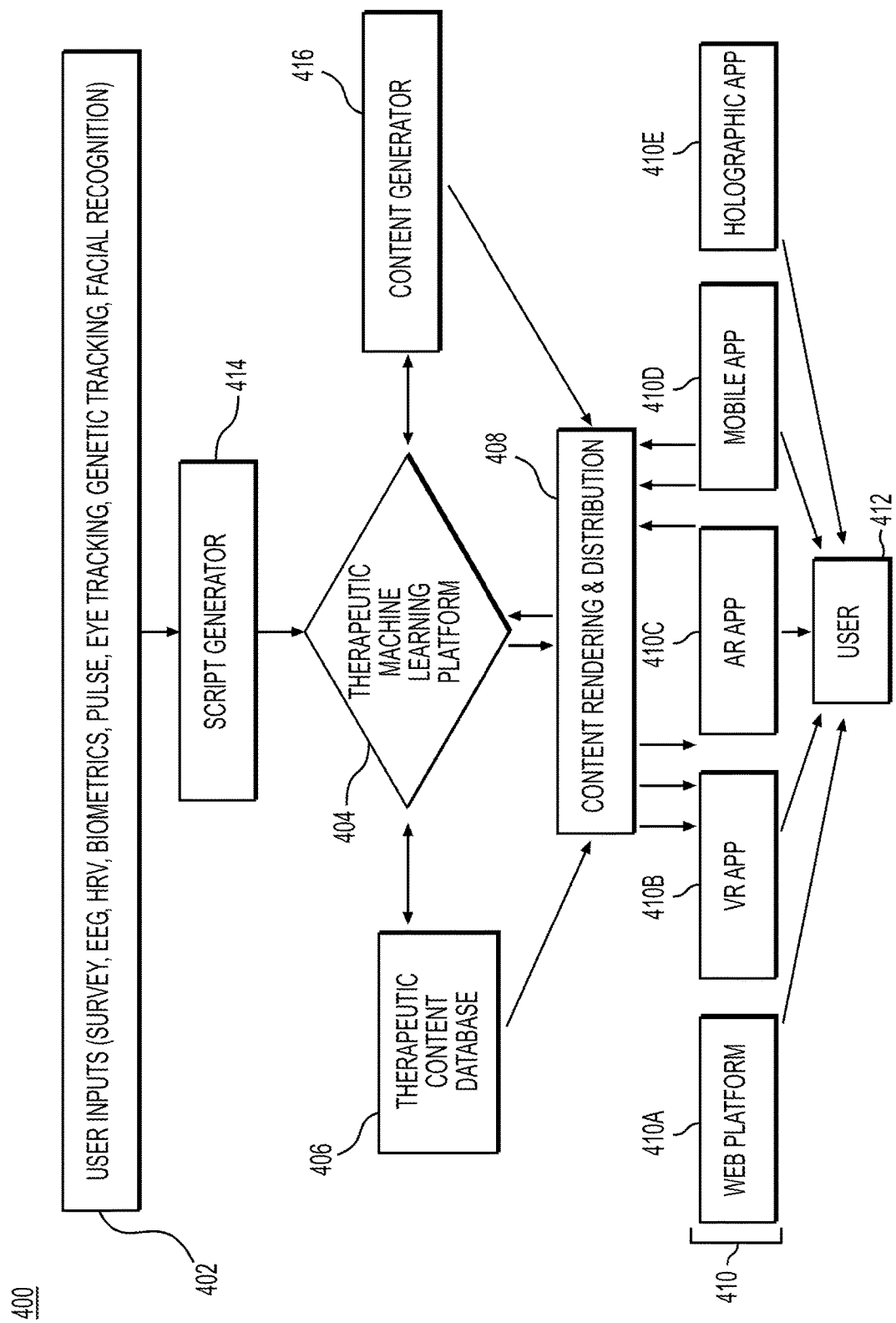
FIG. 4A shows an omnichannel therapeutic platform, according to techniques presented herein.

FIG. 4A shows an omnichannel therapeutic system 400 that may be used to identify a patient condition based on the user inputs at 402, determine an applicable script based on the user inputs via a script generator 414, identify applicable content using a therapeutic machine learning platform 404, receive therapeutic content from therapeutic content database 406 and/or content generator 416, based on the user inputs 402 and the applicable script, prepare the content for rendering and distribution using content rendering and distribution component 408, and provide the content to an applicable user platform 410 (e.g., via platforms 410A-E) such that user 412 can access the user platform 410. Feedback from user 412's exposure to the content and/or its resulting effects may be populated through the therapeutic platform. For example, a duration of exposure to the provided content, a user provided answer, and/or a test result may be provided back to script generator 414 and/or therapeutic machine learning platform 404. The feedback maybe used to adjust weights, layers, and/or other components of a script machine learning model and/or therapeutic machine learning model to re-calibrate future scripts, content, dosages, or the like.

The feedback may be used to modify a machine learning model layer, add or remove a machine learning model layer, or modify a weight of a machine learning model. The modification may be based on determining an extent of modification, a type of modification, or the like. The modification may be implemented by updating a code that is compiled to run the machine learning model. A specific modification may be determined based on one or machine learning algorithm disclosed herein.

User inputs 402 of FIG. 4A may be any applicable inputs that are generated by or based on user 412. User inputs 402 may include survey data, user data, biometric data, test results, or the like or a combination thereof. User inputs 402 may include platform attributes of FIG. 1 as they relate to user 412, social cues 332 of FIG. 3C, the social influence 334 or transforming wellbeing 336 of FIG. 3C. User inputs 402 may be provided based on input via a user device, third party provision of one or more results, sensor data, image data, or the like. User 412 may grant permission for the digital therapeutic platform of FIG. 4A to receive one or more user inputs 402. User inputs 402 may be provided periodically, may be pushed upon user 412 or system requests, may be pulled by the system based on system determined thresholds, or may be constantly sensed or provided (e.g., by one or more sensors).

User inputs 402 provided by one or more sensors may be via patch sensors, sensors in contact with the body, wearable devices (e.g., smart watch with integrated sensors, glucose monitoring device (e.g., continuous glucose monitoring (CGM) device), smart glasses, etc.), sensors functioning as wearable devices, sensors inserted into the body, or the like or a combination thereof. The one or more sensors may be external to user 412 (e.g., a gaze tracking camera). The one or more sensors may connect to the internet via a wired or wireless connection such that the sensed data is transmitted to a cloud server and provided to the VR platform from the cloud server. The one or more sensors may be batter powered, use near field technology, radio frequency technology, or the like. The one or more sensors may transmit data over any applicable network (e.g., electronic network 1725, discussed herein), or may transmit data over a wired connection.

Script generator 414 may include a script machine learning model or algorithm to determine a script (e.g., based on one or more paradigms) based on user inputs 402 and/or one or more additional inputs as disclosed herein. Script generator 414 may use machine learning to generate a script to improve user health and/or mitigate disease based on user inputs 402. Script generator 414 may identify one or more themes (e.g., paradigms) that apply to user 412 based on user inputs 402. A paradigm used by script generator 414 may be one of seven paradigms disclosed herein (i.e., calm, focus, distraction, somatic, escape, possibility, sublime/awe) or one or more other paradigms that have associated content in the therapeutic content database or that a therapeutic machine learning model may use to generate content. The script machine learning model or algorithm may provide the determined script to the therapeutic machine learning platform 404 and the therapeutic machine learning platform 404 may identify content for rendering and distribution using content rendering and distribution component 408.

Therapeutic machine learning platform 404 may identify the optimal content for user 412 based on the script and/or one or more user inputs, historical user performance, historical user group performance (e.g., of a cohort of users with one or more overlapping or like characteristics to user 412). Therapeutic machine learning platform 404 may, for example, receive an input from therapeutic content database 406 and the therapeutic content database 406 may provide one or more content based on the determined script. Alternatively, therapeutic machine learning platform 404 may activate a GAN engine to generate all or part of content based on the script. According to an implementation, the therapeutic content database 406 may be part of or may include the therapeutic machine learning platform 404.

According to an implementation, therapeutic machine learning platform 404 may receive a script from script generator 414 and identify a subset of the available content at therapeutic content database 406, associated with that script. The identified subset of content may be content based on the script and/or one or more user inputs 402 applicable to user 412. therapeutic machine learning platform 404 may determine that the identified content and an applicable dose is most likely to treat user 412 (e.g., for stress) or to mitigate future stress or disease.

Therapeutic content database 406 may include a variety of content including, but not limited to, audio content, video content, digital content, content related to a plurality of scripts and the content may include 4K digital videos, 8K digital videos, 360 degree immersive videos, volumetric video, 360 degree interactive videos, 180 degree immersive videos, 180 degree interactive videos, generative music, music at natural frequencies (e.g., 432 GHz, 396 GHz, 417 GHz, 4.33 GHz, 915 MHz, 2.4 GHz, 5 GHz, etc.), or the like or a combination thereof.

Content generator 416 may generate content (e.g., audio content, video content, digital content, content related to a plurality of scripts and the content may include 4K digital videos, 8K digital videos, 360 degree immersive videos, volumetric video, 360 degree interactive videos, 180 degree immersive videos, 180 degree interactive videos, generative music, music at natural frequencies etc.). Content generator 416 may generate the content based on requirements provided by therapeutic machine learning platform 404, based on content provided by therapeutic content database 406, or the like.

Either therapeutic content database 406, content generator 416, or therapeutic machine learning platform 404, or a combination of the same, may output consumable content (e.g., a subset of the available content at therapeutic content database 406 or generated content from content generator 416), associated with the script. The consumable content may be determined based on the user inputs at 402, script generated at script generator 414, historical content provided to user 412, historical content provided to a plurality of users (e.g., a cohort), feedback from user 412 or the plurality of users, a user device associated with user 412, an application associated with user 412, a user preference, a user response value, and/or the like.

The consumable content may be provided to a content rendering and distribution component at 408. Content rendering and distribution component 408 may be a physical server, database, or other component connected to a network or may be a network component that is connected to one or more user platforms. Content rendering and distribution component 408 may prepare a consumable content item for delivery to the user via a user platform. For example, content rendering and distribution component 408 may receive a content item and may modify its output by adjusting its refresh rate, dimensionality (e.g., two dimensional, three-dimensional, VR, holographic), colors, aspect ratio, size, quality, attributes for presentation for VR, attributes for presentation for AR, or the like or a combination thereof such that the content is consumable by user 412 via an applicable user platform 410. Content rendering and distribution component 408 may detect user platform 410 (e.g., web platform 410A, VR application 410B, AR application 410C, mobile application 410D, holographic application 410E, wearable device application, etc.) and may modify the content based on the user platform, to generate consumable content. According to an implementation, user platform 410 may include a digital pill. A digital pill may be implemented using VR, AR, or XR and may provide user 412 a sensation of picking up and/or swallowing a pill. The digital pill may use haptic technology to provide the picking up and/or swallowing sensation. Additionally, or alternatively, content rendering and distribution component 408 may detect upload and/or download capabilities of user platform 410 and may modify the content based on the same.

A dosing amount of digital therapeutic content may be determined based on user inputs 402 and/or feedback from previous sessions. The dosing amount may be determined along with the selection of the consumable content itself and may be an amount selected to optimize the treatment of user 412. The dosage amount may be determined by script generator 414, therapeutic machine learning platform 404, or a combination thereof. As an example, a determination of a user state may be determined based on user inputs 402 including a user provided survey and user biometrics. Based on the determination of the user state and the biometrics, script generator 414 may determine a script and a dosage range. Therapeutic machine learning platform 404 may select content from the therapeutic content database at 406. A specific dosage of the content may also be determined by therapeutic machine learning platform 404 based on user inputs 402 and past user dosages, such that, for example, a consumable content being consumed for a total of eight minutes may be designated as the optimal dose of that content and user 412 combination. Accordingly, the consumable content may be provided to user 412 via a user platform 410 for a duration of eight minutes.

User platform 410 (e.g., platforms 410A-410E) may receive the consumable content and may provide the consumable content to user at 412. User platform 410 may be include one or more processors that, based on being configured by an application or other software, configures the user platform to provide the consumable content for user 412 consumption. User 412 may be able to control the display or output of the consumable content via user platform 410 such as by playing, stopping, pausing, adjusting, or otherwise interacting with the consumable content via the user platform.

According to an implementation, user platform 410 may be selected by the content rendering and distribution component 408 and/or therapeutic machine learning platform 404, based on the user inputs 402. For example, content rendering and distribution component 408 may determine that user 412 has access to a web platform 410A, a VR application 410B, an AR application 410C and a mobile application 410D. Based on this determination and on receiving a user provided survey and user biometric data, therapeutic machine learning platform 404 may determine that the optimal user platform from for providing a given consumable content to user 412, based on use 412's conditions and/or attributes, is the available AR application 410D. Accordingly, content rendering and distribution component 408 may prepare the consumable content for output via AR application 410D.

Figure 4B:
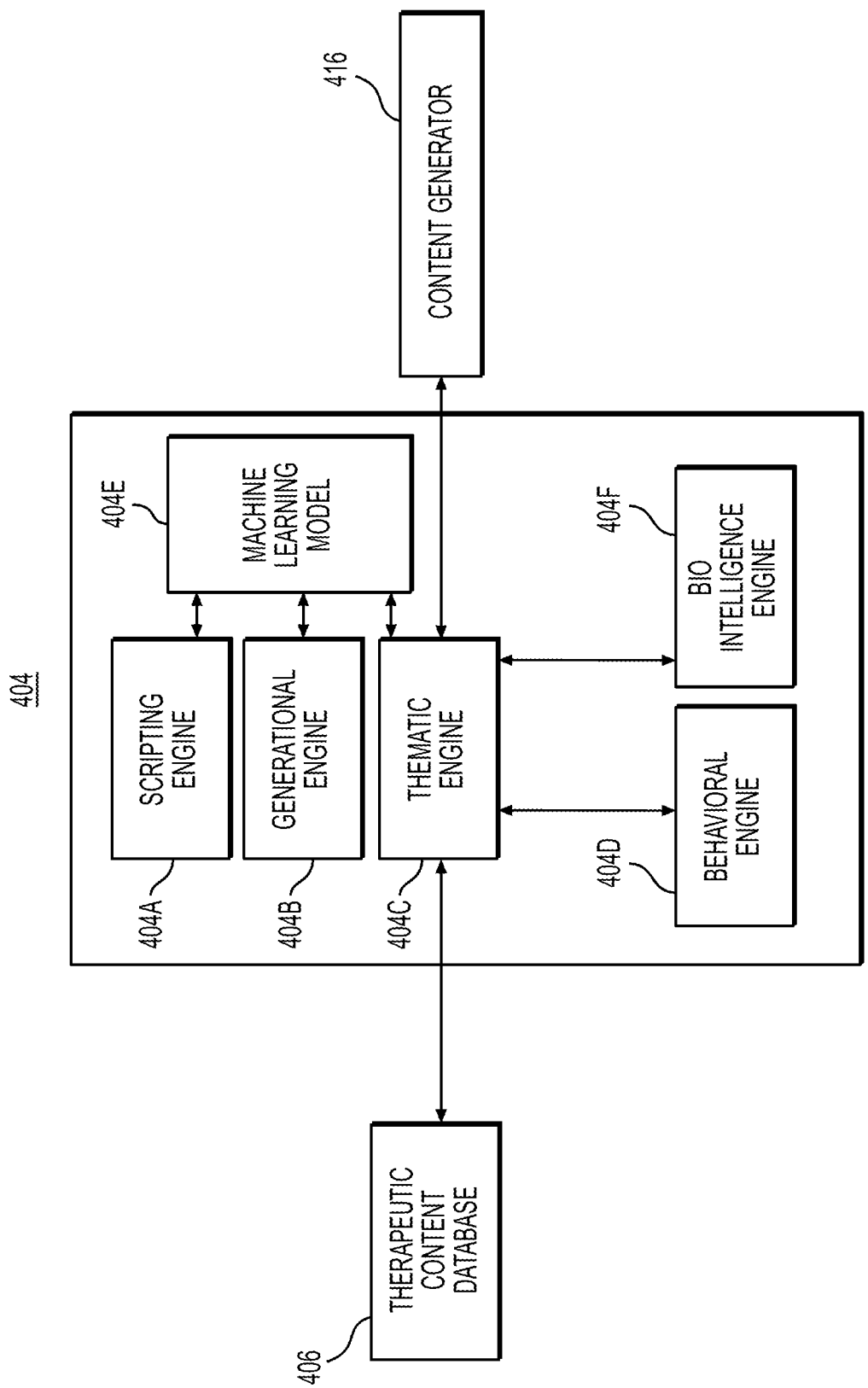
FIG. 4B shows a therapeutic machine learning platform, according to techniques presented herein.

FIG. 4B shows a detailed via of therapeutic machine learning platform 404. Therapeutic machine learning platform 404 may include a scripting engine 404A. Scripting engine 404A may receive a script from script generator 414 shown in FIG. 4A. Scripting engine 404A may include a set of deep learning algorithms that ingest and process a variety of scripts provided by script generator 414. Scripting engine 404A may extract scripting criteria, for example, terrain information, character information, plot information, brain-markers, or the like from a script provided by script generator 414.

The deep learning algorithms of a scripting agent may extract and/or normalize information from a plurality of types of script generators 414. For example, a first script generator 414 may provide a script in a first format and a second script generator 414 may provide a script in a second format. Script engine 404A may apply one or more deep learning algorithms to determine the first format and/or the second format, to then extract script information from the first format and/or second format. Accordingly, script engine 404A may enable therapeutic machine learning platform 404 to connect to one or more types of script generators 414. By applying script engine 404A, therapeutic machine learning platform 404 may be distributed as a module to connect to one or more script generators 414 as a plug-and-play component. Scripting engine 404A may output the scripting criteria.

Generational engine 404B may include a set of deep learning algorithms guided by scripting criteria output by scripting engine 404A. Generational engine 404B may implement a perceptron based neural network that adjusts the weights for different assets that have been identified. For example, generational engine 404B may apply weights to the scripting criteria based on a desired output (e.g., based on identifying content to minimize stress). Generational engine 404B may further categorize the weighted scripting criteria to identify a potential theme that the desired output corresponds to. According to implementations of the disclosed subject matter, the potential themes may correspond to one or more paradigms disclosed herein, may be the cyberdelic platform disclosed herein, or may be based on categories of content (fantasy theme, spa theme, action theme, etc.). Generational engine 404B may output the weighted scripting criteria and/or the potential themes.

Thematic engine 404C may include a set of deep learning algorithms that are guided by the generational engine 404B. Thematic engine 404C may use the scripting criteria and/or the potential themes to identify a pre-defined theme or to generate a new user specific theme. Thematic engine 404C may determine if a pre-defined theme (e.g., stored at a storage component or cache accessible to thematic engine 404C) matches a threshold amount with a potential theme. If the pre-defined theme matches by at least the threshold amount, the thematic engine 404C may select the pre-defined theme. If the pre-defined theme does not match by at least the threshold amount, the thematic engine 404C may facilitate generation of a new user specific theme. A new user specific theme may be stored for future use as a pre-defined theme. The threshold amount to determine if a pre-defined theme matches a potential theme may be determined initially by a machine learning component and may be updated based on application of a selected theme (e.g., pre-defined or new user specific theme) and subsequent feedback.

Thematic engine 404C may further identify one or more content in accordance with the selected theme, to present to user 412. The selection may be based on the selected theme and/or the scripting criteria. For example, a given theme may be associated with treatment of a given condition that user 412 is presenting, based on user inputs 402. Accordingly, the given theme may be selected by thematic engine 404C. Further, thematic engine 404C may identify content in accordance with the selected theme. The content may be fine-tuned, by thematic engine 404C, for user 412. The fine-tuning may include, for example, refining theme-based content specifically for user 412. As an example, theme-based content may be a VR scene that includes a dessert oasis. The fine-tuning based on user 412 (e.g., based on user inputs 402) may include modifying the color of trees in the oasis to best solicit a desired response from user 412.

Thematic engine 404C may output which content is to be output to user 412 based on the script and/or user inputs 402. The content may include, for example, three-dimensional (3D) objects, two-dimensional (2D) objects, sound, light, directional components, or the like. Thematic engine 404C may request an indication from therapeutic content database 406 regarding whether therapeutic content database 406 has the content to be output to user 412. Therapeutic content database 406 may provide an indication regarding whether it has the content, may provide an indication that it does not have the content, or may provide an indication that it has content similar to, though not the same as, the content to be output to user 412. Upon receiving an indication that therapeutic content database 406 includes the content to be output to user 412, thematic engine 404C may request the content from therapeutic content database 406. Therapeutic content database 406 may provide the content to thematic engine 404C or, according to an implementation, may provide the content to content rendering and distribution component 408.

Figure 4C:
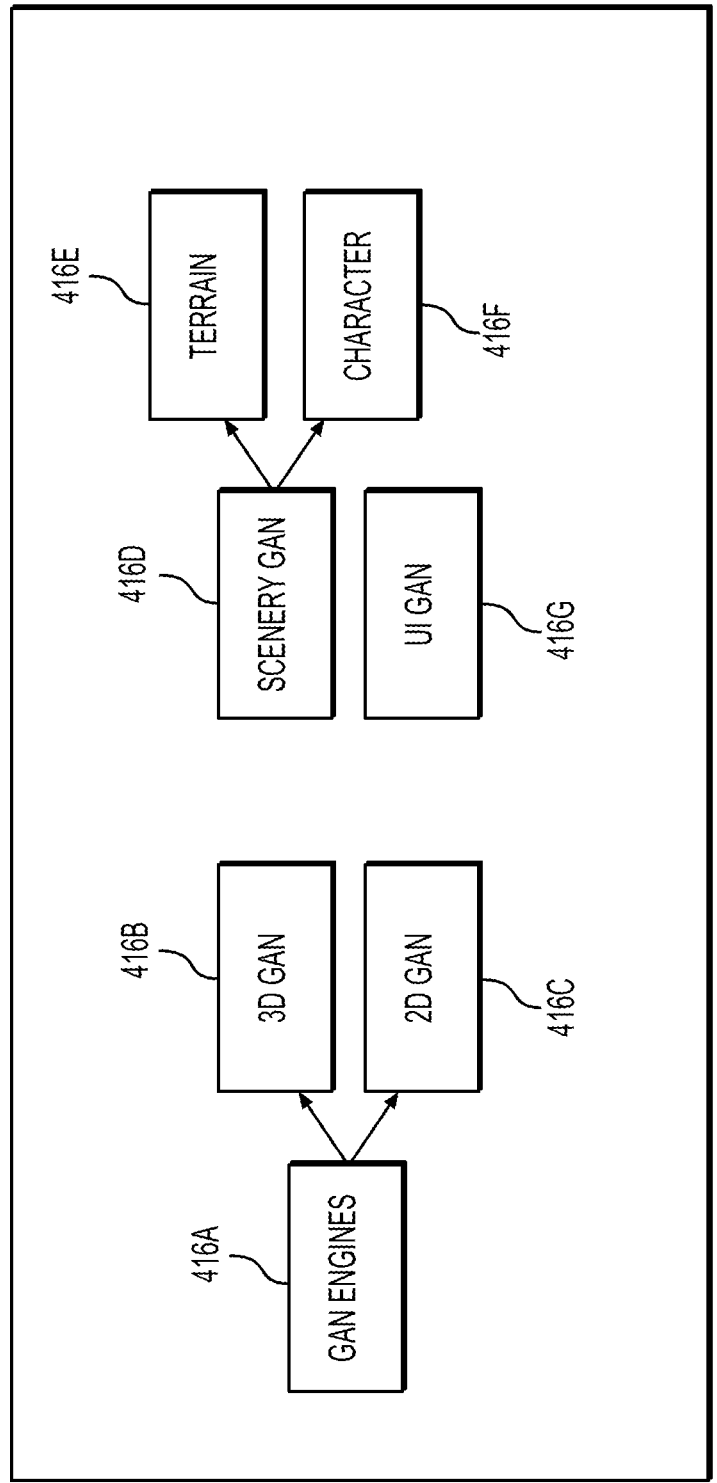
FIG. 4C shows a content generator, according to techniques presented herein.

Upon receiving an indication that therapeutic content database 406 does not include the content to be provided to user 412, thematic engine 404C may trigger content generator 416. Content generator 416 may generate the content to be provided to user 412. FIG. 4C shows content generator 416. Content generator 416 may include one or more generative adversarial network (GAN) engines 416A. A GAN engine, as applied herein may be a class of machine learning frameworks in which two neural networks contest with each other in a game (e.g., in the form of a zero-sum game, where one agent's gain is another agent's loss). Given a training set, a GAN engine based technique may learn to generate new data with the same statistics as the training set. For example, a GAN trained on photographs may generate new photographs that look at least superficially authentic to human observers, having many realistic characteristics. GAN engines may provide indirect training through a discriminator which itself is also updated dynamically. Accordingly, a corresponding generator may not be trained to minimize the distance to a specific image, but rather to obfuscate the discriminator. Such an implementation may enable a model to learn in an unsupervised manner.

GAN engines 416A may use an architecture (e.g., a fanout architecture) to generate N number of random scene assets. When a new generation request is received from thematic engine 404C, GAN engines 416A may search a system library to determine the right set of assets to pick as GAN input data. The GAN input data may be selected as being the closest asset(s) to the output content requested by thematic engine 404C.

GAN engines 416A may determine if the content to be provided to user 412 includes 3D content, 2D content, or a combination of the same. Based on the determination, GAN engines 416A may select scenery GAN 416D, user interface (UI) GAN 416G, or both. 3D GAN 416B may be configured to generate or modify 3D objects. 3D GAN 416B may generate 3D objects my combining individual objects (e.g., from a library), by modifying hex values, by generating pixels or voxels, by generating code, or the like. Scenery GAN 416D may be configured to organize 3D objects in a 3D space to create a scenery that user 412 can experience using user platform 410. Scenery GAN 416D may utilize a terrain 416E component and a character 416F component. Terrain 416E component may organize, place, or generate a terrain for user 412 to explore one or more 3D objects. For example, user 412 may explore a terrain with 3D objects using a VR headset. Accordingly, terrain 416E component may place 3D objects generated at 3D GAN 416B into a terrain for user 412 consumption. Similarly, Character 416F component may insert characters and/or user 412 preferences into a scenery for user 412 consumption. 2D GAN 416C may be configured to generate or modify 2D objects. 2D GAN 416C may generate 2D objects my combining individual objects (e.g., from a library), by modifying hex values, by generating pixels or voxels, by generating code, or the like. UI GAN 416G may be configured to organize 2D objects in a 2D space to create a visual that user 412 can experience using user platform 410.

Upon receiving an indication that therapeutic content database 406 includes content similar to the content to be provided to user 412, thematic engine 404C may receive the content similar to the content to be provided to user 412. Thematic engine 404C may determine aspects of the provided content that require updating to transform the content received from the therapeutic content database 406 into the content to be provided to user 412. The content received from therapeutic content database 406 as well as the required updates may be provided to content generator 416. Content generator 416 and its components (e.g., 3D GAN 416B, 2D GAN 416C, etc.) may modify the content received from therapeutic content database 406. Content generator 416 may output content to be provided to user 412 generated based on the content received from therapeutic content database 406.

Scripting engine 404A, generational engine 404B, and/or thematic engine 404C may independently include machine learning models or may be controlled using therapeutic machine learning model 404E. Therapeutic machine learning model 404E may receive inputs from scripting engine 404A, generational engine 404B, and/or thematic engine 404C and/or may provide outputs to scripting engine 404A, generational engine 404B, and/or thematic engine 404C. Therapeutic machine learning model 404E may update its weights and/or layers based on the inputs and/or outputs and may be trained using one or more machine learning algorithms as disclosed herein.

According to implementations, a behavioral engine 404D and/or a bio-intelligence engine 404F may be implemented. Behavioral engine 404D and/or a bio-intelligence engine 404F may be connected to thematic engine 404C. Behavioral engine 404D and/or a bio-intelligence engine 404F may verify consumable content prior to the content being provided to user 412.

Behavioral engine 404D may receive or generate a psychology profile of user 412. Behavior engine 404D may receive content to be provided to user 412 and may analyze the content in view of user 412's psychology profile. For example, behavior engine 404D may compare the content to determine the different objects included in the content. Behavior engine 404D may further compare the objects against the psychology profile of user 412 to determine if the psychology profile is compatible with the objects. If one or more objects, scenes, or other content component is not compatible with the psychology profile (e.g., if a content scene overlooks a mountain top but user 412 is afraid of heights), then behavioral engine 404D may flag the content component. A flagged content component may be modified or removed prior to presenting the corresponding content to user 412.

Bio-intelligence engine 404F may be configured to determine an intensity and/or dosage of a consumable content based on user 412 (e.g., based on user 412's psychology profile received or generated at behavioral engine 404D). Bio-intelligence engine 404F may operate using a closed feedback loop that incorporates user feedback from one or more content sessions, and/or user feedback provided by user 412 to fine-tune the intensity and/or dosage of consumable content.

Figure 4D:
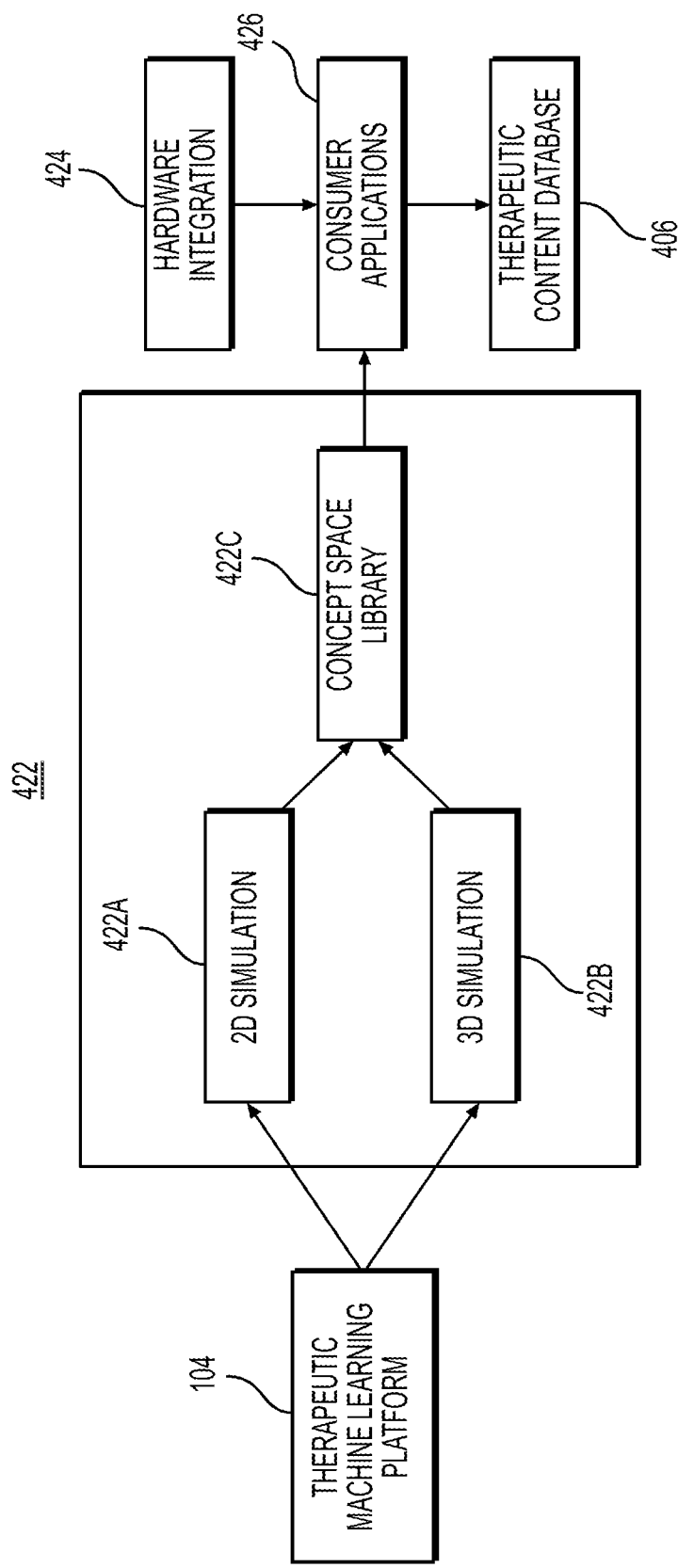
FIG. 4D shows a testing platform, according to techniques presented herein.

According to an implementation of the disclosed subject matter, a testing component 422 may be used to test the content output for user 412. The content may be received by testing component 422 via therapeutic machine learning platform 404, as shown in FIG. 4D, or may be received by therapeutic content database 406 and/or content generator 416. Past and/or current content as well as user consumption data (e.g., by user 412) may be used to define a data model. The content and consumption data may be fed into a concept knowledge (C-K) stage algorithm. A generated scene (e.g., by 3D GAN 416B) may be used to run a simulation engine (e.g., a Mujoco simulation engine) to collect 3D model data. A unity gaming engine based neural network may be used to train a virtual vehicle (e.g., a self-driving var) around in the generated scene (e.g., to mimic a user movement). Each path traveled by the virtual vehicle may receive a score based on how well that path and its corresponding objects, scenery, etc. result in a simulated intended effect (e.g., simulated reduction of stress). Terrain data may be collected (e.g., identification of objects that the simulated vehicle focuses on) using the path taken by the vehicle. The 3D model data and the terrain data may be combined and assigned to a concept space (C-space) for each user 412. A gaming engine environment may be used to set up a trigger-based setup to stimulate and collect data. Accordingly, the neural network may be trained using a reward based unsupervised learning algorithm and unity machine learning agents to identify and optimize content most suited to have an intended effect (e.g., reduction of stress, gene therapy, etc.) on user 412.

A path (e.g., traveled by a simulated vehicle) may be a 2D path or a 3D path. A 2D path may be analyzed by 2D simulation component 422A and a 3D path may be analyzed by 3D simulation component 422B. A path traveled by the simulated vehicle that meets a threshold score may be provided to concept space library 422C for additional testing. Accordingly, implementations disclosed herein may optimize content by parsing content provided via the therapeutic machine learning platform 404 via testing component 422 to identify optimal content for subsequent use.

Optimized content in content space library 422C may be provide to one or more users via consumer applications 426. The one or more users may evaluate the content in content space library 422C and, based on the evaluation, content in content space library 422C may be added to therapeutic content database 406 for subsequent use. Accordingly, content in content space library 422C may be content that is designated as optimal via a neural network and, additionally, may be added to therapeutic content database 406 based on user evaluation. User evaluations to the content may improve the therapeutic machine learning platform 404 by identifying objects, scenes, etc., that is most helpful for users 412 and may also allow therapeutic machine learning platform 404 to identify optimal intensity and/or dosage amounts.

According to an implementation, a hardware integration component 424 may also evaluate the content in content space library 422C and may provide a hardware integration score. The hardware integration score may be based on the amount of compatibility of the content to a hardware component (e.g., content quality via a given hardware component). Content may be added to therapeutic content database 406 for use with given hardware, based on the hardware integration score of that content with the given hardware component.

According to implementations of the disclosed subject matter, therapeutic machine learning platform 404 may be tested with electrocardiogram (ECG) devices such as a NextMind® kit. A probabilistic model may be used in an endless runner genre and may be integrated with live brain-based data provided to a component of omnichannel therapeutic system 400. Omnichannel therapeutic system 400 may use the probabilistic model integrated with live brain-based data to effectively generate, personalize, recommend, and/or deliver real-time script-based content at scale.

Feedback may be generated based on user 412's consumption of the consumable content via user platform 410. The feedback may be provided by user 412 (e.g., via a survey, questionnaire, ranking, etc.), provided by a third party (e.g., healthcare provider), and/or one or more sensors (e.g., a wearable device, a medical device, a patch sensor, a biometric sensor, a motion sensor, etc.). As an example of feedback provided by the user, user 412 may be presented a survey directly after consuming the consumable content or after a certain amount of time after the consumption of the consumable content. User 412 may respond to the survey to provide the feedback. As an example of feedback, a VR headset may log the actions taken by user 412 while in the environment of the consumable content. The actions may be stored as feedback. As an example of collecting feedback by one or more sensors, continuing the previous VR example, user 412 physical attributes may be scanned by one or more sensors while user 412 is in the VR environment of the consumable content. These physical attributes may be, for example, the user's heartbeat, gaze, blood oxygen level, pulse oxygen level, blood pressure, voice, movement, or the like or a combination thereof. The physical attribute feedback may be captured by one or multiple samples. As an example, user 412's gaze may be captured by a VR headset, user 412's heartbeat and blood oxygen level may be captured by a wearable device such as a smart watch, and user 412's voice may be captured by a microphone either placed in the VR headset or be placed independent of the VR headset, and/or natural language processing (NLP) from user generated word clouds.

The feedback may be provided to script generator 414, therapeutic machine learning platform 404, and/or user inputs 402. Script generator 414, therapeutic machine learning platform 404, and/or user inputs 402 may adjust a user profile corresponding to user 412 to update the user 412's treatment during a subsequent treatment session. According to an implementation, therapeutic machine learning platform 404 may be user specific such that a personalized machine learning model that is initially trained on a multi-user dataset is refined to cater to user 412. Therapeutic machine learning model 404E, script generator 414, and/or user inputs 402 may also re-adjust internal weights and/or layers for optimizing their performance during future treatment. For example, therapeutic machine learning model 404E may be iteratively trained such that each time it receives feedback, it updates its weights and/or layers (e.g., adjusts layers, removes layers, add layers, adjusts weights, removes weights, adds weights, etc.) based on the feedback. Dosing criteria (e.g., a duration of time to provide content) may also be updated based on the feedback. Additionally, therapeutic machine learning platform 404 may apply the feedback to update a global machine learning model such that treatment of other users is adjusted based on the feedback received from user 412. Over a large set of treatments and time, each user may benefit from the treatments of other users, as the omnichannel therapeutic system 400 of FIG. 4A applies user feedback to improve its scripts and/or content selections.

According to an implementation, feedback generated during user 412's consumption of content may be provided to the script generator 414 and/or therapeutic machine learning platform 404. An online monitoring and adaption implementation may adjust the consumable content being provided to user 412 during a given consumption session. For example, a determination may be made that user 412 would benefit most from a script based on a focus paradigm and a respective consumable content may be selected and provided to user 412 for consumption. During consumption, user 412's heartbeat may be detected by a heartbeat sensor on user 412's smart watch or headset mount. It may be determined that user 412's heartbeat has exceeded a threshold. Based on this determination, the content presented to user 412 may be adjusted. According to an implementation, the adjustment may be made dynamically and seamlessly such that user 412 does not experience an abrupt change. According to an implementation, script generator 414 and/or therapeutic machine learning platform 404 may determine that a different script or paradigm is most optimal for the user given the increase in heartbeat (e.g., may determine that the calm paradigm is most optimal) and, based on this determination, script generator 414 may provide an updated script and therapeutic machine learning platform 404 may extract (e.g., from therapeutic content database 406) or generate (e.g., using content generator 416) consumable content associated with the calm paradigm.

An automatic shut-off may be applied based on feedback received form user 412. For example, the feedback received from user 412 may indicate an elevated heart rate and based on the elevated heart rate, the automatic shut-off may be triggered to suspend the consumption of content by the user. The automatic shut-off may be implemented via user platform 410.

According to an implementation, post treatment feedback may be received and a determination may be made that the user would benefit from additional content and/or changes to supplement a treatment via omnichannel therapeutic system 400. Accordingly, the user may receive supplemental treatment via the user platforms 410 at any time after the treatment via omnichannel therapeutic system 400. The subsequent treatment may include, but is not limited to, additional content provided via one or more of the user platforms 410 at predetermined or user determined times, modification of the use of one or more of the user platforms (e.g., limited screen time, modified access to content, recommendations for use, recommendations for content, etc.), or the like, or a combination thereof.

Script generator 414, therapeutic machine learning platform 404 and, more specifically, therapeutic machine learning model 404E of FIGS. 4A and 4B are discussed further herein. Script generator 414, machine learning platform 404, and/or therapeutic machine learning model 404E (collectively referred to as a machine learning model) may learn to prioritize illness risk factors (e.g., stress, mental conditions, physical conditions, etc.) based on dynamic integration of individual, local, and global data. A computing device may receive data comprising inputs at 402. The computing device may receive a request for an evaluation of the data for generating a model (e.g., based on one or more machine learning algorithm) to predict responses based on one or more factors. The computing device may predict responses based on one or more neural network layers, one or more weights, or the like.

The machine learning model may include one or more or a combination of supervised, semi-supervised, and unsupervised learning or a form of learning called few-shot learning. For example, a supervised learning model may be used to estimate risk and the unsupervised learning model may be used to find naturally occurring patterns or groupings within the data (e.g., a precision medicine approach). Alternatively, for example, each of a supervised learning model and an unsupervised learning model may estimate risk and/or find naturally occurring patterns or groupings.

Figure 4E:
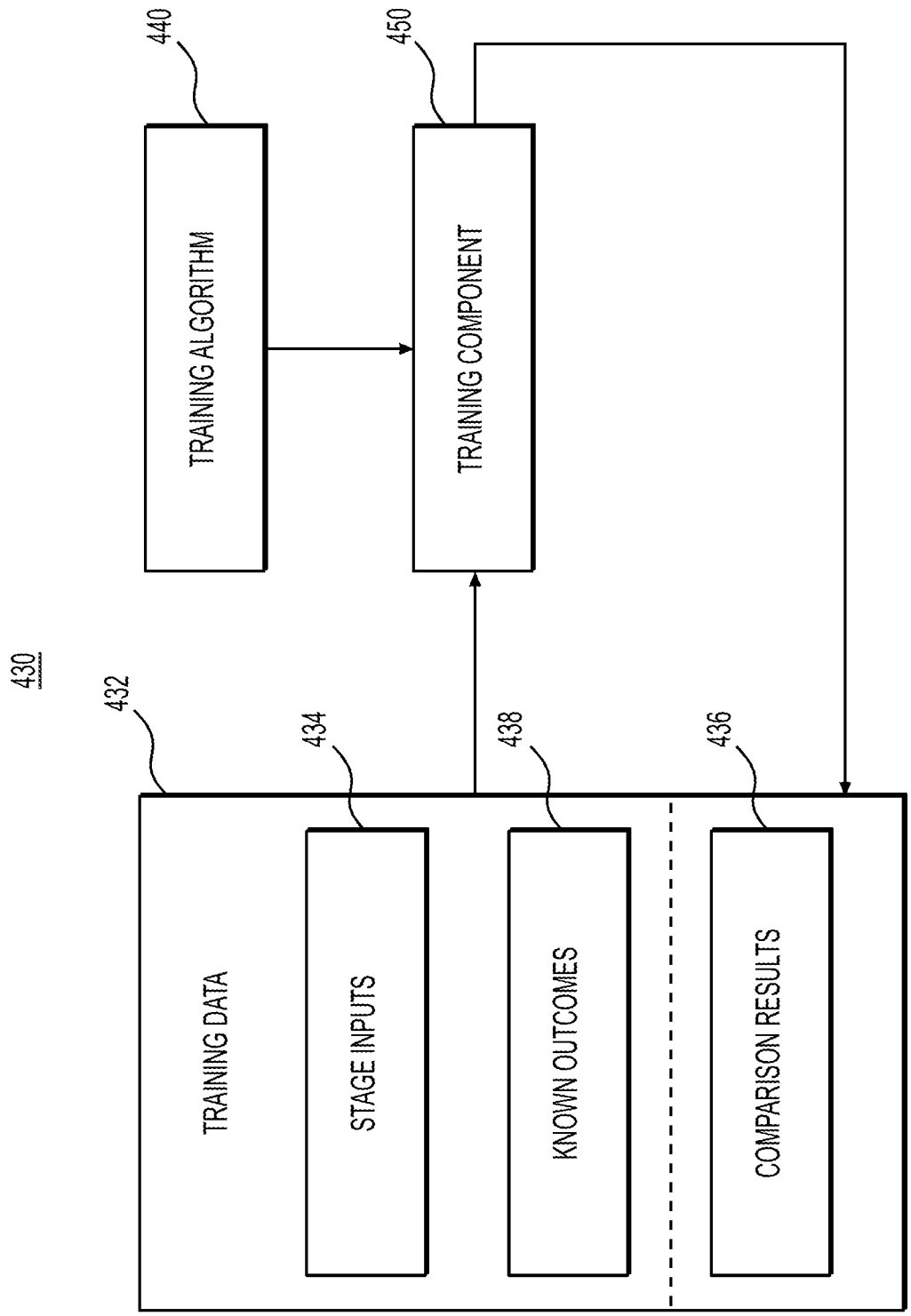
FIG. 4E shows an machine learning training platform, according to techniques presented herein.

A machine learning model disclosed herein may be trained using the data flow 430 of FIG. 4E. As shown in FIG. 4E, training data 432 may include one or more of stage inputs 434 and known outcomes 438 related to a machine learning model to be trained. Stage inputs 434 may be from any applicable source including user inputs 402, feedback, one or more outputs from a step from FIGS. 4A, 4B, 4C, and/or 4D, or the like. Known outcomes 438 may be included for machine learning models generated based on supervised or semi-supervised training. An unsupervised machine learning model may not be trained using known outcomes 438. Known outcomes 438 may include known or desired outputs for future inputs similar to or in the same category as stage inputs 434 that do not have corresponding known outputs.

The training data 432 and a training algorithm 440 may be provided to a training component 450 that may apply the training data 432 to the training algorithm 440 to generate a machine learning model. According to an implementation, the training component 450 may be provided comparison results 436 that compare a previous output of the corresponding machine learning model to apply the previous result to re-train the machine learning model. The comparison results 436 may be used by the training component 450 to update the corresponding machine learning model. The training algorithm 440 may utilize machine learning networks and/or models including, but not limited to a deep learning network such as Deep Neural Networks (DNN), Convolutional Neural Networks (CNN), Fully Convolutional Networks (FCN) and Recurrent Neural Networks (RCN), probabilistic models such as Bayesian Networks and Graphical Models, and/or discriminative models such as Decision Forests and maximum margin methods, or the like.

Figure 4F:
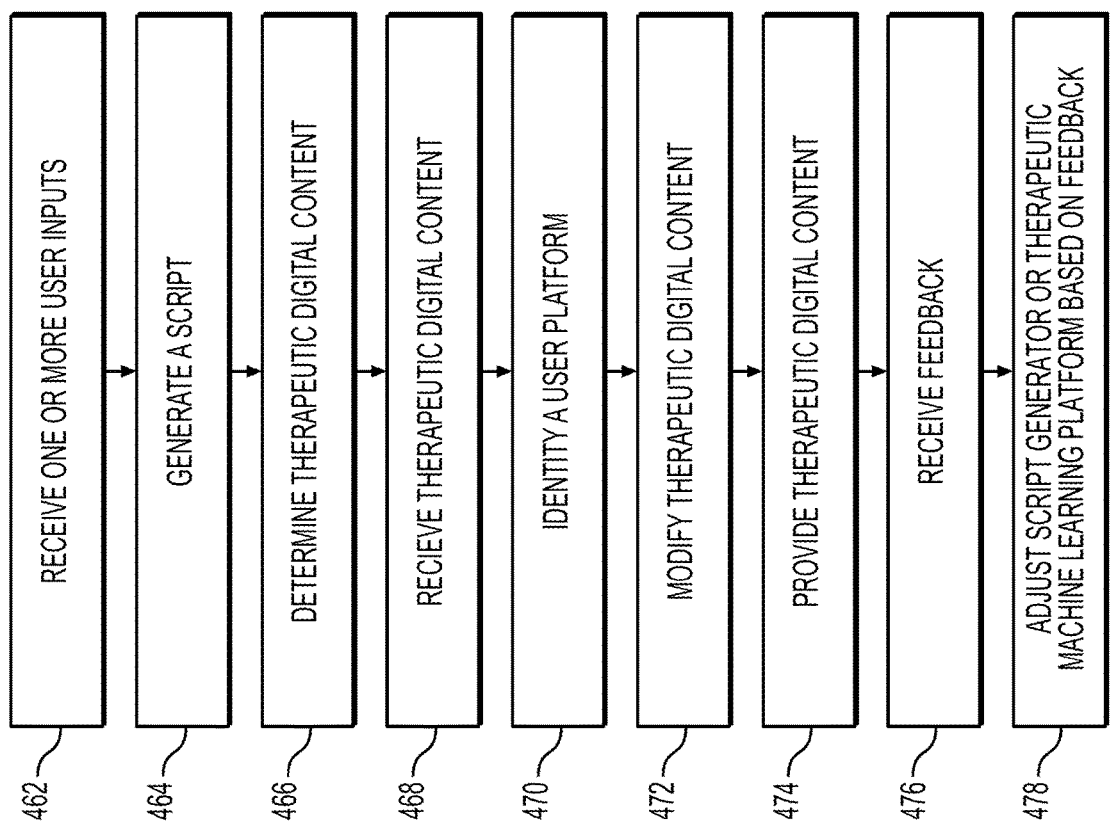
FIG. 4F shows a flowchart for implementing the omnichannel therapeutic platform of FIG. 4A using machine learning, according to techniques presented herein.

FIG. 4F shows a flowchart for implementing the omnichannel therapeutic system 400 of FIG. 4A. At 462, one or more user inputs 402 may be received. The user inputs 402 may be received at script generator 414 and at 464, the script generator 414 may generate a script. Based on the script, digital machine learning platform 404 may determine therapeutic digital content at 466. At 468, the therapeutic digital content may be received from therapeutic content database 406 and/or content generator 416. At 470, a user platform 410 may be identified. At 472, the therapeutic digital content may be modified based on user platform 410. At 474, the therapeutic digital content may be provided to user platform 410. At 476, feedback based on consumption of the therapeutic digital content may be received. At 478, the script generator 414 or therapeutic machine learning platform 404 may be updated based on the feedback.

Figure 5E:
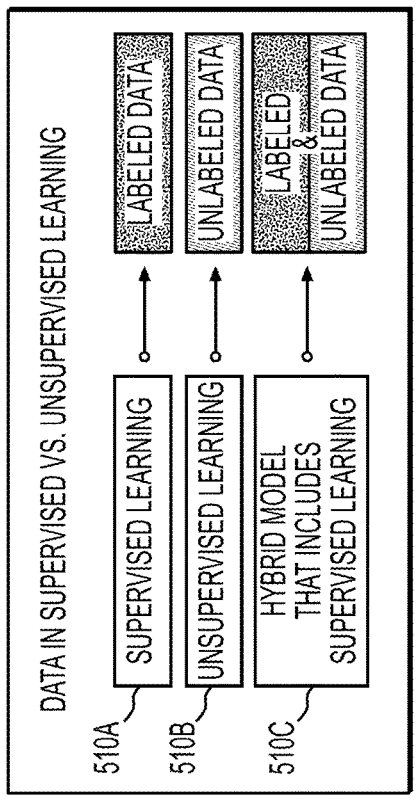
FIG. 5E shows a hybrid supervised and unsurprised machine learning model, according to techniques presented herein.

An initial learning approach may identify predictive features-feature selection to apply to a learning model. A function may relate values of the features to a prediction of disease and/or a paradigm for treatment (e.g., class assignment). A type of function may be identified. FIG. 5A shows a chart 502 with patient to outcome variance and FIGS. 5B-D show example functions to be applied by a machine learning model. For example, a logistic regression model may be used. With logistic regression, which is a type of generalized linear model, features are input into the model additively and linearly. Alternative models for prediction can be based on decision trees or convolution neural networks. A type of neural network format may be based on the type of input data to be provided as input to the corresponding machine learning model. A function that relates values of the features to a prediction of disease (e.g., class assignment) may be determined. Functions, as shown in FIGS. 5B-D, may be selected for use. For example, a decision tree may be used to predict a stress-based outcome (e.g., a heart attack), allowing the flexibility of "OR" choices as shown in chart 504 of FIG. 5B. A heart attack patient might have mutually exclusive causes such as familial hypercholesterolemia OR an arterial thrombotic disorder OR HIV, which would be difficult to model with logistic regression. Other types of machine learning models such as other neural networks may allow transformations of input features to better predict outcomes, as shown in the example provided in network 506 of FIG. 5C. Reinforcement learning may also be applied to, for example, explore an environment, experiment with decisions, observe inputs from the environment, and determine which decisions perform optimally. Support vector machines build classification models using a transformed set of features in higher dimensions. Prototype methods, such as k-nearest neighbors may be used make predictions based on the outcome of similar case, as shown in the example chart provided in chart 508 of FIG. 5D. The best guess for whether a patient will have a heart attack is to see if similar patients tend to have heart attacks.

Although FIGS. 5A-D are described herein as relating to heart conditions, it will be understood that the underling machine learning technology would apply to stress-based diseases, decisions, and/or outcomes. For example, a machine learning model may be generated for identifying a stress type based on a survey result. A script may be determined based on the identified stress type and a treatment may be determined accordingly.

Free parameters may be used to determine a fit to a machine learning model. In logistic regression, the regression coefficients may be determined and may include the weights applied to individual features. In decision trees, variables at which a split is performed may be determined. In instances including quantitative variables, the values at which the split is made may be determined. Neural networks may have free parameters related to the function used for feature transformation, as well as the function used to predict class based on these derived features. One or more machine learning algorithms may be used to determine computational methods to efficiently navigate the space of free parameters to arrive at an acceptable model.

Machine learning may be used to separate the tasks for fitting parameters and the quality of the results and may focus on a training set of examples to perform such tasks as feature selection and parameter fitting, and a test set to evaluate model performance. Using the training examples, different values for the free parameters may be attempted to assess how similar predicted outputs are to the known outputs. This may be referred to estimating training error and a loss function that is tailored to reflect what sort of errors are more tolerable than others, may be used. A model that minimizes training error may be optimal and a chosen algorithm may fit free parameters to achieve this goal.

A high-performing machine learning model may require multiple attributes for success. Informative features that reflect how a given set of classification classes are different from each other may be needed. The requisite input data may be available or all or some such data may be missing.

Script generator 414, therapeutic machine learning platform 404, and/or therapeutic machine learning model 404E of FIGS. 4A and 4B may be implemented using one or more techniques disclosed hereafter in reference to FIGS. 5A-D. FIG. 5A shows a matrix representation of the supervised and unsupervised learning that may be applied. As an example, a goal may be to develop a model for reducing stress associated with cancer, heart disease, stroke, and/or neurodegenerative disease. For training data, a plurality of users may be considered, each characterized by an outcome (positive or negative training examples), denoted by the circle in the right-hand column 502A, as well as by values of predictive features, denoted by shaded squares in section 502B. A model to predict outcome using some combination of features may be built. Multiple types of functions can be used for mapping features to outcome as shown in FIGS. 5B-D. Machine learning algorithms may be used to find optimal values of free parameters in the model to minimize training error as judged by the difference between predicted values from our model and actual values. In the unsupervised learning example, the outcome column may be ignored, and patients based on similarities in the values of their features may be grouped. FIG. 5B shows decision trees that map features to outcome. At each node or branch point, training examples are partitioned based on the value of a particular feature. Additional branches are introduced with the goal of completely separating positive and negative training examples. FIG. 5C shows neural networks to predict outcome based on transformed representations of features. A hidden layer of nodes integrates the value of multiple input nodes (raw features) to derive transformed features. The output node then uses values of these transformed features in a model to predict outcome. FIG. 5D shows the k-nearest neighbor algorithm that assigns class based on the values of the most similar training examples. The distance between patients is computed based on comparing multidimensional vectors of feature values.

Blending of unsupervised and supervised learning may be used to improve predictive models. A plurality of machine learning algorithms may be combined, and multiple combinations may be attempted to generate a suitable algorithm for a desired result (e.g., optimal script selection via script generator 414 of FIG. 4A).

A machine learning model may be trained based on traditional medicine, precision-medicine, and/or drug development. For example, the machine learning model may be trained, in whole or in part, using results obtained from traditional medicine. The machine learning model may include a personalization database and may receive user inputs 402. The machine learning model may include one or more of a dosage and therapeutic determination algorithm, a pre-during-and-post biometric data with decision tree component, a pre-during-and-post survey data with decision tree component, a user rendering and distribution decision tree component, a database storing historical usage data (e.g., for a current and/or previous users), and the like. A treatment for a user may be determined based on generating a script using the paradigm that provides the most optimal results for a given user. A machine learning model may be used to output the optimal paradigm for the user based on user inputs 402 that are used as inputs to a machine learning model generated based on a machine learning algorithm. The machine learning model may be trained using a training dataset including past successful treatments and their corresponding paradigms such that a selected learning algorithm learns to identify contextually related messages to generate the machine learning model. The training data may include the demographic, diagnostic, and physiologic variables discussed herein. The training data may be incorporated in supervised, semi-supervised, and/or unsupervised learning through labeled and unlabeled data as well as a hybrid model incorporating both, as shown chart 510 of FIG.

5E. As shown at 510A, supervised learning may be implemented with labeled data. As shown at 510B, unsupervised learning may be implemented with unlabeled data. As shown at 510C, a hybrid model that includes supervised learning may be implemented with both labeled and unlabeled data. The training data may include text (e.g., words and numbers), images, video, and/or audio, or the like or a combination thereof. Such data may be provided in any applicable format, such as a spreadsheet, PDF, HTML, or JSON. A selected learning algorithm may learn to identify contextually related messages to generate the machine learning model.

Figure 5F:
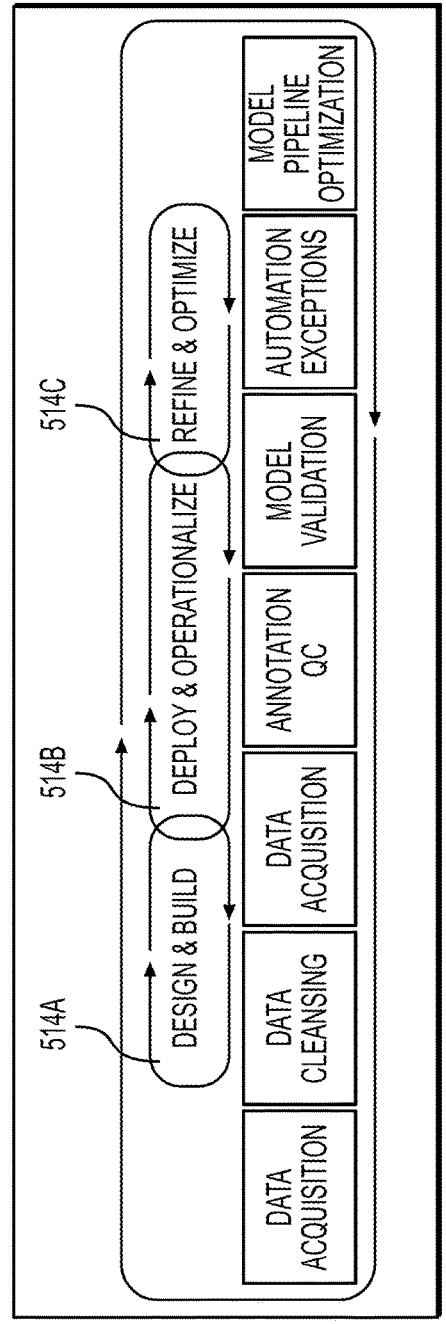
FIG. 5F shows an artificial intelligence model development lifecycle, according to techniques presented herein.

Additionally, FIG. 5F provides an AI model development lifecycle 512 that includes a design and build phase 514A (e.g., data acquisition and data cleansing), a deploy and operationalize phase 514B (e.g., data acquisition, annotations quality control, and model verification), and a refine and optimize phase 514C (e.g., automation exceptions and model pipeline optimization phase). According to an implementation, the deploy and operationalize phase as well as the refine and optimize phase may occur simultaneously (e.g., via an online learning strategy).

According to an implementation, a machine learning model may be based on one or more learning algorithms, such as a clustering algorithm, natural regression algorithm, or the like. The one or more machine learning algorithms may be stored in a memory, a cloud storage, a database, or the like and may be stored in multiple locations accessible during use or implementation of the machine learning algorithms. As used herein, a machine learning model may include instructions, algorithms, data, representations of data, or the like that are usable, for example, to correlate data and/or identify relationships between patient-based inputs and one or more paradigms. A machine learning model, as disclosed herein, further generally encompasses a model that may be trained, e.g., via a set of training data and one or more labels assigned to the set of training data, to generate an output for a particular input. Any suitable type of model may be used for the machine learning model, such as, for example, a neural network, a deep learning network, a genetic learning algorithm, or the like, or combinations thereof.

A machine learning model used herein may use one or more of a Support Vector Machine (SVM) algorithm, a Naïve Bayes algorithm, and a Random Forest (RF) algorithm, or a combination thereof.

Unsupervised learning means may be seen as a means of feature selection, as it can allow discovery of robust biological descriptors, which can then be used in a supervised model for disease prediction. An ensemble of different learning algorithms may be able to produce a superior prediction than any single one alone. Models using both genomic and clinical variables ended up surpassing either data type alone.

As mentioned above, unsupervised learning may be used to identify internal structure in data. An unsupervised learning process may start from a similar framework as supervised learning, with instances (users in this case) each characterized by a feature vector, where values are given for attributes. These data can be conveniently represented by a matrix, as shown in FIG. 5A. However, instead of using this matrix to learn a model relating features to outcomes, a group of users that are similar to one another may be found (e.g., a cohort). Multiple algorithms can be used for this purpose. The simplest may be an agglomerative hierarchical clustering, which first groups together individuals that are most similar to one another, and then merges together similar pairs, and so on and so on. Another class of unsupervised learning algorithms, including principal component analysis and non-negative matrix factorization, may perform a matrix decomposition, converting the user-feature matrix into a product of two matrices: one which groups together similar features into super-features (we call this dimensionality reduction) and a second which describes each user by a vector of weights applied to these super-features. Users may then be grouped based on similarity of their weight vectors. Another set of unsupervised learning methods such as k-medoids clustering and the attractor metagenes algorithm try to find distinct training examples (or a composite) around which to group other data instances. Examples within a cluster may be more similar to each other than to those of other clusters.

Sparse coding may assist in automated acquisition, processing and interpretation of images, and focuses on such tasks as facial recognition and the interpretation of handwritten text. Sparse coding may reflect how the visual cortex responds to stimuli. Rather than have a large number of cortical neurons activated by every image, the principle of sparsity instead has a very small number of neurons attuned to a much more specific, higher order aspect of the image, such as the edge of an object oriented in a particular direction. The machine learning models disclosed herein allow omnichannel therapeutic system 400 to learn a set of such higher order features from training images and then interpret test images as a composite of these features.

The goals that define the outputs (e.g., script or VR content for reducing stress) of the machine learning models of the omnichannel therapeutic system 400 of FIG. 4A may include the likelihood of stress reduction using digital content based on user 412's data, likelihood of stress reduction using digital content based on local data, likelihood that stress reduction using digital content based on global data, and/or a script based output to user platform 410. The goals may also include whether gene changes such as methylation or histone modification have been prevented, whether pathognomonic features of disease have been prevented or delayed, or the like. Such diseases include but are not limited to cancer, heart disease, stroke, and neurodegenerative disease.

When selecting content to provide to a user (e.g., from the therapeutic content database 406 and/or content generator 416), the inputs may be integrated. Integrated inputs may be demographics, survey data, biometrics, and prior outcomes, or the like, as disclosed herein. The content may be provided to the user such that specific content (e.g., VR scenes, images, videos, etc.) may be provided to a user at specific corresponding lucs of light and/or frequencies of sound. The specific lucs of light or frequency of sound may be determined by the machine learning model based on the user inputs (e.g., based on a script). The content may be sound based or may be provided with sound (e.g., music, voices, etc.) as well as any of the other sense modalities such as smell, touch and taste. As an example, a genre of music may be selected specifically by the machine learning model based on the user inputs 402. Similarly, audio, video, three dimensional, and other attributes may be determined based on the user inputs 402. For example, the user inputs 402 may be provided to a machine learning model and the machine learning model may determine the, tone, pitch, tempo, and volume of a sound or voice, may determine a preferred smell to be administered, may determine a preferred color, hue, saturation, brightness, contrast, intensity, etc., or may determine other attributes.

As disclosed herein, a user inputs 402 may include medications associated with the user such that the content its corresponding content attributes are determined, in part, based on the medication. As also disclosed herein, a machine learning model may also determine the dose (e.g., duration of consumption) of the specific content to be provided to the user. A machine learning model may also select content based on the user inputs 402 such that the content includes applicable landscape elements, landscape preferences (e.g. animals, mountains, oceans, beaches, etc.). The selection of the content may be weight-based, factoring in individual and/or global data. Psychedelic outputs may include the mystical, positive mood, beyond space/time, and ineffability outputs as further discussed herein.

A VR experience may be a simulated experience that can be similar to or completely different from the real world. Applications of virtual reality can include entertainment (e.g., video games) and educational purposes (e.g., medical or military training). Other, distinct types of VR style technology include augmented reality and mixed reality, sometimes referred to as extended reality or XR. For purposes of this application, it will be understood that VR includes augmented reality and mixed reality.

A VR experience may be implemented using either virtual reality headsets or multi-projected environments (e.g., user platform 410) to generate realistic images, sounds and other sensations that simulate a user's physical presence in a virtual environment. A person using virtual reality equipment may be able to look around the artificial world, move around in it, and interact with virtual features or items. The effect may be generated using a VR headset comprising a head-mounted display with a screen in front of the eyes but can also be created through specially designed rooms with multiple large screens. A VR experience may incorporate auditory and video feedback and may also allow other types of sensory and force feedback through haptic technology.

A VR headset may be used to facilitate the VR experience. A VR headset may be based on components such as, but not limited to, gyroscopes and motion sensors for tracking head, body, and hand positions; small HD screens for stereoscopic displays; and/or small, lightweight, and fast computer processors.

VR images may be generated using VR cameras such as omnidirectional cameras or 360-degree cameras that can record 360 interactive photography. Photogrammetry may be used to combine several high-resolution photographs for the creation of detailed 3D objects and environments in VR applications.

To create a feeling of immersion, special output devices may be used to display virtual worlds. Applicable formats include head-mounted displays. To convey a spatial impression, two images may be generated and displayed from different perspectives to facilitate stereo projection. Active components such as shutter glasses and passive technologies such as polarizing filters may also be used.

Special input devices may be utilized for interaction with a virtual world and may include, but are not limited to, a 3D mouse, a wired glove, motion controllers, and optical tracking sensors, or a combination thereof. Controllers may use optical tracking systems (primarily infrared cameras) for location and navigation, so that the user can move freely without wiring. Some input devices may provide the user with force feedback to the hands or other parts of the body, so that a user can orientate herself in the three-dimensional world through haptics and sensor technology as a further sensory sensation and implement realistic simulations. Using such input devices may enable a user to gain a sense of direction in an artificial landscape. Additional haptic feedback can be obtained from omnidirectional treadmills (with which walking in virtual space is controlled by real walking movements), vibration gloves, suits, and the like.

VR cameras may be used to create VR photography using 360-degree panorama videos. 360-degree camera shots may be mixed with virtual elements to merge reality and fiction through special effects.

Digital content based treatments disclosed herein may be administered to treat one or more specific conditions such as a generic syndrome (e.g., stress, burnout, insomnia, existential anxiety (fear of: death, freedom, loneliness, meaninglessness), etc.), a psychiatric diagnoses (e.g., Anxiety disorder not otherwise specified (NOS), panic disorder, generalized Anxiety Disorder (GAD), obsessive compulsive disorder (OCD), post-traumatic stress disorder (PTSD), social anxiety disorder, specific phobia, separation anxiety disorder, attention deficit hyperactivity disorder (ADHD), trans diagnostic, etc.), a corporate syndrome (e.g., impostor syndrome, summit syndrome, lack of resilience, lack of creativity, lack of agility, heart disease, etc.).

Script generator 414 may generate scripts based on one or more paradigms or based on a cyberdelic platform, as further discussed herein. Paradigms may be brain-based paradigms, with each paradigm designed to reflect an understanding of a predominant brain circuit implicated by anxiety or psychedelic relief. In other words, a paradigm may correspond to a neural circuit of a plurality of neural circuits such that each of the plurality of neural circuits are associated with a given anxiety or given psychedelic relief. A user, based on the patient's own individual health, circumstance, experience, etc., may benefit from addressing a given paradigm from the plurality of paradigms.

A multi-paradigm approach is provided for treatment via changing properties of patient brains, especially those that are stressed and/or anxious. Such treatment may be provided to prevent or mitigate medical conditions such as, but not limited to, cancer, heart disease, stroke, neurodegenerative disease, etc.

The multiple paradigms may include, but are not limited to, a calm paradigm, a focus paradigm, a distraction paradigm, a somatic paradigm, an escape paradigm, a possibility paradigm, and an awe paradigm.

The calm paradigm is disclosed hereafter. Anxiety increases amygdala activation in the brain, and an individual experiencing anxiety and increase in amygdala activation experiences being afraid and threatened. These reactions are coupled with physiologic changes including increased heart rate, decreased heart rate variability, and breathlessness. The calm paradigm links these anxiety-based results to scores on a HUMAN scale, PROM IS-Anxiety, GAD-2 and STAI-Y1.

Accordingly, in response to the calm paradigm, a calm specific digital content may be provided to user 412. The calm specific virtual input may change brain activation to decrease amygdala activation. Features of the calm specific virtual input include, but are not limited to, computer graphical image (CGI) based nature imagery, as well as other calm specific images including, but not limited to, water, sunrise, sunset, the moon, and floating blimps or relaxing in a chair, or being with a cup of hot, steaming beverage in the morning.

In comparison to other paradigms, the calm paradigm, which may include guided imagery using voice, does not emphasize asking for focus, distracting, relaxing a patient's body, providing a feeling of escape, or providing a sense of possibility, or providing a sense of awe.

The focus paradigm is disclosed hereafter. Multiple studies demonstrate that anxiety decreases prefrontal cortex (PFC) activation, and this combination makes it difficult to make decisions, assess risks, or think critically. The focus paradigm links these results to a PROMIS-Cognition scale as well as other measurements of focus and clear thinking.

Accordingly, in response to the focus paradigm, a focus specific digital content may be provided to user 412 to change brain activation to increase PFC activation. Relevant features include CGI based nature imagery, as well as other focusing images such as focusing on a fire, snow, fireflies, and other elements that can be tracked with the eye to capture attention.

In comparison to other paradigms, the focus paradigm, which may include guided imagery using voice, does not emphasize, calming a patient down, aiming to distract, asking a patient to relax their body, providing a feeling of escape, providing a sense of possibility, or providing a sense of awe.

The distraction paradigm is disclosed hereafter. Multiple studies demonstrate that anxiety increases attention to threat such that the front parietal cortex is activated and connects with the amygdala such that it is fixated on the amygdala causing excessive worry and dispositional negativity. The distraction paradigm links these results to scores that measure worry and obsessional worry symptoms.

Accordingly, in response to the distraction paradigm, a distraction specific digital content may be provided to user 412 to change brain activation to decrease disrupt front parietal-amygdala connectivity. Relevant features include CGI based nature imagery, as well as other distracting images that aim to disconnect attention from worry.

In comparison to other paradigms, the distraction paradigm, which may include guided imagery using voice, does not emphasize, calming a patient down, aiming to focus, asking a patient to relax their body, providing a feeling of escape, providing a sense of possibility, or providing a sense of awe.

The somatic paradigm is disclosed hereafter. Multiple studies demonstrate that anxiety increases body tension and impacts the somatic regions in the brain. The somatic paradigm links these results to scores that measure bodily discomfort.

Accordingly, in response to the somatic paradigm, a somatic specific digital content may be provided to user 412 to change brain activation to decrease disrupt front parietal-amygdala connectivity. Relevant features include CGI based nature imagery, as well as other bodily relaxing images and instruction that aim to relax the somatically activated brain regions.

In comparison to other paradigms, the somatic paradigm, which may include guided imagery using voice, does not emphasize, calming a patient down, aiming to focus, aiming to distract, providing a feeling of escape, providing a sense of possibility, or providing a sense of awe.

The escape paradigm is disclosed hereafter. Multiple studies demonstrate that when anxiety is severe, it impacts the periaqueductal gray and people feel trapped. The escape paradigm links this response to scores that measure anxiety and entrapment.

Accordingly, in response to the escape paradigm, an escape specific digital content may be provided to user 412 to change brain activation to decrease PAG activation. Relevant features include CGI based nature imagery, as well as other escape images that aim to release people from this feeling of entrapment.

In comparison to other paradigms, the escape paradigm, which may include guided imagery using voice, does not emphasize, calming a patient down, aiming to focus, aiming to distract, asking patients to relax their body, providing a sense of possibility, or providing a sense of awe.

The sublime paradigm is disclosed hereafter. Multiple studies demonstrate that anxiety and sublimity are connected but not identical, and that anxiety itself may be connected to boredom, lack of awe, and brain systems such as the default mode network (DMN) that are stuck. The sublime paradigm links this response to scores that measure boredom and sublimity.

Accordingly, in response to the sublime paradigm, a sublime specific digital content may be provided to user 412 to re-organize DMN activity without activating the amygdala predominantly. Relevant features include CGI based nature imagery, as well as other sublime images that aim to release people from this feeling of boredom and excite them.

In comparison to other paradigms, the sublime paradigm, which may include guided imagery using voice, does not emphasize, calming a patient down, aiming to focus, aiming to distract, asking patients to relax their body, providing a sense of escape, or providing a sense of possibility.

The possibility paradigm is disclosed hereafter. Multiple studies demonstrate that anxiety limits a sense of possibility and creates a sense of foreshortened future, thereby affecting mental time travel circuits with limited access to the past. The possibility paradigm links this response to scores that measure future-thinking and a sense of possibility.

Accordingly, in response to the possibility paradigm, a possibility specific digital content may be provided to user 412 to activate the DMN and time-travel circuits to allow for greater future-thinking. Relevant features include CGI based nature imagery, as well as other images that aim to facilitate time travel into the past and future.

In comparison to other paradigms, the possibility paradigm, which may include guided imagery using voice, does not emphasize, calming a patient down, aiming to focus, aiming to distract, asking patients to relax their body, providing a sense of escape, or providing a sense of awe.

Table 1 below shows a brain-based image design and targeting system in accordance with each of the paradigms disclosed herein.

TABLE 1

| PRIMARY | PRIMARY BRAIN TARGET | PRIMARY OUTCOME | PRIMARY DISTINGUISHING FEATURE |
| --- | --- | --- | --- |
| CALM | Amygdala | Calming | Smooth, relaxing ride through calming scenarios |
| FOCUS | PFC | Focusing | Instructions to focus on specific stimuli |
| DISTRACTION | Fronto-parietal cortex | Distracting | Temporary redirection of attention-feeling of being unstuck |
| SOMATIC | Somatic regions | Relaxing | Instructions to relax the body |
| ESCAPE | PAG | Relieving | Build of possible entrapment and then escape-tension and release |
| POSSIBILTIY | Time-travel circuits (DMN and Hippocampus) | Believing | Choices built into paradigm e.g. doors and paths opening; magical |
| SUBLIME/AWE | DMN | Inspiring | Heightened |

TABLE 1-continued

| PRIMARY | PRIMARY BRAIN TARGET | PRIMARY OUTCOME | PRIMARY DISTINGUISHING FEATURE |
|---|---|---|---|
| | disruption | | aesthetic and images of awe |

Omnichannel therapeutic system 400 may provide digital content for prevention and/or treatment of one or more conditions. User 412 may be provided digital content based on a script generated for a given paradigm to mitigate or treat the user 412's specific conditions. User 412 may gain access to the digital content by logging into a system.

According to an implementation, the omnichannel therapeutic system 400 may target genes and/or reactive oxygen species via use of the omnichannel therapeutic system 400 described in FIG. 4A. Stress-based techno genes may be determined based on personalized epigenetic building blocks that indicate predisposition to an illness due to stress-related factors.

The therapeutic platform may also incorporate geometry into its treatment such that visual perception-based geometry is factored in when providing content to a user. The content may comprise mindfulness-based nature-imagery. Digital content may be delivered using multisensory inputs and/or specific waveforms.

According to an implementation, the omnichannel therapeutic system 400 disclosed herein may be used in addition to or as a replacement for one or more antidepressant or anti-anxiety medications including, but not limited to Selective serotonin reuptake inhibitors (SSRIs), Benzodiazepines, Tricyclic antidepressants, serotonin-norepinephrine reuptake Inhibitor (SNRI), and/or atypical antiphychotics, such as Prozac®, Paxil®, Luvox®, Ativan®, Xanax®, Klonopin® (SSRI, TCA, Venlafaxine, Benzodiazepine, Nefazodone, Zyprexa), etc., or the like or a combination thereof. One or more of these medications may be provided as user inputs 402 to omnichannel therapeutic system 400 such that the content selected for user 412 is based, at least in part, on the knowledge that the therapeutic treatment is being supplemented by one or more of these medications.

According to an implementation, omnichannel therapeutic system 400 which may apply a cyberdelic platform, further disclosed herein, may be used to treat one or more diseases (e.g., coronary heart disease, cancer (e.g., prostate cancer), stroke, Alzheimer's disease, etc.) as a combination therapy that supplements one or more other traditional treatments such as chemical drugs or medical device treatments. As an example, a dosage of curated digital content may be prescribed or otherwise provided to user 412 that is also taking traditional drugs to treat a specific medical condition. The dosage of the curated digital content may be determined, at least in part, based on one or both of the specific medical condition and/or the traditional drugs that supplement the virtual therapeutic therapy.

According to an implementation, omnichannel therapeutic system 400 may be implemented in combination with holotropic breathwork. Holotropic breathwork may induce beneficial temperament changes as well as brain-based changes in physiology that promote wellbeing. Holotropic breathwork may decrease stress and cortisol levels and, as a result add to the positive effects of omnichannel therapeutic system 400. In addition to holotropic breathwork or as an alternative to the holotropic breathwork, omnichannel therapeutic system 400 may be combined with relaxation breathing, mindfulness breathwork, and/or yogic breathing that may be helpful for treating anxiety, depression, and/or posttraumatic stress disorder or for simply alleviating stress and in specific instances, such as existential anxiety. The entire platform may alleviate existential anxiety. In addition to holotropic breathwork or as an alternative to the holotropic breathwork, the therapeutic platform and/or the cyberdelic platform may be combined with deep breathing as well as other forms of meditation including transcendental meditation, Vipassana meditation, and or more varieties of yoga or yoga-based techniques. Holotropic breathwork guidance may be generated based on therapeutic digital content output by omnichannel therapeutic system 400. For example, a type, amount, or intensity of holotropic breathwork guidance may be determined based on the therapeutic digital content provided to a user. A given type of therapeutic digital content may correspond to a given type, amount or intensity of holotropic breathwork guidance.

Holotropic breathwork may include various breathing practices in which the conscious control of breathing influences a mental, emotional, or physical state, with a therapeutic effect. It may include practice that uses breathing and other elements to putatively allow access to non-ordinary states of consciousness.

According to an implementation, omnichannel therapeutic system 400 may interact with one or more virtual games such as to implement a game-based digital therapeutic device to improve attention functions. As an example, omnichannel therapeutic system 400 may be paired with VR based visual effects of a video game where one or more given visual effects are determined by a machine learning model of omnichannel therapeutic system 400 and extracted from a video game library acting as a content database. Additionally, omnichannel therapeutic system 400 may be implemented with music experience platforms that generate images from music (e.g., Red Pill).

Figure 6:
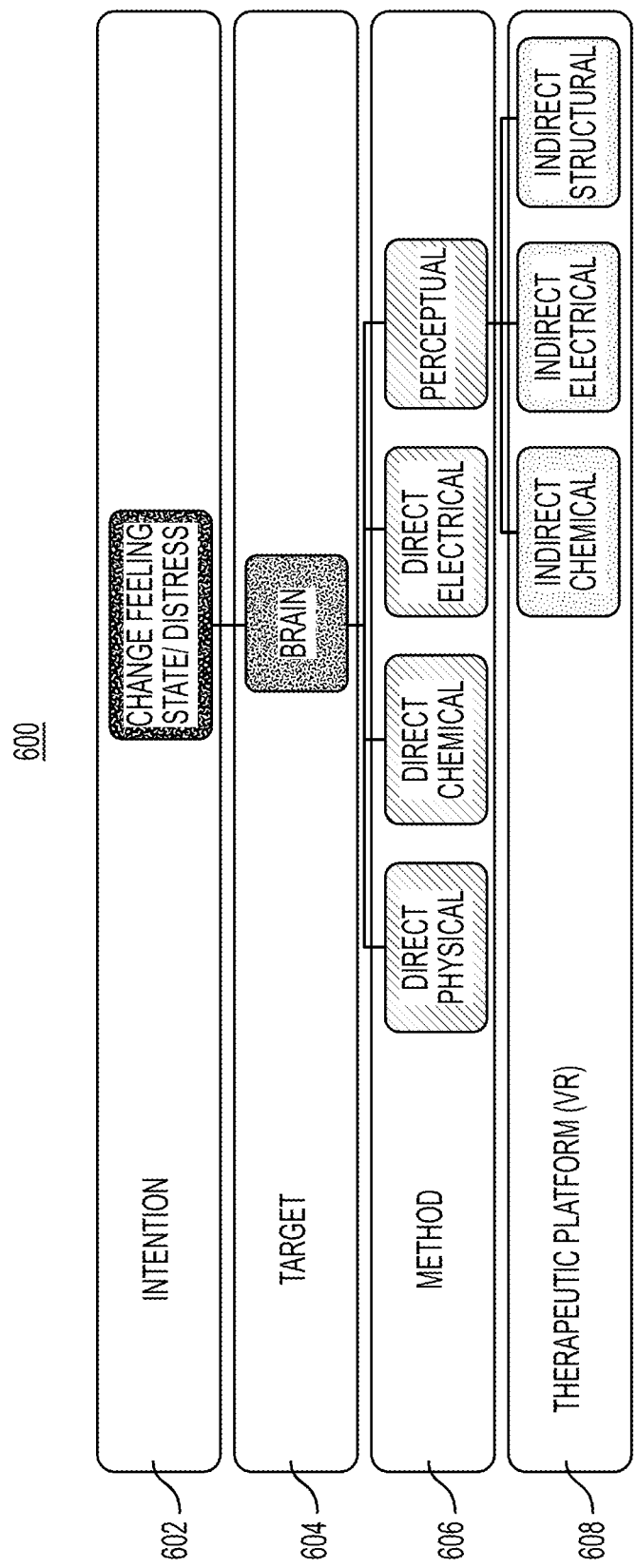
FIG. 6 shows an implementation of a therapeutic platform, according to techniques presented herein.

FIG. 6 shows an example diagram 600 for the implementation of omnichannel therapeutic system 400 incorporated into traditional treatments. As shown, the intention 602 of the traditional treatments is to change the feeling or state of distress by targeting the brain at 604. The methods 606 used can include direct physical intervention, direct chemical intervention (e.g., via drugs), direct electrical intervention (e.g., via electrotherapy), and perceptual (e.g., via the therapeutic platform disclosed herein). The perceptual method using the therapeutic platform at 608 disclosed herein has indirect chemical effects, indirect electrical stimulation/scrambling, and indirect structural changes/scrambling.

Figure 7:
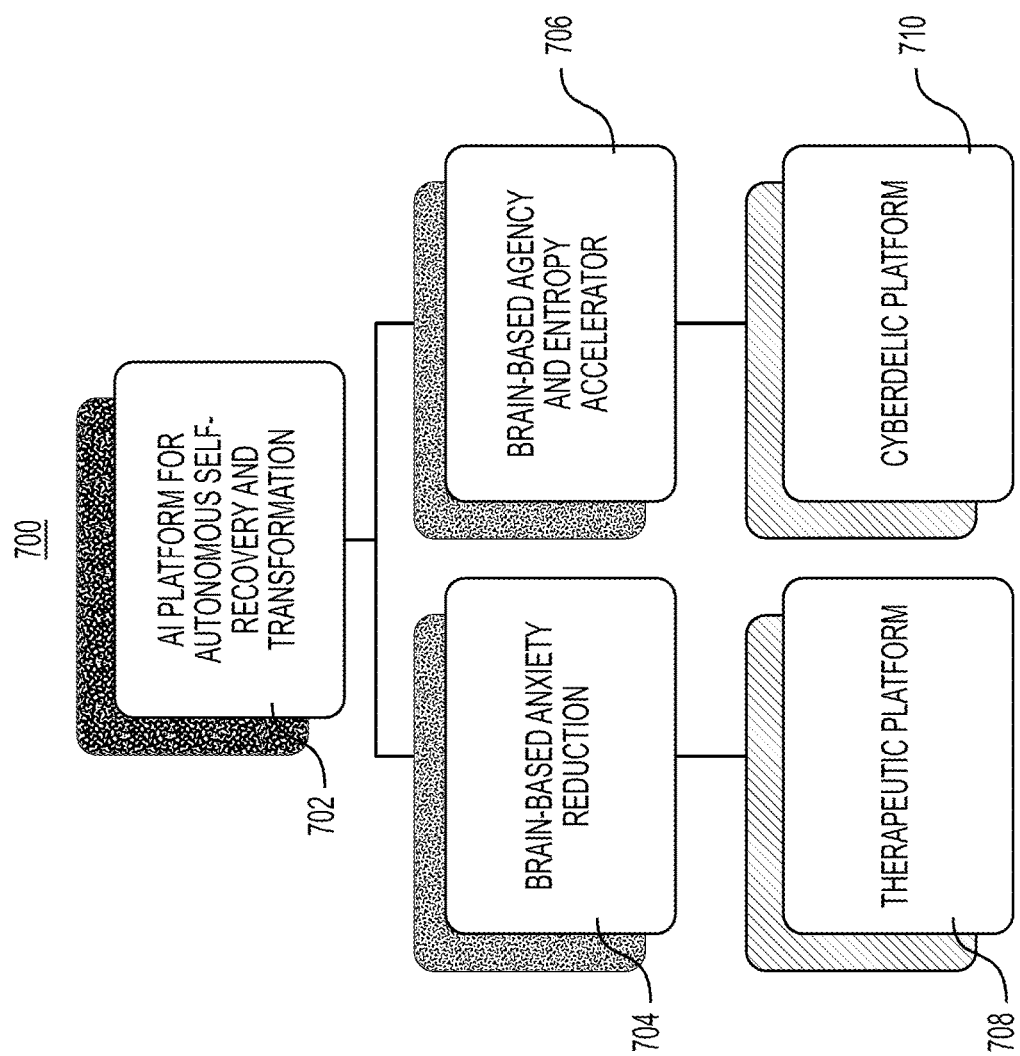
FIG. 7 shows a diagram for a therapeutic platform track and a cyberdelic platform track, according to techniques presented herein.

FIG. 7 shows an example diagram for how omnichannel therapeutic system 400 can be supplemented with a cyberdelic platform further disclosed herein. At 702, an artificial intelligence platform (e.g., omnichannel therapeutic system 400) may identify one or more platforms to implement for a given patient. At 704 a determination may be made to address brain-based anxiety reduction using the therapeutic platform (e.g., omnichannel therapeutic system 400). At 706 a determination may be made to address brain-based agency and entropy accelerators using a cyberdelic platform 710. Cyberdelic platform 710 may be used as an input to omnichannel therapeutic system 400. For example, similar to one or more paradigms, script generator 414 may receive outputs from cyberdelic platform 710 and may incorporate these outputs in generating a script. Therapeutic machine learning platform 404 may output digital content in view of the outputs from the cyberdelic platform 710.

Omnichannel therapeutic system 400 includes multiple digital applications or interventions. A first application may be a multi-pronged (e.g., 7-pronged) anxiety reduction therapy (e.g., based on paradigms). Another application is a cyberdelic implementation as disclosed herein. Although a cyberdelic platform is discussed herein as a separate platform than omnichannel therapeutic system 400, it will be understood that the cyberdelic platform maybe used with or as part of omnichannel therapeutic system 400. A cyberdelic implementation may be a multi-pronged (e.g., 4-pronged) self-scrambling solution based on brain circuits impacted by psychedelics. The cyberdelic platform may be a virtual reality platform (e.g., a virtual or visual platform) that has some or all of the same functionalities as omnichannel therapeutic system 400. It may be implemented using headphones, may have an auditory component, and may be combined with smells and other perceptions. A difference between the omnichannel therapeutic system 400 and the cyberdelic platform may be that the circuits targeted by each respective platform. For example, omnichannel therapeutic system 400 may target the 7 paradigms provided herein, the cyberdelic platform may target the circuits outlined in FIG. 9B (e.g., mystical, positive mood, ineffability, and beyond space/time), as well as their subcircuits outlined in FIGS. 10-16. Accordingly, the designs for each respective platform may be different. For example, images to represent sacred geometry as well as other perceptual phenomena associated with psychedelics may be used. A user may choose the experience preferred by the user instead of being forced an unfavorable experience. As disclosed, the effects of a given experience can be dosed (e.g., via time, intensity, etc.) and may be switched. Both platforms may be multisensory, but the sound frequencies disclosed herein may be applied via the cyberdelic platform.

It will be understood that although omnichannel therapeutic system 400 and a cyberdelic platform are specifically disclosed herein, implementations of the disclosed subject matter are not limited to these platforms. The implementations disclosed herein may be implemented using any non-physical platform and is not limited to existing limitations of virtual reality, digital displays, wearable devices, headsets, or the like. For example, non-device-based provision of digital content may be used as a platform to implement the disclosed subject matter.

As shown in flow diagram 700 of FIG. 7, the therapeutic platform track and the cyberdelic platform track are both are based on an artificial intelligence platform for autonomous self-recovery and transformation where the therapeutic platform 708 (e.g., omnichannel therapeutic system 400) is applied for brain-based anxiety reduction and a cyberdelic platform may be applied as a brain-based agency and entropy accelerator to enhance intelligence and self-reorganization, thereby providing therapeutic benefits currently associated with psychedelics such as alleviation of depression and PTSD. Similar to omnichannel therapeutic system 400, the cyberdelic platform may decrease stress, and, contribute to gene care and the prevention of the same diseases. As described herein (e.g., at FIG. 1A) before cells differentiate, they are all the same. Hence, the liver, brain, legs and spine all come from the same origin. Similarly, before diseases differentiate into cancer, heart disease, stroke etc., they share many mechanisms, such as increased inflammation, gene alterations by stress, abnormalities in the default mode network in the brain etc. Accordingly, diseases may be prevented and treated prior to and after they differentiate. Prior to differentiation, gene changes that lead to disease may be prevented. After differentiation, interruption and reversal of gene changes may be implemented.

Techniques and systems disclosed herein may be implemented to impact stress, morbidity (i.e., illness), and mortality (i.e., life expectancy). Omnichannel therapeutic system 400 may be used as part of an autonomic self-recovery and/or transformation platform. Stress, as used herein can be stimulus-based, response-based, dynamics-based, or may be based on or more factors.

Stimulus based stress may be stress that results from pressure. The greater the pressure the more likely that the recipient, whether a person or a load-bearing beam, will succumb. When the external stimulus becomes too great, internal collapse becomes inevitable. For response-based stress, the body may alerted and may respond with an alarm reaction. As a result, autonomic activity may be triggered as the body prepares to deal with the stress. This is the stage of resistance. Finally, if the stress continues beyond the capacity of the body to respond, the system is damaged and may collapse. This is the stage of exhaustion. Dynamics-based stress is a particular relationship between the person and the environment that is appraised by the person as taxing or exceeding his or her resources and endangering his or her wellbeing.

In adopting the approach that stress is a dynamic process, it is assumed that different individuals have different responses to stress. As such, N-of-1 studies become a basis of assessing efficacy. N-of-1 or single subject clinical trials consider an individual patient as the sole unit of observation in a study investigating the efficacy or side-effect profiles of different interventions. The ultimate goal of an N-of-1 trial may be to determine the optimal or best intervention for an individual patient using objective data-driven criteria. An N-of-1 system using the dynamic input and output variables described above may be implemented. An N-of-1 implementation may personalize the efficiency of each treatment. N-of-1 or single subject clinical trials may consider an individual patient as the sole unit of observation in a study investigating the efficacy or side-effect profiles of different interventions. Use of N-of-1 trial may determine the optimal or best intervention for an individual patient using objective data-driven criteria. Such trials may leverage study design and statistical techniques associated with standard population-based clinical trials, including randomization, washout and crossover periods, as well as placebo controls.

Stress can be associated with many physical illnesses. In cancer, psychological stress is a risk factor for cancer initiation and progression. In heart disease, stress is strongly related to coronary heart disease. In strokes, stress is strongly associated with increased incidence and prevalence of strokes. Stress is also strongly associated with Alzheimer's disease and neurodegenerative disease.

Stress reduction improves anxiety and physical illnesses. Enhanced coping can result in reduced stress, pain and possibly metastases in cancer patients. Reduced stress can also result in a reduced rate of heart disease or cardiac mortality and morbidity associated with anxiety. Reduced stress lowers chances of strokes and morbidity. Reduced anxiety and stress can result in lower severity of Alzheimer's and neurodegenerative disease and can result in possible prevention.

According to an implementation, entropy enhancement techniques can be implemented using a cyberdelic model with the goal of impacting stress through reorganizing functional brain connectivity.

Entropy is a dimensionless quantity that is used for measuring uncertainty about the state of a system, but it can also imply physical qualities, where high entropy is synonymous with high disorder. System entropy, as it is applied to the brain, is related to self-organized criticality. The phenomenon of self-organized criticality refers to how a complex system (e.g., a system with many constituting units that displays emergent properties at the global level beyond those implicated by its individual units) forced away from equilibrium by a regular input of energy, begins to exhibit interesting properties once it reaches a critical point in a relatively narrow transition zone between the two extremes of system order and chaos.

Entropy can influence the brain. Depressed patients have decreased entropy in bilateral thalami compared to controls. Alzheimer's disease is associated with increases in resting-state brain entropy as well as decreases in permutation entropy (decrease complexity). Stress decreases entropy in heart rate variability and, by implication, flexible brain network activity. The entropic brain hypothesis proposes that within upper and lower bounds, such as within a critical zone, the entropy of spontaneous brain activity indexes the richness, diversity and vividness, of subjective experience, within any given state of consciousness, and that psychedelics acutely increase both bounds.

Higher brain entropy is associated with enhanced intelligence. The higher the entropy, the higher the level of information processing in the brain.

Figure 8A:
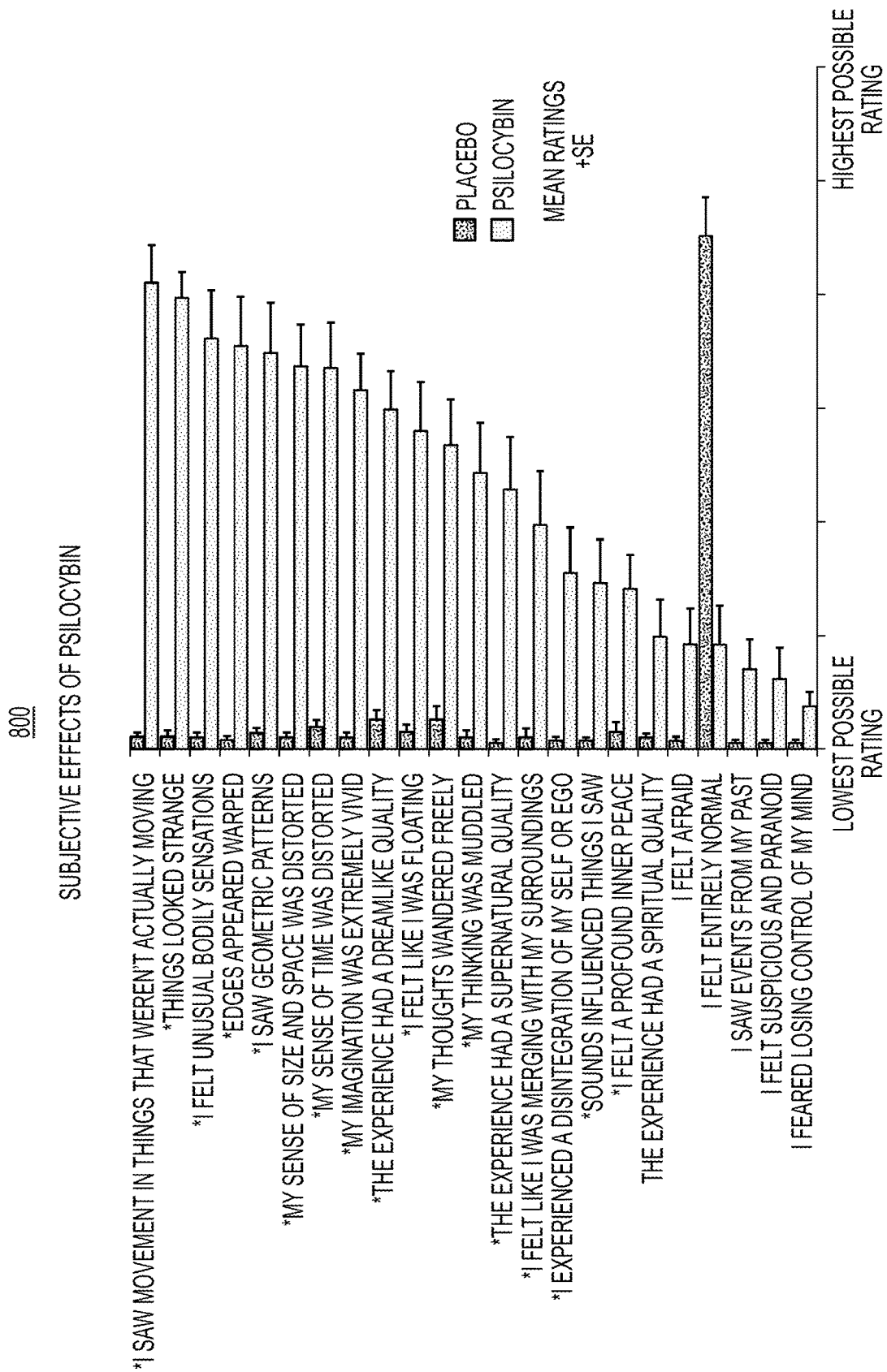
FIG. 8A shows example effects of psilocybin as compared to a placebo, according to techniques presented herein.

Psychedelics, also known as hallucinogens, are a class of psychoactive substances that produce changes in perception, mood, and cognitive processes. Psychedelics promote structural and functional neural plasticity. Psychedelics are used as a treatment for disorders of consciousness. Psychedelics objectively and reliably produce mystical experiences. Common mechanisms underlying diverse alterations of consciousness involve the disruption of normal functions of the prefrontal cortex and default mode network (DMN). This interruption of ordinary control mechanisms allows for the release of thalamic and other lower brain discharges that stimulate a visual information representation system and release the effects of innate cognitive functions and operators. Converging forms of evidence support the hypothesis that the source of psychedelic experiences involves the emergence of these innate cognitive processes of lower brain systems, with visionary experiences resulting from the activation of innate processes based in the mirror neuron system (MNS). Lysergic acid diethylamide (LSD), N,N-dimethyltryptamine (DMT), psilocybin, and mescaline—the 'classic' psychedelic drugs—can produce a broad range of effects in perception, emotion, cognition, and sense of self. FIG. 8A shows a chart 800 with example effects of psilocybin as compared to a placebo.

Psychedelics can exhibit a wide diversity of effects from subtle intensifications in perception to completely dissolving all sense of space, time, and self.

There are qualitative inter-drug differences between the effects of the four classic psychedelic drugs. Drug dosage is a primary factor in predicting the types of effects that will occur. Effects may unfold temporally over a drug session. Onset effects are distinct from peak effects and some effects have a higher probability of occurring at specific time points over the total duration of drug effects. Furthermore, effects are influenced by non-drug factors traditionally referred to as set and setting, such as personality, pre-dose mood, drug session environment, and external stimuli.

Perceptual effects of psychedelics occur along a dose-dependent range from subtle to drastic. The range of different perceptual effects includes perceptual intensification, distortion, illusion, mental imagery, elementary hallucination, and complex hallucination. Intensifications of color saturation, texture definition, contours, light intensity, sound intensity, timbre variation, and other perceptual characteristics are common. The external world is experienced as if in higher resolution, seemingly crisper and detailed, often accompanied by a distinct sense of 'clarity' or 'freshness' in the environment. Sense of meaning in percepts is altered, e.g., Things around me had a strange new meaning for me' or 'Objects around me engaged me emotionally much more than usual'.

Emotional psychedelic effects are characterized by a general intensification of feelings, increased (conscious) access to emotions, and a broadening in the overall range of emotions felt over the duration of the drug session. Psychedelics can induce unique states of euphoria characterized by involuntary grinning, uncontrollable laughter, silliness, giddiness, playfulness, and exuberance. Negatively experience emotions, e.g., 'I felt afraid' or 'I felt suspicious and paranoid'—are often accompanied by a general sense of losing control, e.g., 'I feared losing control of my mind'. However, the majority of emotional psychedelic effects in supportive contexts are experienced as positive, spontaneous feelings of awe, wonder, bliss, joy, fun, excitement, peace, love, etc., are also consistent themes across experimental and anecdotal reports.

Psychedelic also have cognitive effects. Acute changes in the normal flow of linear thinking, e.g., 'My thinking was muddled' or 'My thoughts wandered freely' are common. This is reflected in reduced performance on standardized measures of working memory and directed attention. Crucially, cognitive impairments related to acute psychedelic effects are dose-dependent extremely low doses, known as micro doses, have been anecdotally associated with improvements in cognitive performance as a claim that urgently requires empirical verification through controlled research. Certain cognitive traits associated with creativity can increase under psychedelics such as divergent thinking, use of unlikely language patterns or word associations, expansion of semantic activation, and attribution of meaning to perceptual stimuli especially musical stimuli. Primary-process thinking is characterized phenomenologically by image fusion, unlikely combinations or events, sudden shifts or transformations of images, and/or contradictory or illogical actions, feelings, or thoughts. Psilocybin and LSD have been shown to increase primary-process thinking as well as the subjective bizarreness and dreamlike nature of mental imagery associated with verbal stimuli. Cognitive flexibility (or 'loosening' of cognition) and optimism can remain for up to 2 weeks after the main acute drug effects have dissipated. Furthermore, long-term increases in creative problem-solving ability and personality trait openness have been measured after just one psychedelic experience.

Psychedelics can have an effect on an individual's ego or ego-dissolution experiences. Under peyote, the line of demarcation drawn between 'object' and 'subject' in normal state may be changed. The body, the ego, may become objective in a certain way, and the objects may come subjective. Effects on sense of self and ego occur along a dose-dependent range spanning from subtle to drastic. Subtle effects are described as a 'softening' of ego with increased insight into one's own habitual patterns of thought, behavior, personal problems, and past experiences; effects which were utilized in 'psycholytic' psychotherapy. Drastic ego-effects, known as ego dissolution, are described as "the dissolution of the sense of self and the loss of boundaries between self and world", e.g., 'I felt like I was merging with my surroundings' or 'All notion of self and identity dissolved away' or 'I lost all sense of ego' or 'I experienced a loss of separation from my environment' or 'I felt at one with the universe'. Ego dissolution is more likely to occur at higher doses. Furthermore, certain psychedelic drugs cause ego dissolution experience more reliably than others; psilocybin, for example, is found to produce full ego dissolution more reliably compared with LSD. Ego dissolution experiences can be driven and modulated by external stimuli, most notably music. Interestingly, subjects who experienced complete ego dissolution in psychedelic-assisted therapy were more likely to evidence positive clinical outcomes as well as long-term changes in life outlook and the personality trait openness.

Promising preliminary data have been produced with psilocybin in anxiety, depression, smoking, alcoholism, and with MDMA for post-traumatic stress disorder (PTSD) and alcoholism. They are also being used for opioid addiction, PTSD, anorexia, post-treatment Lyme disease syndrome, Alzheimer's disease and alcoholism in people with depression. Some treatment effects may last even for up to 6 months. For smoking addiction, effects lasted twelve months and more than 85 percent of the subjects rated their psilocybin trip as one of the five most meaningful and spiritually significant experiences of their lives.

One advantage of psychedelics is that they unblock repressed memories. Their effects may be non-specific or specific. Psychedelic users may report less depression, anxiety, guilt, and anger, and they feel more self-accepting, tolerant, and deeply religious and sensually alert. In addition, they are able to exhibit greater regression, abreaction (sudden relief from a repressed emotion), intense transference, and symbolic drama. As a result, LSD has been associated with various mystical experiences and access to the unconscious too.

Psychedelics have been associated with ego-dissolution, thought disorder and misperceptions or delusions. However, a long-term study of tens of thousands of people with LSDS reported no increased level of psychiatric problems. Psychedelics are also not being used in people with uncontrolled hypertension as it can raise blood pressure.

The cyberdelic implementation disclosed herein may be used to enhance self-connection as a supplement to or instead of the virtual therapeutic platform disclosed herein. The cyberdelic implementation may be specifically designed to impact the same brain circuits using parallel perceptual experiences.

The cyberdelic implementation is a technology solution that targets the same brain substrates as chemically constituted psychedelics. Accordingly, the disclosure provided herein regarding psychedelics applies to this cyberdelic implementation, without use of a consumable medicine. This cyberdelic solution is a digital therapeutic and a corporate and social application that enhances access to an altered perception of the world and a renewed sense of self.

Despite the increase in mental disorders, the pipeline to treat mental disorders treatments remains impoverished. In this impoverished milieu, combination therapies offer some promise. However, a combination of psychedelic assisted psychotherapy represents a paradigm shift that provides tremendous benefit.

Psychedelics may offer relief from many symptoms in syndromes such as anxiety, depression, psychosomatic diseases and addiction. Clinical studies administering psychedelics with psychotherapy have shown preliminary evidence of robust efficacy in treating anxiety and depression. In patients with anxiety associated with life-threatening disease, anxiety was reduced for 2 months after two doses of LSD.

Psychedelic actions may be, in part, explained by significant serotonin 2A receptor (5HT-2A) agonist properties that can alter consciousness in a marked and novel way. However, they may also effect other receptors such as 5HT-2C, 5HT1A, dopamine, norepinephrine, histamine and glutamate. Extensive neuroimaging data indicates that psychedelics exert their effects by decreased activity and connectivity in the brain's key connector hubs, enabling a state of unconstrained cognition. In addition, there is increased blood flow to the brain's visual cortex, and decreased connectivity between brain regions involved in memory, navigation and future-based thinking that correlate with correlated strongly with ratings of "ego-dissolution" and "altered meaning". In fact, key components of the "self" circuit (default mode network) instrumental in constructing a picture of who we are to ourselves are disrupted. Other brain-based findings include decreased threat sensitivity in visual cortex, decreased amygdala activation via the right prefrontal cortex. There are also global increases in brain entropy that were associated with greater trait openness fourteen days later.

With these brain-based changes in identity, memory, perception and future-based thinking, there are numerous reports of life-changing alleviation of burdensome anxiety, depression and being stuck, as with obsessive-compulsive disorder.

While the benefits of psychedelics are incontrovertible, there are also several reports of untoward effects. These include antisocial behavior, ongoing drug abuse by perpetuating the euphoriant properties, psychosis, depression, abandonment of social responsibilities, transcendence, and grandiosity.

Accordingly, psychedelics have therapeutic potential for a wide variety of mental disorders by changing how individuals conceive of their own identities, the pasts, and the future. Optimal dosages depend on individual brain anatomy, physiology, and biochemistry. The dose may difficult to control in laboratory settings.

According to implementations, a paradigm may be selected using a natural language processing (NLP) toolkit as well as machine learning from the multi-variable data input and outputs. The NLP toolkit may be part of or may itself be a machine learning model. Latent semantic analysis and singular value decomposition may be applied as well. An output may have a variety of components such as a first perception component that may have a variance explained ~23%. Top-ranking words that may be associated are visuals, color, visual, pattern, saw, reality, face, their, outside, vision. A second body load component may have a variance explained of ~13%. Top-ranking words that may be associated are visuals, stimulation, mood, compound, peak, material, visual, dosage, minute, and comedown. A third preparation component may have a variance explained of ~9%. Top ranking words that may be associated are boil, bowl, smell, add, ounce, filter, strain, pour, material, mix. A fourth dependence component may have a variance explained of ~7%. Top ranking words that may be associated are addict, addiction, withdrawal, nausea, vomit, sick, money, puke, warm, tolerance. A fifth dependence component may have a variance explained of ~5%. Top ranking words that may be associated are withdrawal, depression, anxiety, prescribe, vision, symptom, nausea, boil, medication, reality.

Psychedelics offer a wide range of experiences. The diversity of subjective effects elicited by different compounds has been attributed to many variables: the internal state of the user, the surroundings, and the specific biology as it relates to pathways impacted by psychedelics. One natural language processing databank is the Erowid Experience Vault. Latent semantic analysis to group words may be applied in experiments to make associations.

Figure 8B:
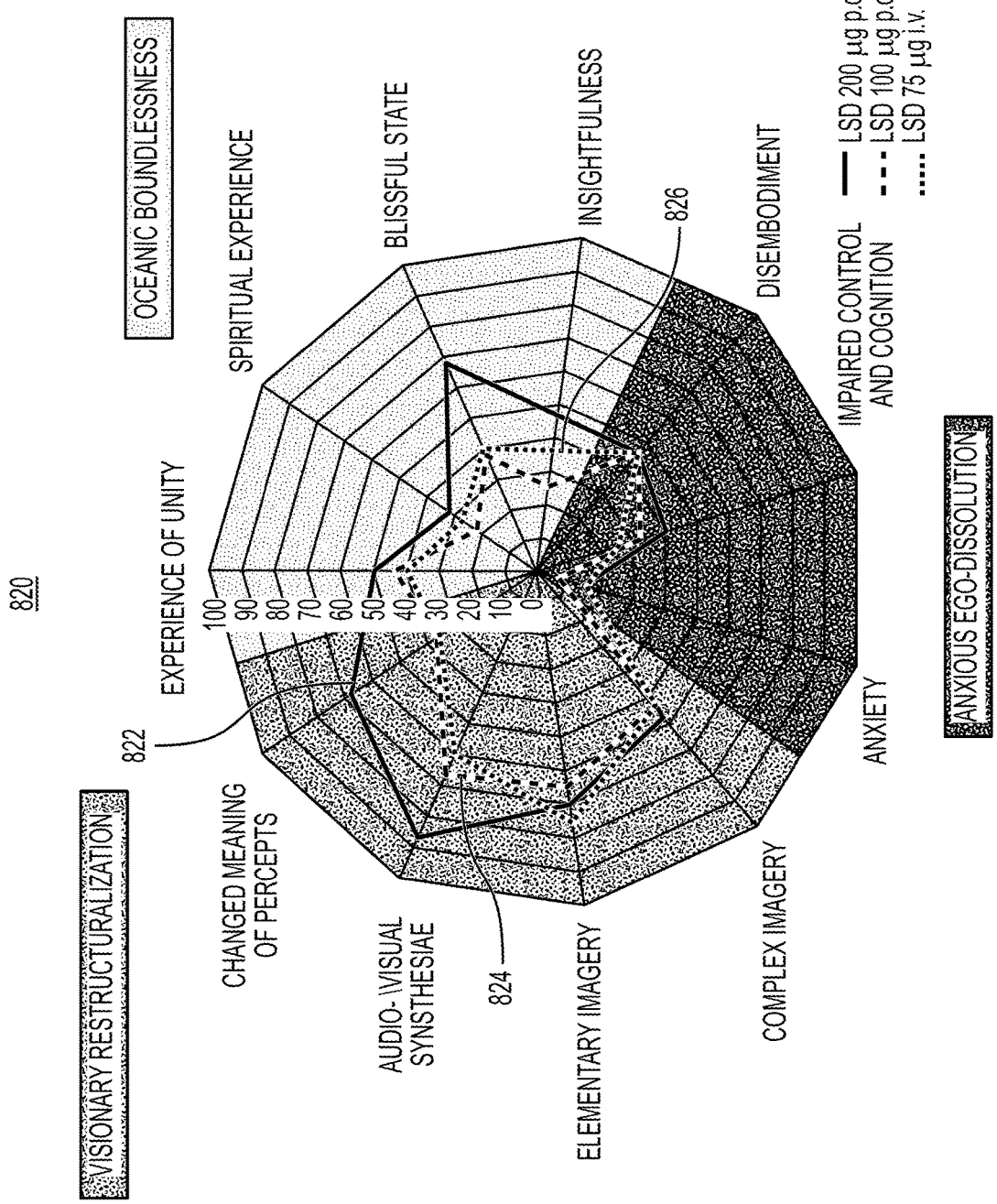
FIG. 8B shows example effects of various doses of LSD as they related to anxious ego-solution, according to techniques presented herein.

Actual experience may be categorized as a first set including perception, emotion, cognition, a second set including classic psychedelics produce visual effects, a third set including bodily experiences, and fourth set including ego dissolution. FIG. 8B shows a diagram 820 of the effects of various doses of LSD as they related to anxious ego-solution. As shown, various doses of LSD including a 200 microgram does 822, a 100 microgram dose 824, and a 75 microgram dose 826 correspond to varyin ganxious ego-dissolution effects, visionary restructuralization effects, and oceanic boundlessness effects related to anxiety, complex imagery, elementary imagery, audio-visual synesthesia, changed meaning of percepts, experience of unity, spiritual experience, blissful state, insightfulness, disembodiment, and impaired control and cognition.

FIGS. 9A-16 show example diagrams for implementations disclosed herein. The different variables included in these figure may be operationalized on rating scales to design scripts and corresponding treatments, and to correlate these variables with outcomes in order to make adjustments to the scripts to optimize a treatment and user response. For example, pixel intensity may be adjusted in the design components that represent sacredness until response to this is optimized.

Figures 9A, 9B:
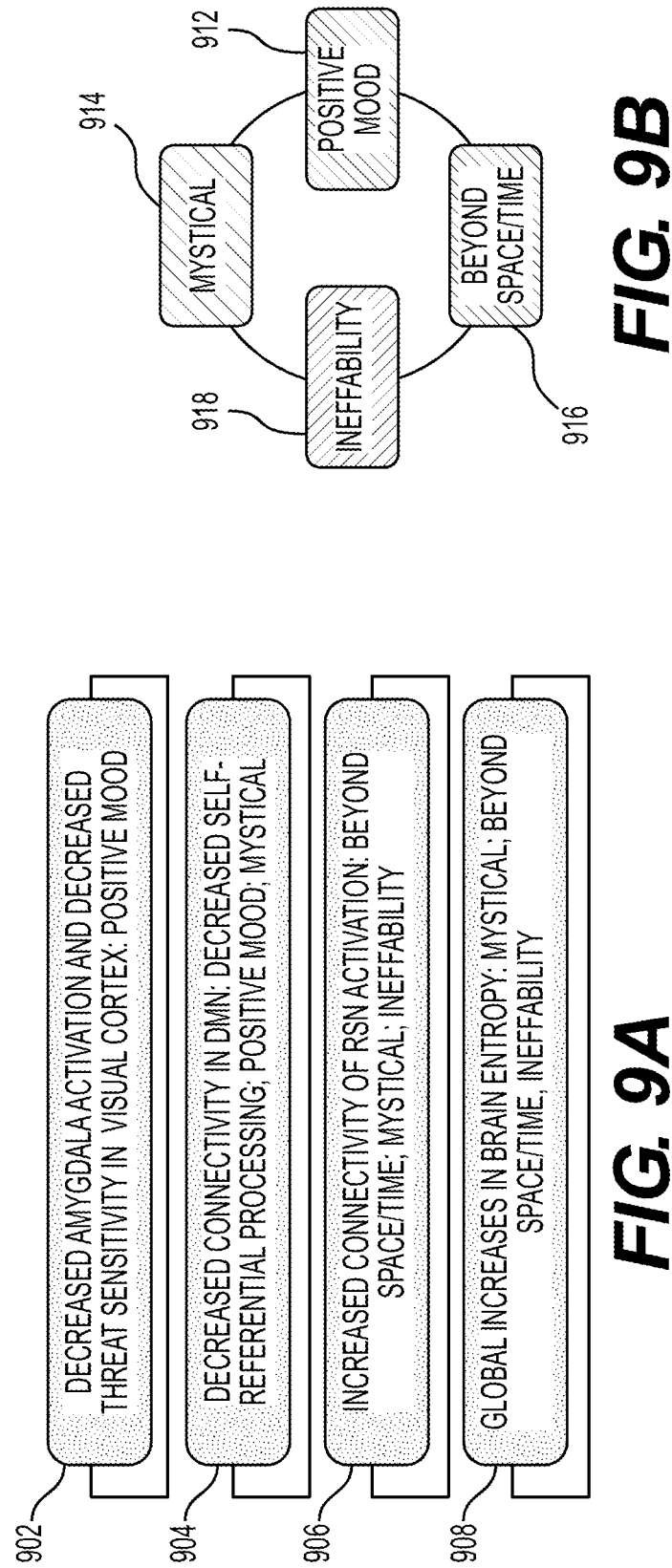
FIG. 9A shows cyberdelic causes and effects, according to techniques presented herein.
FIG. 9B shows cyberdelic factors, according to techniques presented herein.

FIGS. 9A and 9B shows a set of techniques and factors based on the cyberdelic implementation disclosed herein. FIGS. 9A-16 generally refer to the cyberdelic platform and may be applied to provide psychedelic type results. The cyberdelic platform may be implemented via any technologically disclosed herein (e.g., using omnichannel therapeutic system 400). For example, auditory treatments may be selected to provide psychedelic type results, based on the cyberdelic implementation techniques disclosed herein.

As shown in FIG. 9A, at 902, a decreased amygdala activation and decreased threat sensitivity in visual cortex may be triggered for a positive mood. At 904, decreased connectivity in DMN and decreased self-referential processing may be triggered for a positive mood and mystical implementation. At 906, an increased connectivity of RSN activation may be triggered for a beyond space/time, mystical, and ineffability implementation. At 908, and a global increase in brain entropy may be triggered for mystical, beyond space/time, and ineffability implementations. FIG. 9B shows the various implementations including a positive mood 912, mystical implementation 914, beyond space/time 916 implementation, and ineffability 918.

Figure 11:
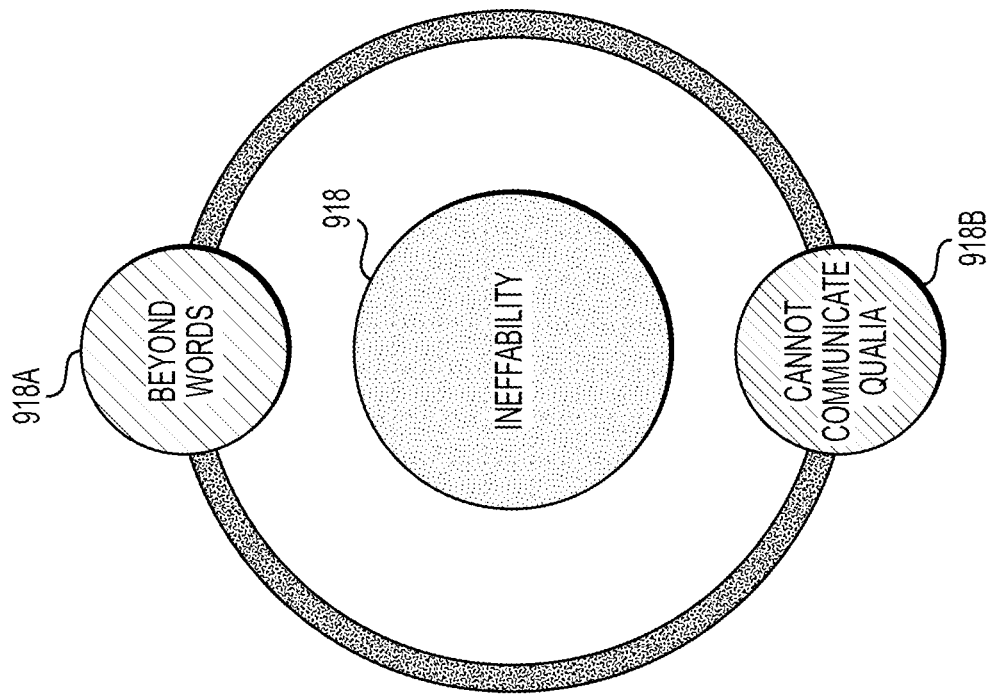
FIG. 11 shows an ineffability cyberdelic implementation, according to techniques presented herein.
Figure 10:
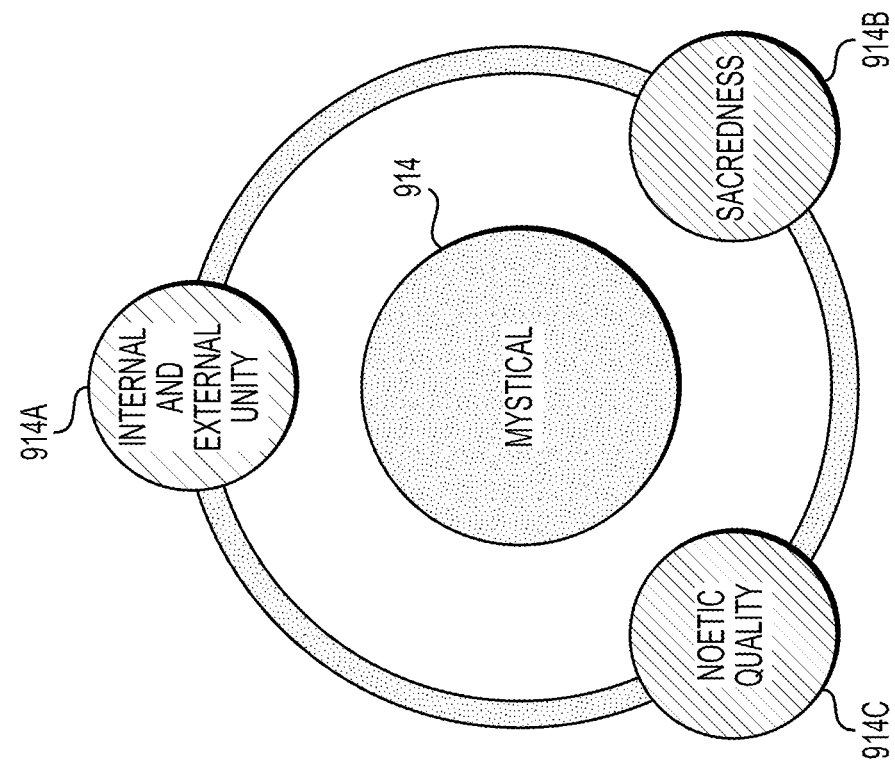
FIG. 10 shows a mystical cyberdelic implementation, according to techniques presented herein.
Figure 13:
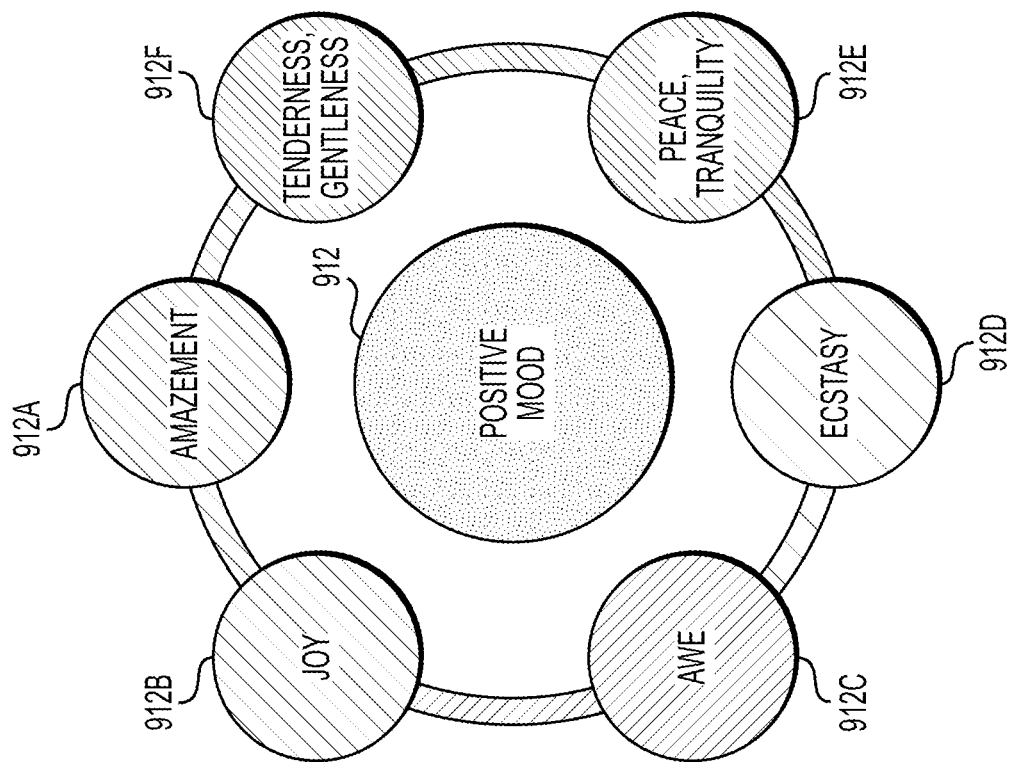
FIG. 13 shows a positive mood cyberdelic implementation, according to techniques presented herein.
Figure 12:
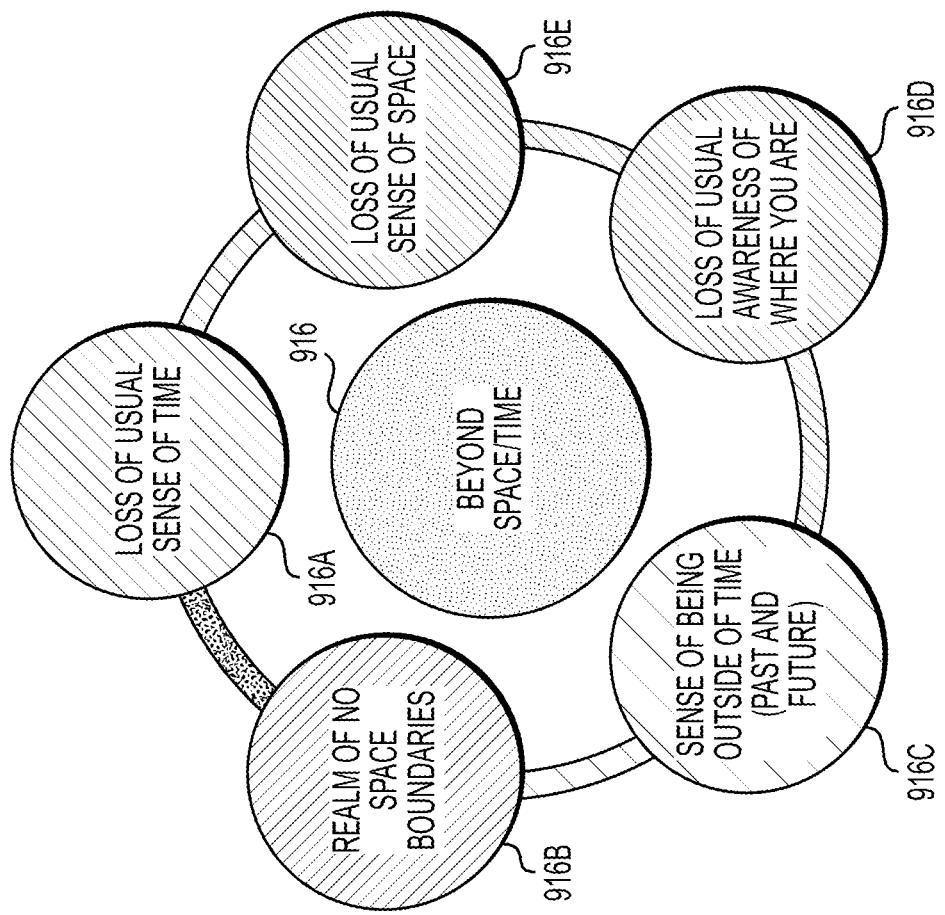
FIG. 12 shows a beyond space/time cyberdelic implementation, according to techniques presented herein.
Figure 15:
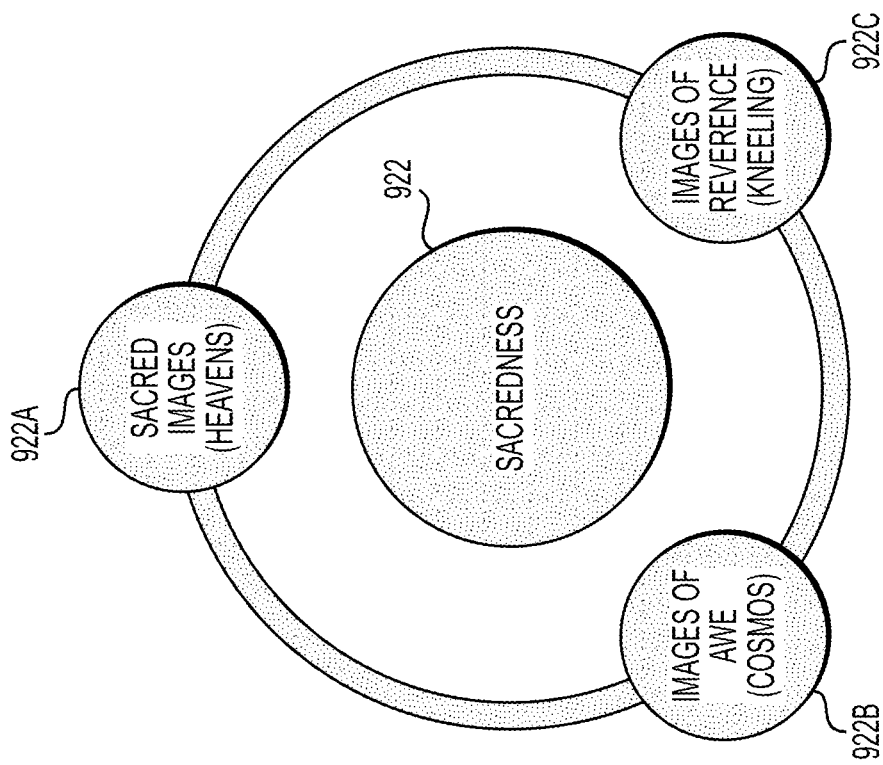
FIG. 15 shows a sacredness cyberdelic implementation, according to techniques presented herein.
Figure 14:
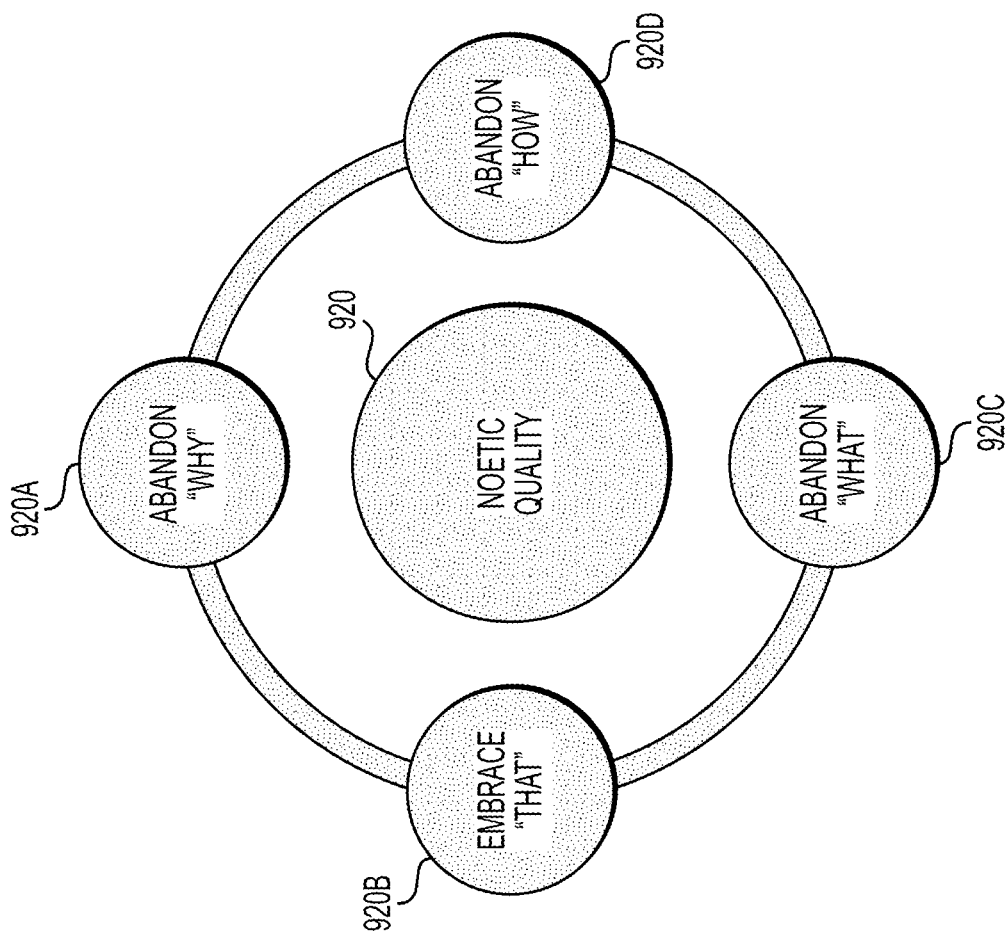
FIG. 14 shows a noetic quality cyberdelic implementation, according to techniques presented herein.
Figure 16:
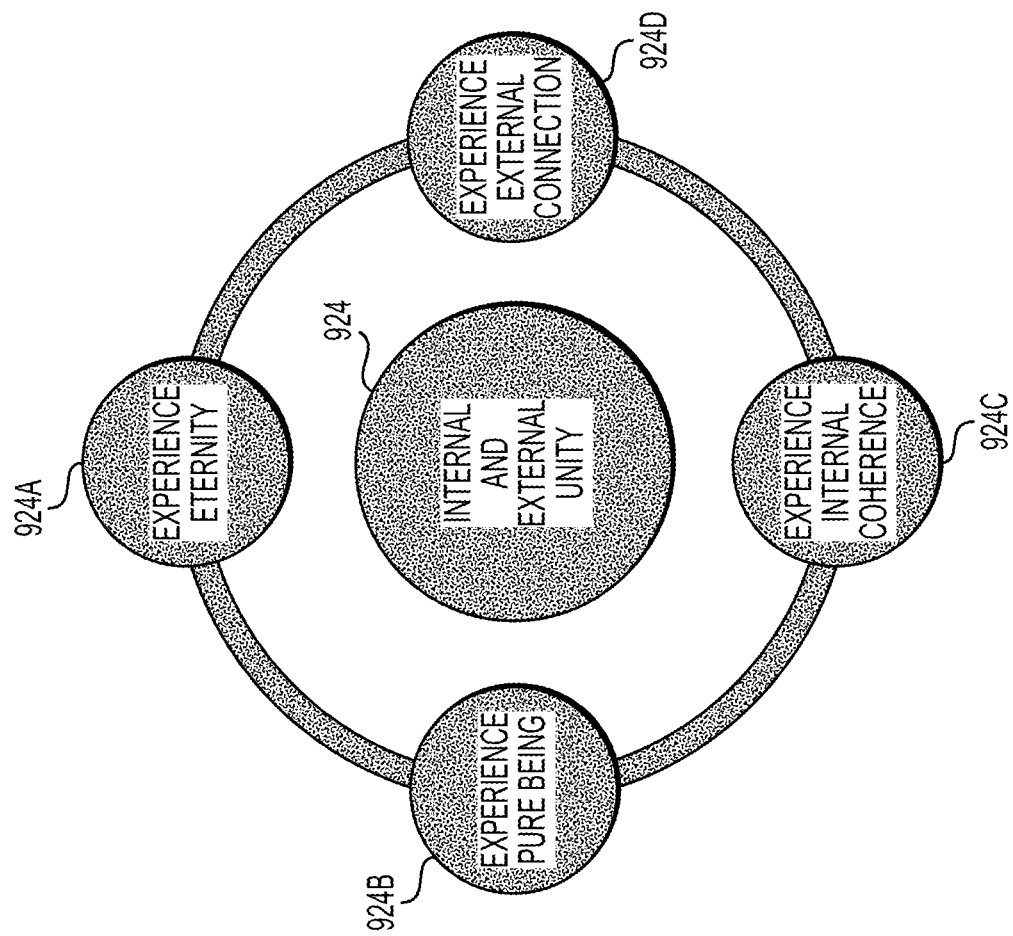
FIG. 16 shows an internal and external unity cyberdelic implementation, according to techniques presented herein.

FIG. 10 is a diagram for mystical 914 inputs including internal and external unity 914A, sacredness 914B, and noetic quality 914C. FIG. 11 is a diagram for ineffability 918 inputs including beyond words 918A and for those that cannot communicate qualia 918B. FIG. 12 is a diagram for beyond space/time 916 inputs including loss of usual sense of time 916E, loss of usual sense of space 916A, loss of usual awareness of where one is 916D, sense of being outside of time (e.g., past and future) 916C, and a realm of no space boundaries 916B. FIG. 13 is a diagram for positive mood 912 inputs including amazement 912A, tenderness or gentleness 912F, peace or tranquility 912E, ecstasy 912D, awe 912C, and joy 912B. FIG. 14 is a diagram for mystical-noetic quality 920 inputs including abandonment based on "why" 920A, abandonment based on "how" 920D, abandonment based on "what" 920C, and embrace based on "that" 920B. FIG. 15 is a diagram for mystical-sacredness 922 inputs including sacred images (e.g., heavens) 922A, images of reverence (e.g., kneeling) 922C, and images of awe (e.g., cosmos) 922B. FIG. 16 is a diagram for mystical internal and external unity 924 inputs including experience eternity 924A, experience external connection 924D, experience internal coherence 924C, and experience pure being 924B.

The cyberdelic implementation disclosed herein is based on a number of pillars. First, psychedelics change brain chemistry. Second, when psychedelics change brain chemistry, they also change brain electrical activation. Third, changes in brain electrical activity start as a "dial-tone", followed by a "telephone number" whereby the brain's networks act as a telephone that dials into the internal and external milieu. Fourth, the internal milieu involves networks that are involved in perception, memory and cognition. Fifth, the external network will be reached through ISM band frequencies accessed by IoT devices. IoT protocols mostly use ISM band frequencies of 4.33 GHz, 915 MHz, 2.4 GHz. 5 GHz.

The 528 Hz band can be used to repair broken DNA. Psychedelics likely activate this frequency. The 528 Hz frequency band may be used both as a light and sound and has been shown to reduce anxiety in rats and reduces toxicity that impacts cells. In IC50 of ethanol, the frequency of 528 Hz increased cells viability about 20% and the level of ROS production has been reduced up to 100%. In the 528 Hz condition, mean levels of cortisol significantly decreased, chromogranin A (Salivary biomarker of stress) tended to decrease, and oxytocin significantly increased after music exposure. However, no significant change was observed in any salivary biomarkers in the 440 Hz condition. Tension-anxiety and total mood disturbance scores were significantly reduced after exposure to 528 Hz music, while there was no significant difference following 440 Hz music.

Sound healing is effective in healing physical, generational and emotional trauma in our DNA using vibrations and frequencies. According to implementations of the disclosed subject matter, a 528 Hz audio exposure decreases stress and PTSD symptoms even after five minutes. The use of a Gregorian chant decreased the state of anxiety of mothers of hospitalized children in single room accommodations within a quaternary care pediatric hospital.

The frequency band 432 Hz may also be applied. 432 Hz tuned music is associated with a slight decrease of mean (systolic and diastolic) blood pressure values, a marked decrease in the mean of heart rate (−4.79 bpm, p=0.05) and a slight decrease of the mean respiratory rate values (1 r.a., p=0.06), compared to 440 Hz. A user exposed to music may be more focused on listening to music and more generally satisfied after the sessions in which they listen to 432 Hz tuned music. Clinical anxiety levels may be decreased based on audio at the frequency of 432 Hz which may also be effective in decreasing salivary cortisol levels before tooth extraction. 432 Hz music has some significant calming effect as reflected by increased alpha activities without any significant effect upon the sleep latency in the daytime naps.

The cyberdelic implementation uses the 528 Hz and 432 Hz frequency bands to create visual and auditory states to compare, contrast and integrate. A user's brain may be connected with these frequencies. Additional frequencies of interest are 396 Hz and 417 Hz.

According to an implementation, omnichannel therapeutic system 400 may be used to provide therapy by eye. Such therapy may be used by providing digital content via an applicable user platform 410 such that the digital content has an effect on retinas, corneas, and/or rods. Similarly, olfactory and multisensory therapy may be implemented in accordance with the techniques disclosed herein.

One or more implementations of the disclosed subject matter may be implemented in the metaverse. The metaverse, also known as the spatial internet, corresponds to virtual spaces where a user can create and explore with other people that the user is not in physical contact or proximity with. The metaverse may be spread out over a variety of collective virtual shared spaces, created by the convergence of virtually enhanced physical reality and physically persistent virtual space, including the sum of all virtual worlds, augmented reality, and internet products and services.

Accordingly, any applicable aspect of the disclosed subject matter may be implemented in the metaverse. For example, user inputs 402 may be generated for a version of user 412 within the metaverse. The version of user 412 may be a metaverse projection of a physical user. The version of user 412 within the metaverse may receive digital content within the metaverse itself (e.g., via one or more metaverse platforms that are digital platforms accessible within the metaverse) or may receive digital content via user platforms 410 connected to the metaverse. Accordingly, the implementations disclosed herein including those disclosed in reference to FIGS. 4A-4F may be implemented in the metaverse.

It should be understood that embodiments in this disclosure are exemplary only, and that other embodiments may include various combinations of features from other embodiments, as well as additional or fewer features. Implementations disclosed herein may partially or substantially alter VR function (e.g., the function of a VR device or AR device).

In general, any process or operation discussed in this disclosure that is understood to be computer-implementable, may be performed by one or more processors of a computer system. A process or process step performed by one or more processors may also be referred to as an operation. The one or more processors may be configured to perform such processes by having access to instructions (e.g., software or computer-readable code) that, when executed by the one or more processors, cause the one or more processors to perform the processes. The instructions may be stored in a memory of the computer system. A processor may be a central processing unit (CPU), a graphics processing unit (GPU), or any suitable types of processing unit.

A computer system, such as a system or device implementing a process or operation in the examples above, may include one or more computing devices, such as one or more of the systems or devices. One or more processors of a computer system may be included in a single computing device or distributed among a plurality of computing devices. One or more processors of a computer system may be connected to a data storage device. A memory of the computer system may include the respective memory of each computing device of the plurality of computing devices.

Figure 17:
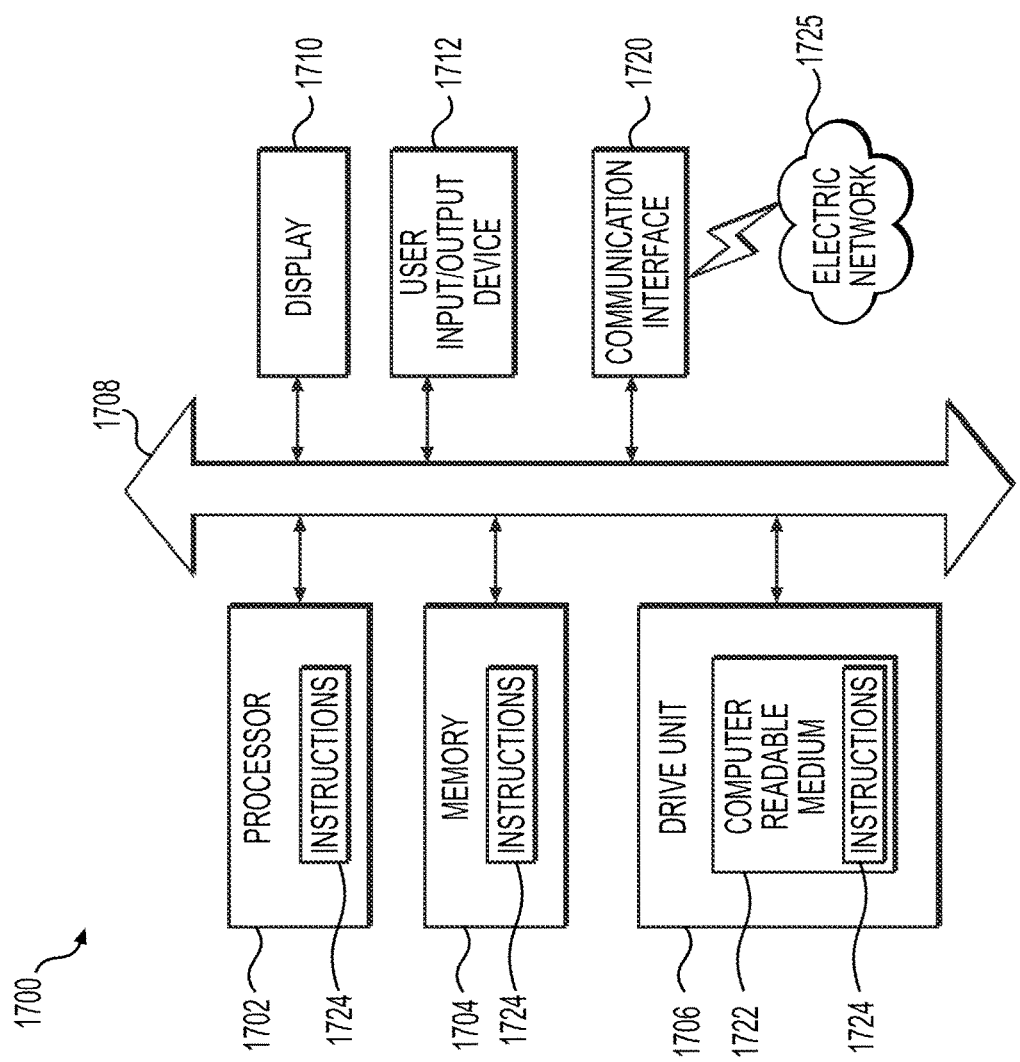
FIG. 17 shows a functional block diagram of a computer system, according to techniques presented herein.

Any aspect of the techniques disclosed herein may be implemented in software, hardware, or firmware, as applicable. FIG. 17 is a simplified functional block diagram of a computer system 1700 that may be configured as a device for executing the methods described herein, according to exemplary embodiments of the present disclosure. FIG. 17 is a simplified functional block diagram of a computer system that may be used for therapeutic treatments and/or another system according to exemplary embodiments of the present disclosure. In various embodiments, any of the systems (e.g., computer system 1700) herein may be an assembly of hardware including, for example, a data communication interface 1720 for packet data communication. The computer system 1700 also may include a central processing unit ("CPU") 1702, in the form of one or more processors, for executing program instructions. The computer system 1700 may include an internal communication bus 1708, and a storage unit 1706 (such as ROM, HDD, SDD, etc.) that may store data on a computer readable medium 1722, although the computer system 1700 may receive programming and data via network communications. The computer system 1700 may also have a memory 1704 (such as RAM) storing instructions 1724 for executing techniques presented herein, although the instructions 1724 may be stored temporarily or permanently within other modules of computer system 1700 (e.g., processor 1702 and/or computer readable medium 1722). The computer system 1700 also may include input and output ports 1712 and/or a display 1710 to connect with input and output devices such as keyboards, mice, touchscreens, monitors, displays, etc. The various system functions may be implemented in a distributed fashion on a number of similar platforms, to distribute the processing load. Alternatively, the systems may be implemented by appropriate programming of one computer hardware platform. One or more components of the computer system 1700 may be connected via an electronic network 1725 which may be provide access to one or more cloud components.

Program aspects of the technology may be thought of as "products" or "articles of manufacture" typically in the form of executable code and/or associated data that is carried on or embodied in a type of machine-readable medium. "Storage" type media include any or all of the tangible memory of the computers, processors or the like, or associated modules thereof, such as various semiconductor memories, tape drives, disk drives and the like, which may provide non-transitory storage at any time for the software programming. All or portions of the software may at times be communicated through the Internet or various other telecommunication networks. Such communications, for example, may enable loading of the software from one computer or processor into another, for example, from a management server or host computer of the mobile communication network into the computer platform of a server and/or from a server to the mobile device. Thus, another type of media that may bear the software elements includes optical, electrical and electromagnetic waves, such as used across physical interfaces between local devices, through wired and optical landline networks and over various airlinks. The physical elements that carry such waves, such as wired or wireless links, optical links, or the like, also may be considered as media bearing the software. As used herein, unless restricted to non-transitory, tangible "storage" media, terms such as computer or machine "readable medium" refer to any medium that participates in providing instructions to a processor for execution.

While the presently disclosed methods, devices, and systems are described with exemplary reference to transmitting data, it should be appreciated that the presently disclosed embodiments may be applicable to any environment, such as a desktop or laptop computer, a mobile device, a wearable device, a text-based platform, an audio-based platform, a video-based platform, an automobile communication system, a home communication system, etc. This may apply to devices such as holographic devices or any devices associated with web 3.0 or the spatial web, or the like. Also, the presently disclosed embodiments may be applicable to any type of Internet protocol.

It should be appreciated that in the above description of exemplary embodiments of the invention, various features of the invention are sometimes grouped together in a single embodiment, figure, or description thereof for the purpose of streamlining the disclosure and aiding in the understanding of one or more of the various inventive aspects. This method of disclosure, however, is not to be interpreted as reflecting an intention that the claimed invention requires more features than are expressly recited in each claim. Rather, as the following claims reflect, inventive aspects lie in less than all features of a single foregoing disclosed embodiment. Thus, the claims following the Detailed Description are hereby expressly incorporated into this Detailed Description, with each claim standing on its own as a separate embodiment of this invention.

Furthermore, while some embodiments described herein include some, but not other features included in other embodiments, combinations of features of different embodiments are meant to be within the scope of the invention, and form different embodiments, as would be understood by those skilled in the art. For example, in the following claims, any of the claimed embodiments can be used in any combination.

Thus, while certain embodiments have been described, those skilled in the art will recognize that other and further modifications may be made thereto without departing from the spirit of the invention, and it is intended to claim all such changes and modifications as falling within the scope of the invention. For example, functionality may be added or deleted from the block diagrams and operations may be interchanged among functional blocks. Steps may be added or deleted to methods described within the scope of the present invention.

The above disclosed subject matter is to be considered illustrative, and not restrictive, and the appended claims are intended to cover all such modifications, enhancements, and other implementations, which fall within the true spirit and scope of the present disclosure. Thus, to the maximum extent allowed by law, the scope of the present disclosure is to be determined by the broadest permissible interpretation of the following claims and their equivalents, and shall not be restricted or limited by the foregoing detailed description. While various implementations of the disclosure have been described, it will be apparent to those of ordinary skill in the art that many more implementations are possible within the scope of the disclosure. Accordingly, the disclosure is not to be restricted except in light of the attached claims and their equivalents.

What is claimed is:

1. A computer-implemented method for treating a medical condition via a digital therapeutic platform, the method comprising:
   receiving, by one or more processors, one or more user inputs of a user and feedback based on a user consumption of one or more prior therapeutic digital content via a user platform;
   updating, by the one or more processors, a decision model of a script generator based on previous content inputs by the user and a historical usage of the user, thereby producing an updated decision model;
   generating, by the one or more processors, a script at the updated decision model of the script generator, based on the one or more user inputs;
   adjusting, by the one or more processors, a therapeutic machine learning platform based on the feedback, thereby producing an adjusted therapeutic machine learning platform;
   determining therapeutic digital content by applying the script as an input to the adjusted therapeutic machine learning platform;
   receiving the therapeutic digital content via at least one of a therapeutic content database or a content generator;
   identifying a user platform to output the therapeutic digital content;
   modifying the therapeutic digital content for output via the user platform; and
   providing the therapeutic digital content via the user platform.

2. The computer-implemented method of claim 1, wherein generating the script comprises:
   receiving a paradigm as an output of the script machine learning model.

3. The computer-implemented method of claim 1, wherein the therapeutic machine learning platform comprises a scripting engine, a generational engine, and a thematic engine.

4. The computer-implemented method of claim 3, wherein the thematic engine requests the therapeutic digital content from at least one of the therapeutic content database or the content generator.

5. The computer-implemented method of claim 4, wherein the content generator is configured to generate content or modify content received from the therapeutic content database.

6. The computer-implemented method of claim 4, wherein the content generation comprises a generative adversarial network (GAN) engine.

7. The computer-implemented method of claim 1, wherein the feedback is generated using one or more sensors.

8. The method of claim 7, wherein the feedback is collected using one or more of a wearable device, a medical device, a patch sensor, a biometric sensor, or a motion sensor.

9. The method of claim 1, wherein the user platform is one or more of a web platform, a virtual reality (VR) application, an augmented reality (AR) application, a mobile application, a holographic application, or a wearable device application.

10. The method of claim 1, wherein the user input comprises a medication and wherein the therapeutic digital content is selected, at least in part, based on the medication.

11. The method of claim 1, further comprising providing holotropic breathwork guidance, the holotropic breathwork guidance being generated based at least in part on the therapeutic digital content provided to the user.

12. The method of claim 1, further comprising determining a dosage amount of the therapeutic digital content by the script generator, the dosage amount being determined based on at least one of the one or more user inputs or the feedback.

13. The method of claim 1, wherein the user platform is a metaverse platform.

14. An omnichannel digital therapeutic system comprising:
   a processor;
   a memory;
   a script generator comprising a script machine learning model, the script generator configured to:
   receive one or more user inputs;
   update the script machine learning model of the script generator based on previous content inputs by the user and a historical usage of the user, thereby producing an updated script machine learning model; and
   generate a script at the updated machine learning model based on the one or more user inputs;

a therapeutic machine learning platform, the therapeutic machine learning platform configured to:
receive user feedback based on a user consumption of one or more prior therapeutic digital content via a user platform;
receive the script as an input;
adjust the therapeutic machine learning platform based on the feedback, thereby producing an adjusted therapeutic machine learning platform;
determine therapeutic digital content based on the script;
receive the therapeutic digital content from at least one of a therapeutic content database or a content generator; and
a content rendering and distribution component configured to:
identify the user platform to output the therapeutic digital content;
modify the therapeutic digital content for output via the user platform; and
provide the therapeutic digital content via the user platform, wherein the processor is configured to receive additional feedback based on user consumption of the digital content via the user platform.

15. The system of claim 14, wherein the therapeutic machine learning platform comprises a therapeutic machine learning model configured to determine the therapeutic digital content based on the script and the one or more user inputs.

16. The system of claim 14, wherein the therapeutic machine learning platform further comprises a thematic engine.

17. The system of claim 16, wherein the thematic engine requests the therapeutic digital content from at least one of the therapeutic content database or the content generator.

18. The system of claim 17, wherein the content generator is configured to generate content or modify content received from the therapeutic content database.

19. The system of claim 18, wherein the content generation comprises a generative adversarial network (GAN) engine.

20. A method comprising:
receiving one or more user inputs generated based on one or more user actions in a metaverse and feedback based on a user consumption of one or more prior therapeutic digital content via a user platform;
updating a decision model of a script generator based on a historical usage of the user, thereby producing an updated decision model;
generating a script at a script generator, based on the one or more user inputs;
adjusting a therapeutic machine learning platform based on the feedback, thereby producing an adjusted therapeutic machine learning platform;
determining therapeutic digital content by applying the script as an input to the adjusted therapeutic machine learning platform;
receiving the therapeutic digital content via at least one of a therapeutic content database or a content generator;
identifying a user platform to output the therapeutic digital content, the user platform being a metaverse platform;
providing the therapeutic digital content via the user platform; and
receiving additional feedback based on user consumption of the therapeutic digital content via the user platform.

* * * * *